United States Patent
Dube et al.

(10) Patent No.: US 7,482,456 B2
(45) Date of Patent: Jan. 27, 2009

(54) 8-(3-BIARYL)PHENYLQUINOLINE PHOSPHODIESTERASE-4 INHIBITORS

(75) Inventors: Daniel Dube, St-Lazare (CA); Laurence Dube, Ste-Dorothée (CA); Michel Gallant, Kirkland (CA); Patrick Lacombe, Montreal (CA); Denis Deschenes, Dorval (CA); Dwight Macdonald, L'Ile Bizard (CA)

(73) Assignee: Merck Frosst Canada, Kirkland, Quebec ( * ) Notice: Subject to any disclaimer, the term of this patent is extended or adjusted under 35 U.S.C. 154(b) by 595 days.

(21) Appl. No.: 10/554,176

(22) PCT Filed: Apr. 27, 2004

(86) PCT No.: PCT/CA2004/000622

§ 371 (c)(1),
(2), (4) Date: Oct. 21, 2005

(87) PCT Pub. No.: WO2004/096220

PCT Pub. Date: Nov. 11, 2004

(65) Prior Publication Data

US 2006/0223850 A1  Oct. 5, 2006

Related U.S. Application Data

(60) Provisional application No. 60/466,542, filed on Apr. 30, 2003.

(51) Int. Cl.
    C07D 215/38 (2006.01)
(52) U.S. Cl. ..................................... 546/159; 546/153
(58) Field of Classification Search ................ 546/159, 546/153
    See application file for complete search history.

(56) References Cited

U.S. PATENT DOCUMENTS

| 6,521,618 B2 * | 2/2003 | Boschelli et al. | 514/231.5 |
| 6,919,353 B2 * | 7/2005 | Dube et al. | 514/314 |
| 7,153,968 B2 * | 12/2006 | Dube et al. | 546/107 |

FOREIGN PATENT DOCUMENTS

| WO | WO 02/094823 | 11/2002 |
| WO | WO 03/002118 | 1/2003 |
| WO | WO 2004/000814 | 12/2003 |

* cited by examiner

*Primary Examiner*—D. Margaret Seaman
(74) *Attorney, Agent, or Firm*—Sylvia A. Ayler; William Krovatin

(57) ABSTRACT

Novel substituted 8-phenylquinolines represented by Formula (I), wherein the phenyl group at the 8-position contains an aryl or heteroaryl substituent in the meta position, are PDE4 inhibitors.

25 Claims, No Drawings

8-(3-BIARYL)PHENYLQUINOLINE PHOSPHODIESTERASE-4 INHIBITORS

CROSS REFERENCE TO RELATED APPLICATIONS

This application is a U.S. National Phase application under 35.U.S.C. § 371 of PCT Application No. PCT/CA2004/000622, filed Apr. 27, 2004, which claims priority under 35 U.S.C. 119 to U.S. Provisional Application No. 60/466,542, filed Apr. 30, 2003.

BACKGROUND OF THE INVENTION

1. Field of the Invention

The present invention is directed to compounds that are substituted 8-phenylquinolines. In particular, this invention is directed to substituted 8-phenylquinolines which are phosphodiesterase-4 inhibitors wherein the phenyl group at the 8-position contains a meta aryl or heterocyclic group.

2. Related Background

Hormones are compounds that variously affect cellular activity. In many respects, hormones act as messengers to trigger specific cellular responses and activities. Many effects produced by hormones, however, are not caused by the singular effect of just the hormone. Instead, the hormone first binds to a receptor, thereby triggering the release of a second compound that goes on to affect the cellular activity. In this scenario, the hormone is known as the first messenger while the second compound is called the second messenger. Cyclic adenosine monophosphate (adenosine 3',5'-cyclic monophosphate, "cAMP" or "cyclic AMP") is known as a second messenger for hormones including epinephrine, glucagon, calcitonin, corticotrophin, lipotropin, luteinizing hormone, norepinephrine, parathyroid hormone, thyroid-stimulating hormone, and vasopressin. Thus, cAMP mediates cellular responses to hormones. Cyclic AMP also mediates cellular responses to various neurotransmitters.

Phosphodiesterases ("PDE") are a family of enzymes that metabolize 3',5' cyclic nucleotides to 5' nucleoside monophosphates, thereby terminating cAMP second messenger activity. A particular phosphodiesterase, phosphodiesterase-4 ("PDE4", also known as "PDE-IV"), which is a high affinity, cAMP specific, type IV PDE, has generated interest as potential targets for the development of novel anti-asthmatic and anti-inflammatory compounds. PDE4 is known to exist as at lease four isoenzymes, each of which is encoded by a distinct gene. Each of the four known PDE4 gene products is believed to play varying roles in allergic and/or inflammatory responses. Thus, it is believed that inhibition of PDE4, particularly the specific PDE4 isoforms that produce detrimental responses, can beneficially affect allergy and inflammation symptoms. It would be desirable to provide novel compounds and compositions that inhibit PDE4 activity.

A major concern with the use of PDE4 inhibitors is the side effect of emesis which has been observed for several candidate compounds as described in C. Burnouf et al., ("Burnouf"), *Ann. Rep. In Med. Chem.*, 33:91-109(1998). B. Hughes et al., *Br. J. Pharmacol.*, 118:1183-1191(1996); M. J. Perry et al., *Cell Biochem. Biophys.*, 29:113-132(1998); S. B. Christensen et al., *J. Med. Chem.*, 41:821-835(1998); and Burnouf describe the wide variation of the severity of the undesirable side effects exhibited by various compounds. As described in M. D. Houslay et al., *Adv. In Pharmacol.*, 44:225-342(1998) and D. Spina et al., *Adv. In Pharmacol.*, 44:33-89(1998), there is great interest and research of therapeutic PDE4 inhibitors.

International Patent Publication WO9422852 describes quinolines as PDE4 inhibitors. U.S. Pat. No. 6,410,563 describes 8-arylquinoline PDE4 inhibitors.

A. H. Cook, et al., *J. Chem. Soc.*, 413-417(1943) describes gamma-pyridylquinolines. Other quinoline compounds are described in Kei Manabe et al., *J. Org. Chem.*, 58(24):6692-6700(1993); Kei Manabe et al., *J. Am. Chem. Soc.*, 115(12): 5324-5325(1993); and Kei Manabe et al., *J. Am. Chem Soc.*, 114(17):6940-6941(1992).

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, U.S. Pat. No. 5,736,297 describes ring systems useful as a photosensitive composition.

U.S. Pat. Nos. 5,491,147, 5,608,070, 5,622,977, 5,739, 144, 5,776,958, 5,780,477, 5,786,354, 5,798,373, 5,849,770, 5,859,034, 5,866,593, 5,891,896, and International Patent Publication WO 95/35283 describe PDE4 inhibitors that are tri-substituted aryl or heteroaryl phenyl derivatives. U.S. Pat. No. 5,580,888 describes PDE4 inhibitors that are styryl derivatives. U.S. Pat. No. 5,550,137 describes PDE4 inhibitors that are phenylaminocarbonyl derivatives. U.S. Pat. No. 5,340,827 describes PDE4 inhibitors that are phenylcarboxamide compounds. U.S. Pat. No. 5,780,478 describes PDE4 inhibitors that are tetra-substituted phenyl derivatives. International Patent Publication WO 96/00215 describes substituted oxime derivatives useful as PDE4 inhibitors. U.S. Pat. No. 5,633,257 describes PDE4 inhibitors that are cyclo(alkyl and alkenyl)phenyl-alkenyl (aryl and heteroaryl) compounds.

However, there remains a need for novel compounds and compositions that therapeutically inhibit PDE4 with minimal side effects.

SUMMARY OF THE INVENTION

The present invention is directed to novel substituted 8-phenylquinolines that are PDE4 inhibitors, wherein the phenyl group at the 8-position is substituted by an aryl or heterocyclic group in the meta position. This invention also provides a pharmaceutical composition which includes an effective amount of the novel substituted 8-phenylquinoline and a pharmaceutically acceptable carrier. This invention further provides a method of treatment in mammals of, for example, asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, celiac sprue, ulcerative colitis, Crohn's disease, reperfusion injury of the myocardium and brain, inflammatory arthritis, chronic glomerulonephritis, atopic dermatitis, urticaria, adult respiratory distress syndrome, chronic obstructive pulmonary disease in animals, diabetes insipidus, allergic rhinitis, allergic conjunctivitis, vernal conjunctivitis, arterial restenosis, ortherosclerosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, tumour growth and cancerous invasion of normal tissues by the administration of an effective amount of the novel substituted 8-phenylquinoline.

DETAILED DESCRIPTION OF THE INVENTION

In a first aspect the invention is directed to compounds represented by Formula (I):

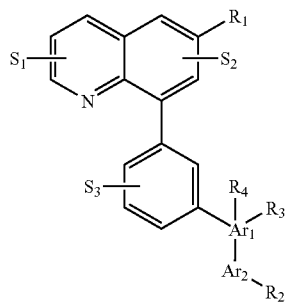

and pharmaceutically acceptable salts, wherein
$S_1$, $S_2$, and $S_3$ are independently
1. H,
2. —OH,
3. halogen,
4. —$C_1$-$C_6$alkyl,
5. —O—$C_1$-$C_6$alkyl optionally substituted with 1, 2 or 3 halogens, or
6. —CN;

$R_1$ is
1. —($C_1$-$C_6$alkyl)-$SO_n$—($C_1$-$C_6$alkyl) group, optionally substituted with 1, 2 or 3 substituents; wherein each substituent is independently a halogen, —OH and —CN,
2. —C(O)—O-aryl,
3. —C(O)—NH-aryl,
4. —C(O)—NH-heterocycle or N-oxide thereof,
5. —C(O)—NH—$C_1$-$C_6$alkyl,
6. —C(O)—NH-cyclo$C_3$-$C_6$alkyl,
7. —$C_1$-$C_6$alkyl, optionally substituted with 1 to 6 halogens and 1 hydroxy,
8. —COOH,
9. —$C_1$-$C_6$alkyl-COOH,
10. —O—$C_1$-$C_6$alkyl,
11. -cyclo$C_3$-$C_6$alkyl,
12. —$C_3$-$C_6$alkyl-heterocycle,
13. aryl,
14. heterocycle,
15. carbonyl,
16. carbamoyl, or
17. —$SO_n$—($C_1$-$C_6$alkyl);
each n is independently 0, 1, or 2;
$Ar_1$ and $Ar_2$ are each independently an aryl or heterocycle or an N-oxide thereof;

$R_2$ is
1. Hydrogen,
2. aryl optionally substituted with 1, 2 or 3 substituents selected from halogen,
3. heterocycle optionally substituted with 1, 2 or 3 halogens,
4. —$C_1$-$C_6$alkyl optionally substituted with 1, 2 or 3 substituents selected from hydroxy and halogen,
5. —COOH,
6. 1, 2 or 3 halogens,
7. —$SO_n$—($C_1$-$C_6$alkyl),
8. —N(H)—S(O)$_n$—$C_1$-$C_6$alkyl,
9. —O—$C_1$-$C_6$alkyl substituents each optionally substituted with 1, 2 or 3 halogens,
10. —C(O)—N(H)—$C_3$-$C_6$cycloalkyl, or
11. —C(O)—$C_1$-$C_6$alkyl;

$R_3$ is
1. Hydrogen,
2. —$C_1$-$C_6$alkyl optionally substituted with hydroxy, —S(O)$_n$$C_1$-$C_6$alkyl, heterocycle, or 1, 2, 3, 4, 5 or 6 halogens,
3. aryl or $C_6$-$C_{12cyclo}$alkyl optionally substituted with phenyl, —$C_1$-$C_6$alkyl, —S(O)$_n$$C_1$-$C_6$alkyl, —C(O)—O—$C_1$-$C_6$alkyl, —COOH, hydroxy-$C_1$-$C_6$alkyl- or 1, 2 or 3 halogens,
4. heterocycle or optionally substituted with 1, 2 or 3 substituents independently selected from phenyl, halogen, $C_1$-$C_6$alkyl, hydroxy$C_1$-$C_6$alkyl, —COOH, —C(O)—O—$C_1$-$C_6$alkyl,
5. amino,
6. —C(O)—O—$C_1$-$C_6$alkyl,
7. —$C_1$-$C_6$alkyl-O-phenyl optionally substituted with 1, 2 or 3 halogens,
8. —$C_1$-$C_6$alkyl-phenyl optionally substituted with 1 or 2 substituents selected from hydroxy and halo,
9. —COOH,
10. Halogen,
11. —$SO_n$—($C_1$-$C_6$alkyl),
12. —N(H)—S(O)$_n$—$C_1$-$C_6$alkyl optionally substituted with 1, 2 or 3 halogen,
13. —N(H)—C(O)—$C_1$-$C_6$alkyl,
14. —N(H)-heterocycle optionally substituted with 1, 2 or 3 halogens,
15. —N(H)-aryl optionally substituted with 1, 2 or 3 halogens,
16. —N(H)—$C_1$-$C_6$alkyl optionally substituted with 1, 2 or 3 halogens,
17. —C(O)—N(H)—$C_1$-$C_6$alkyl optionally substituted with 1, 2 or 3 halogens,
18. —C(O)—NH—$C_3$-$C_6$cycloalkyl,
19. —O—$C_1$-$C_6$alkyl optionally substituted with 1, 2 or 3 halogens or phenyl optionally substituted with 1, 2, or 3 halogen;

$R_4$ is
1. H,
2. Halogen,
3. —CN
4. —$C_1$-$C_6$alkyl,
5. —O—$C_1$-$C_6$alkyl optionally substituted with 1, 2 or 3 halogens,
6. —$C_1$-$C_6$alkyl-phenyl with phenyl optionally substituted with halogen, or
7. Oxo.

Within this first aspect is the genus of compounds and pharmaceutically acceptable salts thereof, wherein
$Ar_1$ is pyridine or pyridinone or an N-oxide thereof.

Within this genus is the sub-genus of compounds and pharmaceutically acceptable salts thereof, wherein
$Ar_2$ is phenyl, oxadiazole or thiadiazole, tetrazole.

Within this sub-genus is the class of compounds and pharmaceutically acceptable salts thereof, wherein
$R_1$ is —($C_1$-$C_6$alkyl)-$SO_n$—($C_1$-$C_6$alkyl); and
$R_2$ is —$SO_n$—$C_1$-$C_6$alkyl.

Also within this first aspect, there is a genus of compounds and pharmaceutically acceptable salts thereof, wherein
$Ar_1$ is phenyl.

Within this genus there is a sub-genus of compounds and pharmaceutically acceptable salts thereof, wherein
Ar$_2$ is phenyl, oxadiazole, thiadiazole, tetrazole, pyridine or pyridinone or an N-oxide thereof.
Within this sub-genus there is a class of compounds and pharmaceutically acceptable salt thereof, wherein
R$_1$ is —(C$_1$-C$_6$alkyl)—SO$_n$—(C$_1$-C$_6$alkyl); and
R2 is —SO$_n$—C$_1$-C$_6$alkyl.
Also within the first aspect there is a genus of compounds and pharmaceutically acceptable salts thereof, wherein
Ar$_1$ is thiazole or oxazole.
Within this genus there is a sub-genus of compounds and pharmaceutically acceptable salts thereof, wherein
Ar$_2$ is phenyl, pyridine or pyridinone or an N-oxide thereof.
Within this sub-genus of compounds there is a class of compounds and pharmaceutically acceptable salts thereof, wherein
R$_1$ is —(C$_1$-C$_6$alkyl)-SO$_n$—(C$_1$-C$_6$alkyl); and
R2 is —SO$_n$—C$_1$-C$_6$alkyl.
Also within the first aspect there is a genus of compounds of Formula Ia

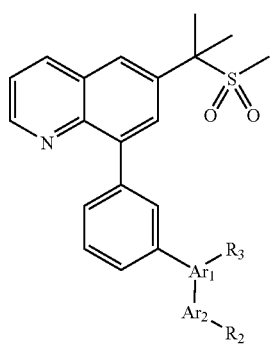

Ia and a pharmaceutically acceptable salts thereof, wherein:
Ar$_1$ is phenyl, pyridine, pyridinone, pyrimidyl, thiophene, thiazole, triazole, tetrazole, oxazole, thienodiazole, pyridodiazole, imidazothiazole or quinoxaline or an N-oxide thereof; and
Ar$_2$ is phenyl, pyridine, pyridinone, oxadiazole, tetrazole or thiadiazole or an N-oxide thereof.
Within this genus of compounds of Formula Ia there is a sub-genus of compounds and pharmaceutically acceptable salts thereof, wherein:
R$_2$ is phenyl, —COOH, —C$_1$-C$_6$alkyl, —C$_1$-C$_6$alkoxy, mono or di-halo-C$_1$-C$_6$alkoxy, -hydroxyC$_1$-C$_6$alkyl, or —SO$_n$—(C$_1$-C$_6$alkyl) or 1, 2 or 3 halogens.
Within this sub-genus there is a class of compounds of Formula Ia and pharmaceutically acceptable salt thereof, wherein:
R$_3$ is Hydrogen, amino, biphenyl, N-(tert-butoxycarbonyl)-4-phenylpyrrolidin-3-yl, N-(tert-butoxycarbonyl)azetidin-3-yl, N-(tert-butoxycarbonyl)pyrrolidin-3-yl, 3chloro-4-fluorophenyl, 4-chlorophenoxymethyl, 2-chlorophenyl, 4-chlorophenyl, ethoxycarbonyl, furan-2-yl, furan-3-yl, imidazol-2-yl, indan-1-yl, indan-2-yl, 1H-indol-2-yl, 1H-indol-3-yl, 1H-indol-4-yl, 1H-indol-5-yl, 1H-indol-6-yl, 1H-indol-7-yl, isoquinolin-1-yl, isoquinolin-4-yl, isoquinolin-5-yl, isoquinolin-8-yl, isoxazol-3-yl, 3-methoxycarbonylphenyl, 4-methoxycarbonylphenyl, methyl, 1-methyl-1Hpyrazol-3-yl, 1-methyl-1Hpyrazol-4-yl, 1-methyl-1Hpyrazol-5-yl, 2-methylphenyl, 3-methylphenyl, 4-methylphenyl, 2-methylpyridin-5-yl, methylsulfonylmethyl, 2-methylsulfonylphenyl, 3-methylsulfonylphenyl, 4-methylsulfonylphenyl, morpholin-4-ylmethyl, phenyl, pyrazinyl, 1H-pyrazol-3-yl, pyridin-2-yl, pyridin-3-yl, pyridin-4-yl, pyridin-2-yl N-oxide, pyridin-3-yl N-oxide, pyridin-4-yl N-oxide, 3-pyridinylmethyl, pyrimidin-2-yl, pyrimidin-4-yl, pyrimidin-5-yl, quinolin-4-yl, quinolin-5-yl, quinolin-8-yl, 5,6,7,8-tetrahydro-1,8-naphthyridin-2-yl, 5,6,7,8-tetrahydro-5H-benzo[a][7]annulen-5-yl, 5,6,7,8-tetrahydro-5H-benzo[a][7]annulen-6-yl, tetrahydrofuran-2-yl, 1,2,3,4-tetrahydronaphthalen-1-yl, 1,2,3,4-tetrahydronaphthalen-2-yl, 1,3-thiazol-2-yl, 1,3-thiazol-5-yl, thiophen-2-yl and thiophen-2-yl, 3-(propan-2-ol)-phenyl, 4-(propan-2-ol)-phenyl, propan-2-ol, hexafluoropropan-2-ol.

Also within the genus of compounds of Formula Ia there is the sub-genus of compounds and pharmaceutically acceptable salts thereof, wherein:
Ar$_1$ is thiazole;
Ar$_2$ is phenyl; and
R$_2$ is —SO$_2$—C$_1$-C$_6$alkyl or halogen or C$_1$-C$_6$alkyl optionally substituted with hydroxy or 1-3 halogens.
Within this sub-genus there is the class of compounds and pharmaceutically acceptable salts thereof, wherein:
R$_3$ is
1. Hydrogen,
2. —C$_1$-C$_6$alkyl optionally substituted with hydroxy, —S(O)$_n$C$_1$-C$_6$alkyl, or 1-6 halogens.
For Example, R$_3$ may be propan-2-ol, hexafluoropropan-2-ol, such that R$_3$—Ar may be 3-(propan-2-ol)-phenyl or 3-methylsulfonylphenyl.
Also within the genus of compounds of Formula Ia there is the sub-genus of compounds and pharmaceutically acceptable salts thereof, wherein
Ar$_1$ is pyridine or an N-oxide thereof;
Ar$_2$ is oxadiazole; and
R$_2$ is
1. —C$_1$-C$_6$alkyl optionally substituted with hydroxy, —S(O)$_n$C$_1$-C$_6$alkyl, or 1-3 substituents halogens,
2. —N(H)—C(O)—C$_1$-C$_6$alkyl,
3. —COOH, or
4. —C(O)—NH—C$_3$-C$_6$cycloalkyl.
Within this sub-genus of compounds of Formula Ia there is a class of compounds and pharmaceutically and acceptable salts thereof wherein:
R$_3$ is hydrogen.
Illustrating the invention are:
8-(3-{2-(3-chlorophenyl)-4-[4-(methylsulfonyl)phenyl]-1, 3-thiazol-5-yl}phenyl)-6-[1-methyl-1-(methylsulfonyl) ethyl]quinoline,
6-[1-methyl-1-(methylsulfonyl)ethyl]-8-{3-[4-[4-(methylsulfonyl)phenyl]-2-(1-oxidopyridin-4-yl)-1,3-thiazol-5-yl]phenyl}quinoline,
6-[1-methyl-1-(methylsulfonyl)ethyl]-8-{3-[4-[4-(methylsulfonyl)phenyl]-2-(1-oxidopyridin-3-yl)-1,3-thiazol-5-yl]phenyl}quinoline,
2-(3-{5-(3-{6-[1-methyl-1-(methylsulfonyl)ethyl]quinolin-8-yl}phenyl)-4-[4-(methylsulfonyl)phenyl]-1,3-thiazol-2-yl}phenyl)propan-2-ol,
3-{5-(3-{6-[1-methyl-1-(methylsulfonyl)ethyl]quinolin-8-yl}phenyl)-4-[4-(methylsulfonyl)phenyl]-1,3-thiazol-2-yl}benzoic acid,
2-{5-(3-{6-[1-methyl-1-(methylsulfonyl)ethyl]quinolin-8-yl}phenyl)-4-[4-(methylsulfonyl)phenyl]-1,3-thiazol-2-yl}propan-2-ol,
6-[1-methyl-1-(methylsulfonyl)ethyl]-8-(3-{2-(3-methyl-1,2,4-oxadiazol-5-yl)-4-[4-(methylsulfonyl)phenyl]-1,3-thiazol-5-yl}phenyl)quinoline,
6-[1-methyl-1-(methylsulfonyl)ethyl]-8-(3-{4-[4-(methylsulfonyl)phenyl]-1,3-thiazol-5-yl}phenyl)quinoline, N-cyclopropyl-5-(3-{6-[1-methyl-1-(methylsulfonyl)ethyl]quinolin-8-yl}phenyl)-4-[4-(methylsulfonyl)phenyl]-1,3-thiazole-2-carboxamide, 6-[1-methyl-1-(methylsulfonyl)ethyl]-8-(3-{2-(6-methyl-1-oxidopyridin-3-yl)-4-[4-(methylsulfonyl)phenyl]-1,3-thiazol-5-yl}phenyl)quinoline, 2-[4-(4-chlorophenyl)-5-(3-{6-[1-methyl-1-(methylsulfonyl)ethyl]quinolin-8-yl}phenyl)-1,3-thiazol-2-yl]propan-2-ol, 6-[1-methyl-1-(methylsulfonyl)ethyl]-8-(3-{2-methyl-4-[4-(methylsulfonyl)phenyl]-1,3-oxazol-5-yl}phenyl)quinoline, 2-{4-(3-{6-[1-methyl-1-(methylsulfonyl)ethyl]quinolin-8-yl}phenyl)-5-[4-(methylsulfonyl)phenyl]-1,3-thiazol-2-yl}propan-2-ol, 1,1,1-trifluoro-N-{5-(3-{6-[1-methyl-1-(methylsulfonyl)ethyl]quinolin-8-yl}phenyl)-4-[4-(methylsulfonyl)phenyl]-1,3-thiazol-2-yl}methanesulfonamide, 2-[5-(3-{6-[1-methyl-1-(methylsulfonyl)ethyl]quinolin-8-yl}phenyl)-4-pyridin-3-yl-1,3-thiazol-2-yl]propan-2-ol, 2-[5-(3-{6-[1-methyl-1-(methylsulfonyl)ethyl]quinolin-8-yl}phenyl)-4-(1-oxidopyridin-3-yl)-1,3-thiazol-2-yl]propan-2-ol, 1-(4-chlorophenyl)-1-{4-(3-{6-[1-methyl-1-(methylsulfonyl)ethyl]quinolin-8-yl}phenyl)-5-[4-(methylsulfonyl)phenyl]-1,3-thiazol-2-yl}ethanol, 6-[1-methyl-1-(methylsulfonyl)ethyl]-8-(3-{3-[4-(methylsulfonyl)phenyl]thien-2-yl}phenyl)quinoline, 1-(3"-{6-[1-methyl-1-(methylsulfonyl)ethyl]quinolin-8-yl}-1,1':2',1"-terphenyl-4-yl)ethanone, 2-(3"-{6-[1-methyl-1-(methylsulfonyl)ethyl]quinolin-8-yl}-1,1':2',1"-terphenyl-4-yl)propan-2-ol, 6-[1-methyl-1-(methylsulfonyl)ethyl]-8-{3-[5-(3-methyl-1,2,4-oxadiazol-5-yl)-1-oxidopyridin-3-yl]phenyl}quinoline, 5-(3-{6-[1-methyl-1-(methylsulfonyl)ethyl]quinolin-8-yl}phenyl)-3-(3-methyl-1,2,4-oxadiazol-5-yl)pyridin-2(1H)-one, 6-[1-methyl-1-(methylsulfonyl)ethyl]-8-(3-{6-[4-(methylsulfonyl)phenyl]imidazo[2,1-b][1,3]thiazol-5-yl}phenyl)quinoline, 6-[1-methyl-1-(methylsulfonyl)ethyl]-8-(3-{2-[4-(methylsulfonyl)phenyl]imidazo[1,2-a]pyridin-3-yl}phenyl)quinoline

[3-{6-[1-methyl-1-(methylsulfonyl)ethyl]quinolin-8-yl}-4"-(methylthio)-1,1':2',1"-terphenyl-4'-yl]methanol,

[3-{6-[1-methyl-1-(methylsulfonyl)ethyl]quinolin-8-yl}-4"-(methylsulfonyl)-1,1':2',1"-terphenyl-4'-yl]methanol, 2-[3-{6-[1-methyl-1-(methylsulfonyl)ethyl]quinolin-8-yl}-4"-(methylsulfonyl)-1,1':2',1"-terphenyl-4'-yl]propan-2-ol, 3-{6-[1-methyl-1-(methylsulfonyl)ethyl]quinolin-8-yl}-4"-(methylsulfonyl)-1,1':2',1"-terphenyl-4'-carboxylic acid, 6-[1-methyl-1-(methylsulfonyl)ethyl]-8-(3-{2-[4-(methylsulfonyl)phenyl]-1-oxidopyridin-3-yl}phenyl)quinoline, 8-{3-[3-(4-fluorophenyl)-1,2,4-oxadiazol-5-yl]phenyl}-6-[1-methyl-1-(methylsulfonyl)ethyl]quinoline, 6-[1-methyl-1-(methylsulfonyl)ethyl]-8-(3-{4-[4-(methylthio)phenyl]pyridin-3-yl}phenyl)quinoline, 3"-{6-[1-methyl-1-(methylsulfonyl)ethyl]quinolin-8-yl}-1,1':2',1"-terphenyl-4-carboxylic acid, 2-(3-{6-[1-methyl-1-(methylsulfonyl)ethyl]quinolin-8-yl}phenyl)-3-[4-(methylsulfonyl)phenyl]quinoxaline, 6-[1-methyl-1-(methylsulfonyl)ethyl]-8-(3-{3-[4-(methylsulfonyl)phenyl]pyrazin-2-yl}phenyl)quinoline, 5-(3-{6-[1-methyl-1-(methylsulfonyl)ethyl]quinolin-8-yl}phenyl)-6-[4-(methylsulfonyl)phenyl]pyridin-2(1H)-one, 1-methyl-5-(3-{6-[1-methyl-1-(methylsulfonyl)ethyl]quinolin-8-yl}phenyl)-6-[4-(methylsulfonyl)phenyl]pyridin-2(1H)-one, 8-(3-{6-methoxy-2-[4-(methylsulfonyl)phenyl]pyridin-3-yl}phenyl)-6-[1-methyl-1-(methylsulfonyl)ethyl]quinoline, 8-(3-{6-(difluoromethoxy)-2-[4-(methylsulfonyl)phenyl]pyridin-3-yl}phenyl)-6-[1-methyl-1-(methylsulfonyl)ethyl]quinoline, 8-(3-{6-[(4-fluorobenzyl)oxy]-2-[4-(methylsulfonyl)phenyl]pyridin-3-yl}phenyl)-6-[1-methyl-1-(methylsulfonyl)ethyl]quinoline, 1-(4-fluorobenzyl)-5-(3-{6-[1-methyl-1-(methylsulfonyl)ethyl]quinolin-8-yl}phenyl)-6-[4-(methylsulfonyl)phenyl]pyridin-2(1H)-one, 5-(4-fluorophenyl)-6-(3-{6-[1-methyl-1-(methylsulfonyl)ethyl]quinolin-8-yl}phenyl)pyridin-2(1H)-one, 5-(4-fluorophenyl)-1-methyl-6-(3-{6-[1-methyl-1-(methylsulfonyl)ethyl]quinolin-8-yl}phenyl)pyridin-2(1H)-one, 8-{3-[3-(4-fluorophenyl)-6-methoxypyridin-2-yl]phenyl}-6-[1-methyl-1-(methylsulfonyl)ethyl]quinoline, and pharmaceutically acceptable salts thereof.

Further illustrating the invention are the compounds of the Formula:

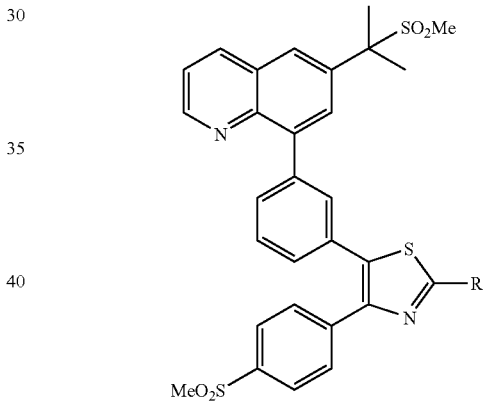

wherein

| R is selected from the group consisting of |
| --- |
| Amino |
| 2-biphenyl |
| 3-biphenyl |
| N-(tert-butoxycarbonyl)-4-phenylpyrrolidin-3-yl |
| N-(tert-butoxycarbonyl)azetidin-3-yl |
| N-(tert-butoxycarbonyl)pyrrolidin-3-yl |
| 3-chloro-4-fluorophenyl |
| 4-chlorophenoxymethyl |
| 2-chlorophenyl |
| 4-chlorophenyl |
| Ethoxycarbonyl |
| furan-2-yl |
| furan-3-yl |
| imidazol-2-yl |
| indan-1-yl |
| indan-2-yl |
| 1H-indol-2-yl |
| 1H-indol-3-yl |

-continued

| R is selected from the group consisting of |
| --- |
| 1H-indol-4-yl |
| 1H-indol-5-yl |
| 1H-indol-6-yl |
| 1H-indol-7-yl |
| Isoquinolin-1-yl |
| Isoquinolin-4-yl |
| Isoquinolin-5-yl |
| Isoquinolin-8-yl |
| isoxazol-3-yl |
| 3-methoxycarbonylphenyl |
| 4-methoxycarbonylphenyl |
| Methyl |
| 1-methyl-1H-pyrazol-3-yl |
| 1-methyl-1H-pyrazol-4-yl |
| 1-methyl-1H-pyrazol-5-yl |
| 2-methylphenyl |
| 3-methylphenyl |
| 4-methylphenyl |
| 2-methylpyridin-5-yl |
| Methylsulfonylmethyl |
| 2-methylsulfonylphenyl |
| 3-methylsulfonylphenyl |
| 4-methylsulfonylphenyl |
| morpholin-4-ylmethyl |
| Phenyl |
| Pyrazinyl |
| 1H-pyrazol-3-yl |
| pyridin-2-yl |
| pyridin-3-yl |
| pyridin-4-yl |
| 3-pyridinylmethyl |
| pyrimidin-2-yl |
| pyrimidin-4-yl |
| pyrimidin-5-yl |
| quinolin-4-yl |
| quinolin-5-yl |
| quinolin-8-yl |
| 5,6,7,8-tetrahydro-1,8-naphthyridin-2-yl |
| 6,7,8,9-tetrahydro-5H-benzo[a][7]annulen-5-yl |
| 6,7,8,9-tetrahydro-5H-benzo[a][7]annulen-6-yl |
| Tetrahydrofuran-2-yl |
| 1,2,3,4-tetrahydronaphthalen-1-yl |
| 1,2,3,4-tetrahydronaphthalen-2-yl |
| 1,3-thiazol-2-yl |
| 1,3-thiazol-5-yl |
| thiophen-2-yl |
| thiophen-3-yl |

And pharmaceutically acceptable salts thereof.

Further illustrating the invention are:

6-[1-methyl-1-(methylsulfonyl)ethyl]-8-(3-{2-[3-(methylsulfonyl)phenyl]-4-phenyl-1,3-thiazol-5-yl}phenyl)quinoline, 2-[4-(3-chlorophenyl)-5-(3-{6-[1-methyl-1-(methylsulfonyl)ethyl]quinolin-8-yl}phenyl)-1,3-thiazol-2-yl]propan-2-ol, 2-[4-(4-fluorophenyl)-5-(3-{6-[1-methyl-1-(methylsulfonyl)ethyl]quinolin-8-yl}phenyl)-1,3-thiazol-2-yl]propan-2-ol, 8-{3-[4-(4-chlorophenyl)-2-quinolin-5-yl-1,3-thiazol-5-yl]phenyl}-6-[1-methyl-1-(methylsulfonyl)ethyl]quinoline, 2-{3-[4-(3-chlorophenyl)-5-(3-{6-[1-methyl-1-(methylsulfonyl)ethyl]quinolin-8-yl}phenyl)-1,3-thiazol-2-yl]phenyl}propan-2-ol, 2-{3-[4-(3-chloro-4-fluorophenyl)-5-(3-{6-[1-methyl-1-(methylsulfonyl)ethyl]quinolin-8-yl}phenyl)-1,3-thiazol-2-yl]phenyl}propan-2-ol, 2-{3-[4-[3,4-bis(difluoromethoxy)phenyl]-5-(3-{6-[1-methyl-1-(methylsulfonyl)ethyl]quinolin-8-yl}phenyl)-1,3-thiazol-2-yl]phenyl}propan-2-ol, N-{5-(3-{6-[1-methyl-1-(methylsulfonyl)ethyl]quinolin-8-yl}phenyl)-4-[4-(methylsulfonyl)phenyl]-1,3-thiazol-2-yl}acetamide, N-{5-(3-{6-[1-methyl-1-(methylsulfonyl)ethyl]quinolin-8-yl}phenyl)-4-[4-(methylsulfonyl)phenyl]-1,3-thiazol-2-yl}pyridin-4-amine, 2-[5-(3-{6-[1-methyl-1-(methylsulfonyl)ethyl]quinolin-8-yl}phenyl)-4-pyridin-4-yl-1,3-thiazol-2-yl]propan-2-ol, 2-[5-(3-{6-[1-methyl-1-(methylsulfonyl)ethyl]quinolin-8-yl}phenyl)-4-(1-oxidopyridin-4-yl)-1,3-thiazol-2-yl]propan-2-ol, 2-[5-(4-chlorophenyl)-4-(3-{6-[1-methyl-1-(methylsulfonyl)ethyl]quinolin-8-yl}phenyl)-1,3-thiazol-2-yl]propan-2-ol, 2-{3-[4-(4-chlorophenyl)-5-(3-{6-[1-methyl-1-(methylsulfonyl)ethyl]quinolin-8-yl}phenyl)-1,3-thiazol-2-yl]phenyl}propan-2-ol, and 6-[1-methyl-1-(methylsulfonyl)ethyl]-8-{3-[5-(1H-tetraazol-5-yl)pyridin-3-yl]phenyl}quinoline, and pharmaceutically acceptable salts thereof.

Further illustrating the invention are:

6-[1-methyl-1-(methylsulfonyl)ethyl]-8-(3-{5-[4-(methylsulfonyl)phenyl]-1-oxidopyridin-3-yl}phenyl)quinoline, 6-[1-methyl-1-(methylsulfonyl)ethyl]-8-(3-{5-[3-(methylsulfonyl)phenyl]-1-oxidopyridin-3-yl}phenyl)quinoline, 6-[1-methyl-1-(methylsulfonyl)ethyl]-8-(3-{5-[2-(methylsulfonyl)phenyl]-1-oxidopyridin-3-yl}phenyl)quinoline, 6-[1-methyl-1-(methylsulfonyl)ethyl]-8-(3-{2-[4-(methylsulfonyl)phenyl]pyridin-3-yl}phenyl)quinoline, 6-[1-methyl-1-(methylsulfonyl)ethyl]-8-[3-(1-oxido-5-phenylpyridin-3-yl)phenyl]quinoline, 8-{3-[5-(3,5-dichlorophenyl)-1-oxidopyridin-3-yl]phenyl}-6-[1-methyl-1-(methylsulfonyl)ethyl]quinoline, 8-{3-[5-(3,4-dimethoxyphenyl)-1-oxidopyridin-3-yl]phenyl}-6-[1-methyl-1-(methylsulfonyl)ethyl]quinoline, 6-[1-methyl-1-(methylsulfonyl)ethyl]-8-{3-[5-(5-methyl-1,2,4-oxadiazol-3-yl)-1-oxidopyridin-3-yl]phenyl}quinoline, 6-[1-methyl-1-(methylsulfonyl)ethyl]-8-{3-[5-(5-methyl-1,3,4-oxadiazol-2-yl)-1-oxidopyridin-3-yl]phenyl}quinoline, 8-{3-[6-(benzyloxy)-5-(3-methyl-1,2,4-oxadiazol-5-yl)pyridin-3-yl]phenyl}-6-[1-methyl-1-(methylsulfonyl)ethyl]quinoline, 6-[1-methyl-1-(methylsulfonyl)ethyl]-8-(3-{6-[4-(methylsulfonyl)phenyl]-1-oxidopyridin-3-yl}phenyl)quinoline, 6-[1-methyl-1-(methylsulfonyl)ethyl]-8-(3-{5-[4-(methylsulfonyl)phenyl]-1-oxidopyridin-2-yl}phenyl)quinoline, 6-[1-methyl-1-(methylsulfonyl)ethyl]-8-{3-[3-[4-(methylsulfonyl)phenyl]-5-(trifluoromethyl)pyridin-2-yl]phenyl}quinoline, 1-(4-chlorophenyl)-3-(3-{6-[1-methyl-1-(methylsulfonyl)ethyl]quinolin-8-yl}phenyl)pyridin-2(1H)-one, N-isopropyl-5-(3-{6-[1-methyl-1-(methylsulfonyl)ethyl]quinolin-8-yl}phenyl)-4-[4-(methylsulfonyl)phenyl]thiophene-2-carboxamide, 6-[1-methyl-1-(methylsulfonyl)ethyl]-8-(1,1':2',1"-terphenyl-3-yl)quinoline, 6-[1-methyl-1-(methylsulfonyl)ethyl]-8-[4"-(methylthio)-1,1':2',1"-terphenyl-3-yl]quinoline, 6-[1-methyl-1-(methylsulfonyl)ethyl]-8-[2'-(5-methyl-1,3,4-oxadiazol-2-yl)-1,1'-biphenyl-3-yl]quinoline, methyl 3-{6-[1-methyl-1-(methylsulfonyl)ethyl]quinolin-8-yl]-4"-(methylsulfonyl)-1,1':2',1"-terphenyl-4'-carboxylate, 6-[1-methyl-1-(methylsulfonyl)ethyl]-8-(1,1':4',1"-terphenyl-3-yl)quinoline, 6-[1-methyl-1-(methylsulfonyl)ethyl]-8-(1,1':3',1"-terphenyl-3-yl)quinoline,
2-[5-(3'-{6-[1-methyl-1-(methylsulfonyl)ethyl]quinolin-8-yl}-1,1'-biphenyl-2-yl)-1,3-thiazol-2-yl]propan-2-ol,
6-[1-methyl-1-(methylsulfonyl)ethyl]-8-[3'-(1-oxidopyridin-4-yl)-1,1'-biphenyl-3-yl]quinoline,
and pharmaceutically acceptable salts thereof.
Further illustrating the invention are:
6-[1-methyl-1-(methylsulfonyl)ethyl]-8-(3-{4-[4-(methylsulfonyl)phenyl]pyridin-3-yl}phenyl)quinoline,
6-[1-methyl-1-(methylsulfonyl)ethyl]-8-(3-{4-[4-(methylsulfonyl)phenyl]-1-oxidopyridin-3-yl}phenyl)quinoline,
6-[1-methyl-1-(methylsulfonyl)ethyl]-8-(3-{4-[3-(methylthio)phenyl]pyridin-3-yl}phenyl)quinoline,
8-[4',5'-difluoro-4"-(methylthio)-1,1':2',1"-terphenyl-3-yl]-6-[1-methyl-1-(methylsulfonyl)ethyl]quinoline,
8-[4',5'-difluoro-4"-(methylsulfonyl)-1,1':2',1"-terphenyl-3-yl]-6-[1-methyl-1-(methylsulfonyl)ethyl]quinoline,
8-(4"-fluoro-1,1':2',1"-terphenyl-3-yl)-6-[1-methyl-1-(methylsulfonyl)ethyl]quinoline,
6,7-dichloro-2-(3-{6-[1-methyl-1-(methylsulfonyl)ethyl]quinolin-8-yl}phenyl)-3-[4-(methylsulfonyl)phenyl]quinoxaline,
2-(4-chlorophenyl)-3-(3-{6-[1-methyl-1-(methylsulfonyl)ethyl]quinolin-8-yl}phenyl)quinoxaline,
2-{4-[3-(3-{6-[1-methyl-1-(methylsulfonyl)ethyl]quinolin-8-yl}phenyl)quinoxalin-2-yl]phenyl}propan-2-ol,
2-[3,4-bis(difluoromethoxy)phenyl]-3-(3-{6-[1-methyl-1-(methylsulfonyl)ethyl]quinolin-8-yl}phenyl)quinoxaline,
4-[3-(3-{6-[1-methyl-1-(methylsulfonyl)ethyl]quinolin-8-yl}phenyl)quinoxalin-2-yl]benzoic acid,
N-cyclopropyl-4-[3-(3-{6-[1-methyl-1-(methylsulfonyl)ethyl]quinolin-8-yl}phenyl)quinoxalin-2-yl]benzamide,
2-(3-{6-[1-methyl-1-(methylsulfonyl)ethyl]quinolin-8-yl}phenyl)-3-(4-methylphenyl)quinoxaline,
2-(3-{6-[1-methyl-1-(methylsulfonyl)ethyl]quinolin-8-yl}phenyl)-3-phenylquinoxaline,
2-(4-fluorophenyl)-3-(3-{6-[1-methyl-1-(methylsulfonyl)ethyl]quinolin-8-yl}phenyl)quinoxaline,
2-{4-[3-(3-{6-[1-methyl-1-(methylsulfonyl)ethyl]quinolin-8-yl}phenyl)pyrazin-2-yl]phenyl}propan-2-ol,
6-[1-methyl-1-(methylsulfonyl)ethyl]-8-(3-{3-[4-(methylthio)phenyl]pyrazin-2-yl}phenyl)quinoline,
8-{3-[3-(4-fluorophenyl)pyrazin-2-yl]phenyl}-6-[1-methyl-1-(methylsulfonyl)ethyl]quinoline,
8-(3-{2-(2-ethylpyridin-4-yl)-4-[4-(methylsulfonyl)phenyl]-1,3-thiazol-5-yl}phenyl)-6-[1-methyl-1-(methylsulfonyl)ethyl]quinoline,
2-(4-{5-(3-{6-[1-methyl-1-(methylsulfonyl)ethyl]quinolin-8-yl}phenyl)-4-[4-(methylsulfonyl)phenyl]-1,3-thiazol-2-yl}phenyl)propan-2-ol,
and pharmaceutically acceptable salts thereof.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalenyl, adamantanyl, indanyl, indenyl, fluorenyl, 1,2,3,4-tetrahydronaphthalenyl and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "cycloalkyloxy" unless specifically stated otherwise includes a cycloalkyl group connected to the oxy connecting atom.

The term "alkoxy" unless specifically stated otherwise includes an alkyl group connected to the oxy connecting atom.

The term "aryl" unless specifically stated otherwise includes multiple fused ring systems as well as single ring systems such as, for example, phenyl or naphthyl. In the case of single rings "aryl" shall include only aromatic carbocycles. In the case of multiple rings fused together, "aryl" shall include carbocycles where at least one of the rings is an aromatic carbocycle such as in indanyl, 1,2,3,4-tetrahydronaphthalene and 6,7,8,9-tertrhydro-5H-benzo[a]annulenenyl.

The term "aryloxy" unless specifically stated otherwise includes multiple fused ring systems as mentioned above as well as single ring systems such as, for example, phenyl or naphthyl, connected through the oxy connecting atom to the connecting site.

The term "$C_0$-$C_6$alkyl" includes alkyls containing 6, 5, 4, 3, 2, 1, or no carbon atoms. An alkyl with no carbon atoms is a hydrogen atom substituent when the alkyl is a terminus moiety. An alkyl with no carbon atoms is a direct bond when the alkyl is a bridging moiety.

The term "heterocyclo" unless specifically stated otherwise includes one or more O, S, or N atoms. For example, heterocycles include ring systems that contain one or more O, S, or N atoms in the ring, including mixtures of such atoms. The heteroatoms replace ring carbon atoms. Thus, for example, a heterocyclo of 5 ring members is a five membered ring containing from zero to 4 carbon atoms. Moreover, for purposes of this specification, heterocycles includes rings substituted with "oxo", such as pyridin-2-one.

Examples of heterocycles include, for example, pyridinyl, pyridin-one-yl, quinolinyl, isoquinolinyl, pyridazinyl, pyrimidinyl, pyrazinyl, quinoxalinyl, furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl.

The term "heterocyclooxy" unless specifically stated otherwise describes a heterocyclo group connected through an oxy connecting atom to the connecting site.

Examples of heterocyclo($C_{1-6}$)alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

Other examples of heterocyclo$C_{3-7}$alkyl include, for example, azetidinyl, pyrrolidinyl, piperidinyl, perhydroazepinyl, piperazinyl, morpholinyl, tetrahydrofuranyl, imidazolinyl, pyrolidin-2-one, piperidin-2-one, and thiomorpholinyl.

The term "N-heterocycloC$_{4-7}$alkyl" describes nonaryl heterocyclic compounds having 3-6 carbon atoms and one nitrogen atom forming the ring. Examples include azetidinyl, pyrrolidinyl, piperidinyl, and perhydroazepinyl.

Examples of aryl(C$_{1-6}$)alkyl include, for example, phenyl (C$_{1-6}$)alkyl, and naphthyl(C$_{1-6}$)alkyl.

Examples of heterocycloC$_{3-7}$alkylcarbonyl(C$_{1-6}$)alkyl include, for example, azetidinyl carbonyl(C$_{1-6}$)alkyl, pyrrolidinyl carbonyl(C$_{1-6}$)alkyl, piperidinyl carbonyl(C$_{1-6}$)alkyl, piperazinyl carbonyl(C$_{1-6}$)alkyl, morpholinyl carbonyl(C$_{1-6}$)alkyl, and thiomorpholinyl carbonyl(C$_{1-6}$)alkyl.

The term "amine" unless specifically stated otherwise includes primary, secondary and tertiary amines.

Unless otherwise stated, the term "carbamoyl" is used to include —NHC(O)OC$_1$-C$_4$alkyl, and —OC(O)NHC$_1$-C$_4$alkyl.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, the substitution can be made at any of the groups. For example, substituted aryl(C$_{1-6}$)alkyl includes substitution on the aryl group as well as substitution on the alkyl group.

The term "oxide" of heteroaryl groups is used in the ordinary well-known chemical sense and include, for example, N-oxides of nitrogen heteroatoms.

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be mixtures of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are benzenesulfonic, citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) Leukotriene receptor antagonists, ii) Leukotriene biosynthesis inhibitors, iii) corticosteroids, iv) H1 receptor antagonists, v) beta 2 adrenoceptor agonists, vi) COX-2 selective inhibitors, vii) statins, viii) non-steroidal anti-inflammatory drugs ("NSAID"), and ix) M2/M3 antagonists. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.01 mg/kg to about 140 mg/kg of body weight per day are useful in the treatment of conditions such as asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, chronic glomerulonephritis, atopic dermatitis, urticaria, adult respiratory distress syndrome, chronic obstructive pulmonary disease in animals, diabetes insipidus, allergic rhinitis, allergic conjunctivitis, vernal conjunctivitis, arterial restenosis, ortherosclerosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, tumour growth and cancerous invasion of normal tissues which are responsive to PDE4 inhibition, or alternatively about 0.5 mg to about 7 g per patient per day. For example, inflammation may be effectively treated by the administration of from about 0.01 mg to 50 mg of the compound per kilogram of body weight per day, or alternatively about 0.5 mg to about 3.5 g per patient per day. Further, it is understood that the PDE4 inhibiting compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 500 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula L or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients- such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and pharmaceutical compositions of this invention have been found to exhibit biological activity as PDE4 inhibitors. Accordingly, another aspect of the invention is the treatment in mammals of, for example, asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, celiac sprue, ulcerative colitis, Crohn's disease, reperfusion injury of the myocardium and brain, inflammatory arthritis, chronic glomerulonephritis, atopic dermatitis, urticaria, adult respiratory distress syndrome, chronic obstructive pulmonary disease in animals, diabetes insipidus, allergic rhinitis, allergic conjunctivitis, vernal conjunctivitis, arterial restenosis, ortherosclerosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, tumour growth and cancerous invasion of normal tissues—maladies that are amenable to amelioration through inhibition of the PDE4 isoenzyme and the resulting elevated cCAMP levels—by the administration of an effective amount of the compounds of this invention.

In addition to being useful in the treatment of cognitive deficit (such as memory impairment, mentioned elsewhere in this specification) due to psycological dysfunction, neurological deficit (such as stroke) or psychiatric dysfunction, the compounds of the invention are useful for enhancing cognition in a healthy subject (enhancing memory, learning, retention, recall, awareness and judgement).

The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

Further, as described above, the compound of this invention can be utilized in combination with other therapeutic compounds. In particular, the combinations of the PDE4 inhibiting compound of this invention can be advantageously used in combination with i) Leukotriene receptor antagonists, ii) Leukotriene biosynthesis inhibitors, iii) corticosteroids, iv) H1 receptor antagonists, v) beta 2 adrenoceptor agonists, vi) COX-2 selective inhibitors, vii) statins, viii) non-steroidal anti-inflammatory drugs ("NSAID"), and ix) M2/M3 antagonists.

The abbreviations used herein have the following tabulated meanings. Abbreviations not tabulated below have their meanings as commonly used unless specifically stated otherwise.

| | |
|---|---|
| Ac = | acetyl |
| Bn = | benzyl |
| CAMP | cyclic adenosine-3',5'-monophosphate |
| DBU = | 1,8-diazabicyclo[5.4.0]undec-7-ene |
| DIBAL = | diisobutylaluminum hydride |
| DMAP = | 4-(dimethylamino)pyridine |
| DMF = | N,N-dimethylformamide |
| Et$_3$N = | triethylamine |
| GST | glutathione transferase |
| HMDS | hexamethyldisilazide |
| LDA = | lithium diisopropylamide |
| m-CPBA = | metachloroperbenzoic acid |
| MMPP = | monoperoxyphthalic acid |
| MPPM = | monoperoxyphthalic acid, magnesium salt 6H$_2$O |
| Ms = | methanesulfonyl = mesyl = SO$_2$Me |
| Ms0 = | methanesulfonate = mesylate |

| | |
|---|---|
| NSAID = | non-steroidal anti-inflammatory drug |
| o-Tol = | ortho-tolyl |
| OXONE ® = | 2KHSO$_5$•KHSO$_4$•K$_2$SO$_4$ |
| PCC = | pyridinium chlorochromate |
| PDC = | pyridinium dichromate |
| PDE | phosphodiesterase |
| Ph = | phenyl |
| Phe = | benzenediyl |
| PMB = | para-methoxybenzyl |
| Pye = | pyridinediyl |
| r.t. = | room temperature |
| Rac. = | racemic |
| SAM = | aminosulfonyl or sulfonamide or SO$_2$NH$_2$ |
| SEM = | 2-(trimethylsilyl)ethoxymethoxy |
| SPA = | scintillation proximity assay |
| TBAF = | tetra-n-butylammonium fluoride |
| Th = | 2- or 3-thienyl |
| TFA = | trifluoroacetic acid |
| TFAA = | trifluoroacetic acid anhydride |
| THF = | tetrahydrofuran |
| Thi = | thiophenediyl |
| TLC = | thin layer chromatography |
| TMS-CN = | trimethylsilyl cyanide |
| TMSI | trimethylsilyl iodide |
| Tz = | 1H (or 2H)-tetrazol-5-yl |
| C$_3$H$_5$ = | allyl |

Alkyl Group Abbreviations

| | |
|---|---|
| Me = | Methyl |
| Et = | Ethyl |
| n-Pr = | Normal propyl |
| i-Pr = | Isopropyl |
| n-Bu = | Normal butyl |
| i-Bu = | Isobutyl |
| s-Bu = | Secondary butyl |
| t-Bu = | Tertiary butyl |
| c-Pr = | Cyclopropyl |
| c-Bu = | Cyclobutyl |
| c-Pen = | Cyclopentyl |
| c-Hex = | Cyclohexyl |

ASSAYS DEMONSTRATING BIOLOGICAL ACTIVITY

LPS and FMLP-Induced TNF-α and LTB$_4$ Assays in Human Whole Blood

Whole blood provides a protein and cell-rich milieu appropriate for the study of biochemical efficacy of anti-inflammatory compounds such as PDE4-selective inhibitors. Normal non-stimulated human blood does not contain detectable levels of TNF-α and LTB$_4$. Upon stimulation with LPS, activated monocytes express and secrete TNF-α up to 8 hours and plasma levels remain stable for 24 hours. Published studies have shown that inhibition of TNF-α by increasing intracellular cAMP via PDE4 inhibition and/or enhanced adenylyl cyclase activity occurs at the transcriptional level. LTB$_4$ synthesis is also sensitive to levels of intracellular cAMP and can be completely inhibited by PDE4-selective inhibitors. As there is little LTB$_4$ produced during a 24 hour LPS stimulation of whole blood, an additional LPS stimulation followed by fMLP challenge of human whole blood is necessary for LTB$_4$ synthesis by activated neutrophils. Thus, by using the same blood sample, it is possible to evaluate the potency of a compound on two surrogate markers of PDE4 activity in the whole blood by the following procedure.

Fresh blood was collected in heparinized tubes by venipuncture from healthy human volunteers (male and female). These subjects had no apparent inflammatory conditions and had not taken any NSAIDs for at least 4 days prior to blood collection. 500 μL aliquots of blood were pre-incubated with either 2 μL of vehicle (DMSO) or 2 μL of test compound at varying concentrations for 15 minutes at 37° C. This was followed by the addition of either 10 μL vehicle (PBS) as blanks or 10 μL LPS (1 μg/mL final concentration, #L-2630 (Sigma Chemical Co., St. Louis, Mo.) from E. coli, serotype 0111:B4; diluted in 0.1% w/v BSA (in PBS)). After 24 hours of incubation at 37° C., another 10 μL of PBS (blank) or 10 μL of LPS (1 μg/mL final concentration) was added to blood and incubated for 30 minutes at 37° C. The blood was then challenged with either 10 μL of PBS (blank) or 10 μL of FMP (1 μM final concentration, #F-3506 (Sigma); diluted in 1% w/v BSA (in PBS)) for 15 minutes at 37° C. The blood samples were centrifuged at 1500×g for 10 minutes at 4° C. to obtain plasma. A 50 μL aliquot of plasma was mixed with 200 μL methanol for protein precipitation and centrifuged as above. The supernatant was assayed for $LTB_4$ using an enzyme immunoassay kit (#520111 from Cayman Chemical Co., Ann Arbor, Mich.) according to the manufacturer's procedure. TNF-α was assayed in diluted plasma (in PBS) using an ELISA kit (Cistron Biotechnology, Pine Brook, N.J.) according to manufacturer's procedure. The $IC_{50}$ values of selected examples:

| Example: | IC50 (μM) |
|---|---|
| 115 | 0.61 |
| 167 | 0.139 |
| 1 | 0.155 |
| 19 | 0.046 |
| 24 | 0.054 |
| 41 | 0.044 |
| 69 | 0.025 |
| 78 | 0.12 |
| 82 | 0.156 |
| 88 | 0.144 |
| 94 | 1.04 |
| 100 | 0.220 |
| 157 | 0.136 |

Anti-Allergic Activity In Vivo

Compounds of the invention have been tested for effects on an IgE-mediated allergic pulmonary inflammation induced by inhalation of antigen by sensitized guinea pigs. Guinea pigs were initially sensitized to ovalbumin under mild cyclophosphamide-induced immunosuppression, by intraperitoneal injection of antigen in combinations with aluminum hydroxide and pertussis vaccine. Booster doses of antigen were given two and four weeks later. At six weeks, animals were challenged with aerosolized ovalbumin while under cover of an intraperitoneally administered anti-histamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the Examples (0.001-10 mg/kg i.p. or p.o.), up to three times during the 48 h following antigen challenge, lead to a significant reduction in the eosinophilia and the accumulation of other inflammatory leukocytes. There was also less inflammatory damage in the lungs of animals treated with compounds of the Examples.

Spa Based PDE Activity Assay Protocol

Compounds which inhibit the hydrolysis of cAMP to AMP by the type-IV cAMP-specific phosphodiesterases were screened in a 96-well plate format as follows:

In a 96 well-plate at 30° C. was added the test compound (dissolved in 2 μL DMSO), 188 mL of substrate buffer containing [2,8-$^3$H] adenosine 3',5'-cyclic phosphate (cAMP, 100 nM to 50 μM), 10 mM $MgCl_2$, 1 mM EDTA, 50 mM Tris, pH 7.5. The reaction was initiated by the addition of 10 mL of human recombinant PDE4 (the amount was controlled so that ~10% product was formed in 10 min.). The reaction was stopped after 10 min. by the addition of 1 mg of PDE-SPA beads (Amersham Pharmacia Biotech, Inc., Piscataway, N.J.). The product AMP generated was quantified on a Wallac Microbeta® 96-well plate counter (EG&G Wallac Co., Gaithersburg, Md.). The signal in the absence of enzyme was defined as the background. 100% activity was defined as the signal detected in the presence of enzyme and DMSO with the background subtracted. Percentage of inhibition was calculated accordingly. $IC_{50}$ value was approximated with a non-linear regression fit using the standard 4-parameter/multiple binding sites equation from a ten point titration.

The $IC_{50}$ values of Examples in table below were determined with 100 nM cAMP using the purified GST fusion protein of the human recombinant phosphodiesterase IVa (met-248) produced from a baculovirus/Sf-9 expression system. The $IC_{50}$ values of selected examples:

| Example: | IC50 (nM) |
|---|---|
| 115 | 2.2 |
| 167 | 0.4 |
| 1 | 0.3 |
| 19 | 1.0 |
| 24 | 0.4 |
| 41 | 1.0 |
| 69 | 0.6 |
| 78 | 0.4 |
| 82 | 3.1 |
| 88 | 1.6 |
| 94 | 4.3 |
| 100 | 4.1 |
| 157 | 1.7 |

The examples that follow are intended as an illustration of certain preferred embodiments of the invention and no limitation of the invention is implied.

Unless specifically stated otherwise, the experimental procedures were performed under the following conditions. All operations were carried out at room or ambient temperature—that is, at a temperature in the range of 18-25° C. Evaporation of solvent was carried out using a rotary evaporator under reduced pressure (600-4000 pascals: 4.5-30 mm. Hg) with a bath temperature of up to 60° C. The course of reactions was followed by thin layer chromatography (TLC) and reaction times are given for illustration only. Melting points are uncorrected and 'd' indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. Yields are given for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. broad; etc. In addition, "Ar" signifies an aromatic signal.

Chemical symbols have their usual meanings; the following abbreviations have also been used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Methods of Synthesis

Compounds of the present invention can be prepared according to the following methods. The substituents are the same as in Formula I except where defined otherwise.

Methods of Synthesis

Compounds of the present invention can be prepared according to the following general methods. Reactions are typically run under nitrogen atmosphere at ambient temperature if not otherwise mention. Anhydrous solvent such as THF, DMF, Et$_2$O, DME and Toluene are commercial grade. Reagents are commercial grade and were used without any purification. Flash chromatography is run on silica gel (230-400 mesh).

All 8-aryl-quinoline of the type I can be prepared (Scheme 1 and 2) using a Suzuki type coupling to build the biaryl moieties. In a typical Suzuki coupling reaction, all reagents except for the palladium catalyst are mixed in the appropriate solvent. The mixture is then degassed by refluxing for 15 min under nitrogen atmosphere then cooling to ambient temperature or by applying two to three vacuum/nitrogen sequence. The palladium catalyst is then added and the reaction mixture is stirred at the appropriate temperature until completion as monitored by TLC.

The substituents are the same as in Formula I except where defined otherwise. Compounds of the type I (Scheme 1) can be prepared in a two step one-pot manner by generating in-situ the boronate analog of 8-bromo quinoline II followed by a palladium catalyzed coupling with the appropriate biaryl III

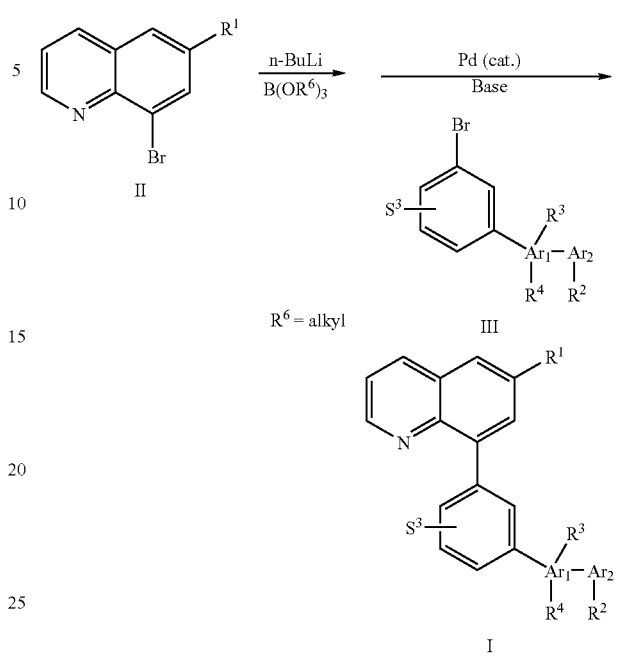

In most cases, compounds were prepared by the two procedures described in Scheme 2. A Suzuki type coupling between the 8-bromo-quinoline II and the bromo-phenyl-boronic acid IV produced to the common intermediate V. The latter can be coupled with either an aryl-stannane of type VI or a boronic acid of type VII to generate the desired compound I. Alternatively, the arylbromide V can be converted to the corresponding pinacole boronate VIII by a PdCl$_2$(dppf)$_2$ catalyzed coupling reaction with pinacole diborane. Subsequently, a Suzuki coupling of the boronate VIII with the appropriate heteroaryl halide or O-triflate IX will generate the desired compound I.

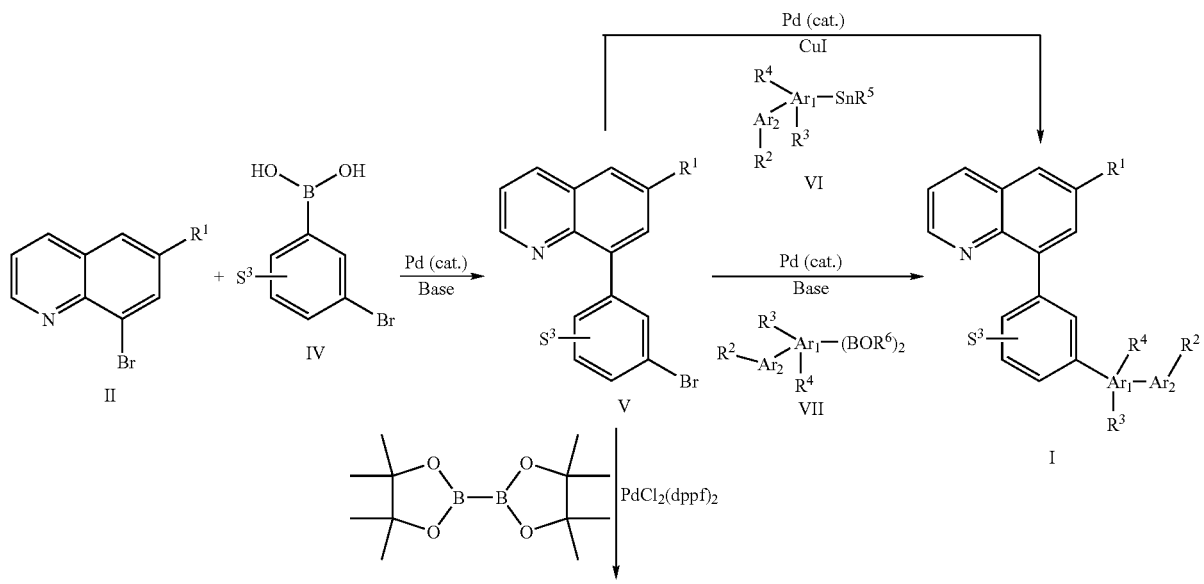

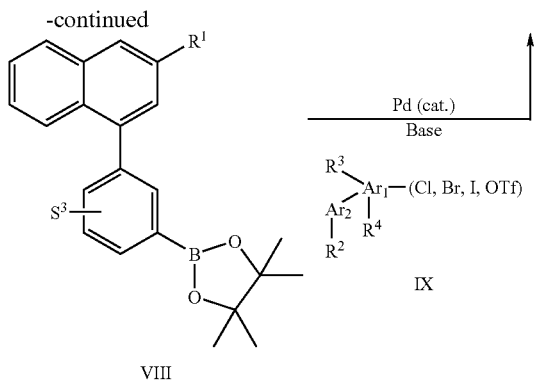

$R^5$ = alkyl
$R^6$ = alkyl

Boronic acid of the type XII can be prepared (Scheme 3) by lithium-halogen exchange at low temperature in THF or Et$_2$O on the corresponding heteroaryl bromide X followed by the addition of a trialkyl-boronate (B(OR)$_3$). Hydrolysis, under acidic condition, of the resulting heteroaryl-boronate will generate the desired boronic acid XII (R=H). Likewise, lithium-halogen exchange or deprotonation at low temperature in THF or Et$_2$O followed by the addition of a trialkyl-stannyl-chloride (R$_3$SnCl) generates the stannane of type XI. These can be used as precursors for biaryl of type IX.

described by M. Journet et al. in Tetrahedron Lett. 39, 1717 (1998). They can serve as precursor for pyridinone XVII and XVIII using ammonia and methyl propiolate as described for example in J. Heterocyclic Chem. 30, 1129 (1993). The ethanone XV or ethanone XVI can also be lead to alpha bromo analogs XIX and XX which are used for the formation of thiazole, oxazole XXI, XXII and other heterocycle like quinoxaline XXIII, imidazothiazole XXIV or imidazopyridinyl XXV.

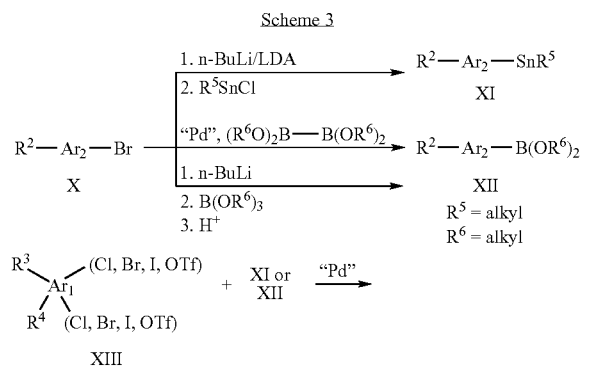

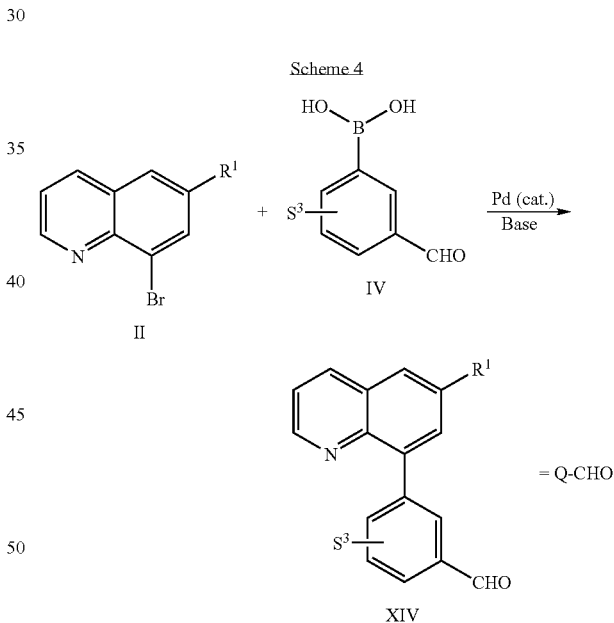

The heterocyclic Ar$_1$ groups can be constructed from the common aldehyde XIV or Q-CHO (scheme 4) prepared by Suzuki type coupling. The aldehyde XIV can lead to ethanone XV or ethanone XVI (scheme 5) by using a methodology

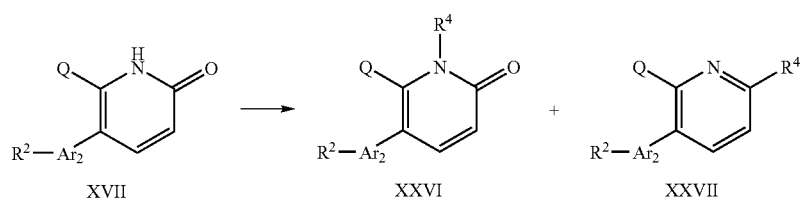

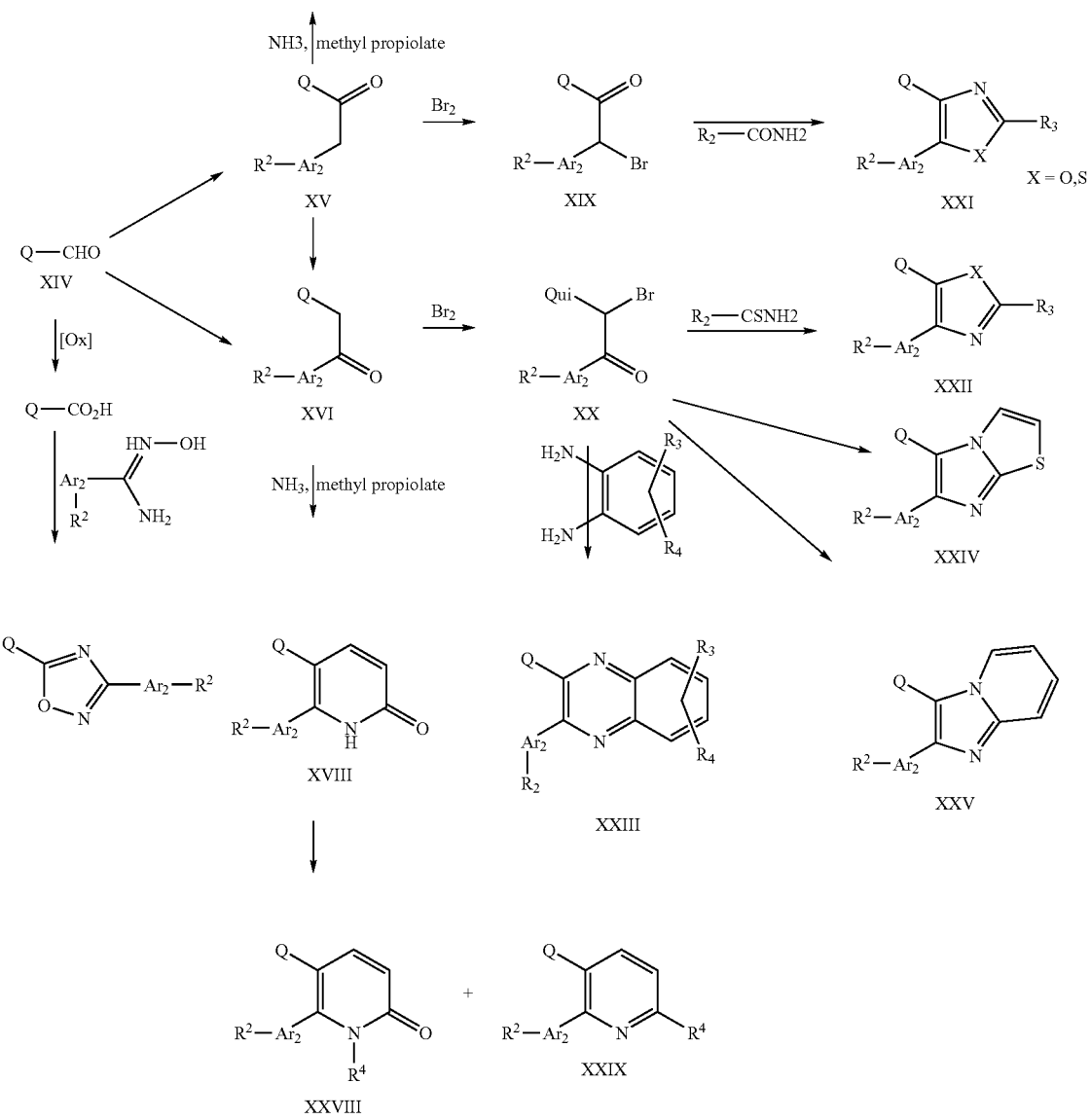

8-Bromoquinoline II with various substituent at position 6 can be prepared by the Skraup synthesis (Org. React. 7, 59-98, 1953) using an appropiate aniline, an oxidizing agent such as 3-nitrophenylsulfonic acid and glycerol in strong acidic media such as sulfuric acid or methanesulfonic acid (Scheme 6).

Scheme 6

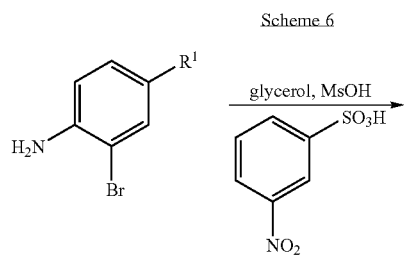

-continued

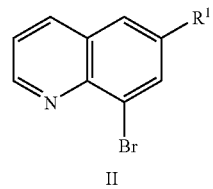

The common quinoline intermediates were prepared using the following procedures.

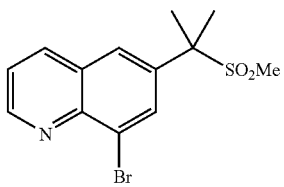

Quinoline_1

8-Bromo-6-(1-methanesulfonyl-1-methyl-ethyl)-quinoline

Preparation of 8-Bromo-6-(1-methanesulfonyl-1-methyl-ethyl)-quinoline is described in Patent Publication U.S. Pat. No. 6,410,563 B1 (2002).

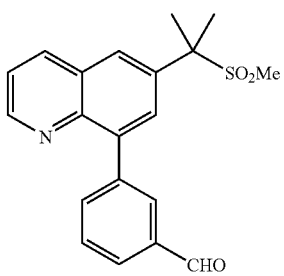

Quinoline_2

3-{3-[1-methyl-1-(methylsulfonyl)ethyl]-1-naphthyl}benzaldehyde

Preparation of 3-{3-[1-methyl-1-(methylsulfonyl)ethyl]-1-naphthyl}benzaldehyde is described in Patent Publication U.S. Pat. No. 6,410,563 B1 (2002).

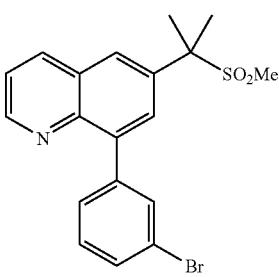

Quinoline_3

8-(3-Bromo-phenyl)-6-(1-methanesulfonyl-1-methyl-ethyl)-quinoline

A mixture of Quinoline 2 (1.0 eq), 3-bromophenylboronic acid (1.05 eq), $Na_2CO_3$ (2 M in $H_2O$; 3.6 eq) and $Pd(PPh_3)_4$ (0.03 eq) in DME (0.2 M) was stirred at 80° C. for 8 h. The resulting mixture was cooled to room temperature and diluted with water under vigorous stirring. The resulting precipitate was filtered and dried. Flash chromatography (Hex:EtOAc; 2:3) and stirring in a mixture of $Et_2O$ and $CH_2Cl_2$ (10:1) yielded the title compound as a light yellow solid after filtration.

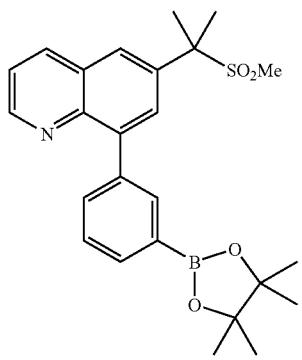

Quinoline_4

6-(1-Methanesulfonyl-1-methyl-ethyl)-8-[3-(4,4,5,5-tetramethyl-[1,3,2]dioxaborolan-2-yl)-phenyl]-quinoline A mixture of Quinoline_3 (1.0 eq), pinacole diborane ester(1.4 eq) and KOAc (3.5 eq) and $PdCl_2(dppf)_2$ (0.03 eq) in DMF (0.14 M) was stirred at 60° C. for 24 h. An extra amount of pinacole diborane (0.3 eq), KOAc (1.05 eq) and $PdCl_2$ $(dppf)_2$ (0.01 eq) were added and the mixture was stirred at 60° C. for 24 h. The resulting mixture was cooled to room temperature, diluted with $EtOAc:Et_2O$ (1:1). The organic phase was washed with water (3×), brine, dried over $MgSO_4$, filtered and concentrated. Flash chromatography ($CH_2Cl_2$:EtOAc; 9:1) and stirring in $Et_2O$:EtOAc (10:1) afforded the title compound as a white solid. Subsequent flash chromatography ($CH_2Cl_2$:EtOAc; 9:1) on the mother liquor and stirring in $Et_2O$:EtOAc (10:1) afforded a second crop of the title compound containing 5% of starting material.

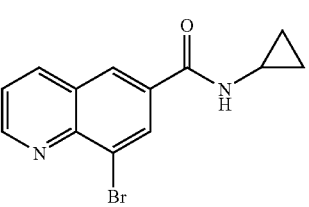

Quinoline_5

8-bromo-N-cyclopropylquinoline-6-carboxamide

Step 1: 8-bromoquinoline-6-carboxylic Acid

4-Amino-3-bromo-benzoic acid (1 eq) and glycerol (2.4 eq) was added to sulfuric acid (6.4M, reaction conc. 0.6M) at 0° C. After 15 min, the bath was removed and 3-nitro-phenylsulfonic acid sodium salt (1.3 eq) was added portionwise. The reaction mixture was heated gradually until exothermic reaction started (between 110-140° C.), the internal temperature was maintained below 170° C. for 1 h. The reaction mixture was cooled to 50° C. and poured slowly into $NH_4OH$-ice (2:1). The title product isolated by filtration, dissolved in warm 5% $NH_4OH$/MeOH and diluted with $CH_2Cl_2$. This solution was filtered through silica gel eluting with ($NH_4OH$, MeOH, CH$_2$Cl$_2$, 3:30:70). The residue was stirred in EtOH and the title product isolated by filtration.

Step 2:
8-bromo-N-cyclopropylquinoline-6-carboxamide

A solution of HATU (1.2 eq), 8-bromoquinoline-6-carboxylic acid (1 eq), diisopropylethylamine (2.5 eq) and cyclopropylamine (1.1 eq) was stirred at rt for 1 h in DMF (0.2 M). The reaction mixture was diluted with water, stirred for 2 h and extracted with EtOAc. The organic extracts were washed with brine, dried over MgSO$_4$, filtered and concentrated. The residue was crystallized in EtOAc and title product isolated by filtration as a white powder.

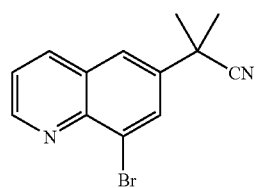

Quinoline_6

2-(8-bromoquinolin-6-yl)-2-methylpropanenitrile

Preparation of 2-(8-bromoquinolin-6-yl)-2-methylpropanenitrile is described in Patent Publication U.S. Pat. No. 6,410,563 B1 (2002).

General Method of Synthesis:

Coupling-1; General Procedure for Aryl-Aryl Coupling

A mixture of boronic acid or boronate ester (1.0 eq), aryl bromide (chloride or iodide) (1.1-2.0 eq.), Na$_2$CO$_3$ (3.0-3.5 eq.; 2 M in H$_2$O) and PdCl$_2$(dppf)$_2$ or Pd(OAc)$_2$-(Ph$_3$P)$_2$ or Pd(Ph$_3$P)$_4$ or Pd(1,3-Bis(2,4,6-trimethylphenyl)imidazolium chloride)$_2$ (0.05 eq.) in DME (or n-Propanol or Dioxane or DMF) (0.05-0.2 M) was stirred at 60-80° C. for 1-18 h. The mixture was cooled to room temperature and concentrated. Flash chromatography afforded the title compound. (Coupling using Aryl Iodide generally proceeds at lower temperature 20-60° C.).

Coupling-2; General Procedure for Aryl-Aryl Coupling

A mixture of boronic acid or boronate ester (1.0 eq), aryl bromide (or chloride or iodide) (1.1-2.0 eq), CsF (2.5 eq) or aqueous Na$_2$CO$_3$ (2M), Pd$_2$(dba)$_3$ (1.5%) and (t-Bu)$_3$P (4.5%) in THP or dioxane (0.05-0.2M) was stirred at 20° C. for 12-18 h. The mixture was concentrated, diluted with EtOAc and water then extracted. Flash chromatography afforded the title compound.

Coupling-3; General Procedure for Aryl-Aryl Coupling

A mixture of Aryltributyltin (1-2 eq), aryl bromide (1-2 eq), CuI (0.05 eq), PdCl$_2$(dppf) (0.05 eq) in dioxane (0.05-0.2 M) was stirred at 100° C. for 12-18 h. The mixture was concentrated, diluted with EtOAc and water then extracted. Flash chromatography afforded the title compound.

Oxid-1; General Procedure for Oxidation of Sulfide to Sulfone

To a solution Sulfide (1.0 eq.) in THF:MeOH:H$_2$O (2:2:1) (or alternatively replacing water with saturated aqueous NaHCO$_3$), was added Oxone (2.2 eq.). The mixture was stirred for 12 h at room temperature, poured in water and extracted with EtOAc (2×). The combined organic extracts were washed with aqueous NaHCO$_3$, brine, dried over MgSO$_4$ or Na$_2$SO$_4$, filtered and concentrated. Flash chromatography afforded the title compound.

Oxid-2: General Procedure for oxidation of Pyridinyl to Pyridinyl-N-oxide:

To a solution of Pyxidinyl (1.0 eq.) in CH$_2$Cl$_2$ (0.1 M) was added m-CPBA (1.3 eq.). The mixture was stirred at room temperature for 12 h, quenched with Ca(OH)$_2$ (0.7 eq) diluted with CH$_2$Cl$_2$ and filtered. The filtrate was concentrated and flash chromatography afforded the title compound.

Alternatively, the reaction mixture was quenched with EtOAc and aqueous NaHCO$_3$, the combined organic extracts were washed with aqueous NaHCO$_3$, brine, dried over MgSO$_4$ or Na$_2$SO$_4$, filtered and concentrated. Flash chromatography afforded the title compound.

Cer-1; General Procedure for Grignard Type Addition on Ester and Ketone Using CeCl$_3$ A heterogeneous solution of CeCl$_3$ (1.5 eq) and ester (1 eq) in TPF (0.1M) is sonicated at room temperature for 15 minutes. The resulting suspension is cooled to −78° C. and RMgX (Cl, Br, I, 6 eq) is added. The mixture is let to warm to −25° C. over a 2 hours period. The reaction is quenched with saturated solution of NH$_4$Cl and diluted with ethyl acetate. The organic phase is extracted, washed with brine and dry over MgSO$_4$ and concentrated. The residue was purified by flash chromatography (Hexane:EtOAc) or precipitated with ether/ethyl acetate to afforded the title compound.

Alternatively ketones can be used as starting material with 3 eq of Grignard reagent (RMgX).

Thio-1: General Procedure for conversion of nitrile to thioaride:

Heating nitrile derivative in MeOH at reflux with ammonium sulfide as described in SPYCHALA, J.; Synth Commun. 1997, 27 (19), 3431-3440. The product is generally purified by filtration, wash with water and air dried.

Bi-Aryl intermediates were prepared using the following procedures.

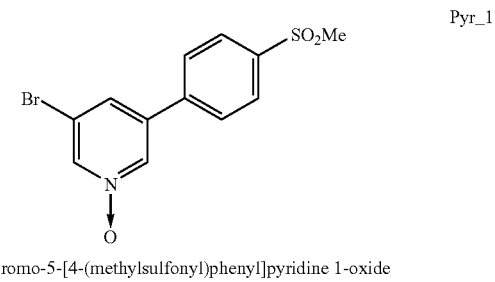

Pyr_1

3-bromo-5-[4-(methylsulfonyl)phenyl]pyridine 1-oxide

Step 1: 3-bromo-5-[4-(methylthio)phenyl]pyridine

Prepared according to the procedure Coupling-2 using [4-(methylthio)phenyl]boronic acid and 3,5-dibromopyridine as starting material. Flash chromatography (Hex:EtOAc; 95:5-85:15) afforded the title compound Step 2:
3-bromo-5-[4-(methylsulfonyl)phenyl]pyridine 1-oxide Prepared according to the procedure Oxid-1 and using oxone in excess (5 eq). The residue was stirred vigorously in EtOAc then isolated by filtration.

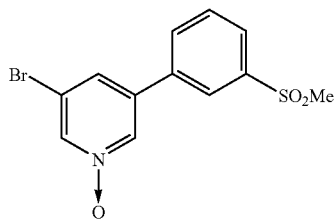

3-bromo-5-[3-(methylsulfonyl)phenyl]pyridine 1-oxide

Step 1: 3-bromo-5-[3-(methylthio)phenyl]pyridine

Prepared according to the procedure Coupling-2 using [3-(methylthio)phenyl]boronic acid and 3,5-dibromopyridine as starting material. Flash chromatography (Hex:EtOAc; 95:5-85:15) afforded the title compound.

Step 2: 3-bromo-5-[3-(methylsulfonyl)phenyl]pyridine 1-oxide

Prepared according to the procedure Oxid-2 and using mCPBA (3.2 eq). The residue was stirred vigorously in Et$_2$O then isolated by filtration.

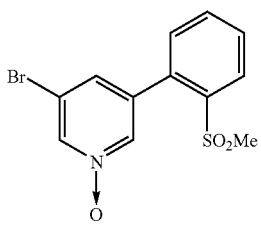

3-bromo-5-[2-(methylsulfonyl)phenyl]pyridine 1-oxide

Prepared according to the procedure described for Pyr_2 using [2-(methylthio)phenyl]boronic acid as starting material. The residue was stirred vigorously in Et$_2$O then isolated by filtration.

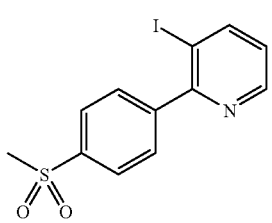

3-iodo-2-[4-(methylsulfonyl)phenyl]pyridine

Step 1: 3-amino-2-[4-(methylthio)phenyl]pyridine

Prepared according to the procedure Coupling-1 using [4-(methylthio)phenyl]boronic acid and 2-amino-1-chloropyridine as starting material. Flash chromatography (Hex:EtOAc; 60:40-50:50) afforded the title compound.

Step 2: 3-amino-2-[4-(methylsulfonyl)phenyl]pyridine

Prepared according to the procedure Oxid-1. Flash chromatography (Hex:EtOAc; 50:50-20:80) afforded the title compound as a white solid.

Step 3: 3-Iodo-2-[4-(methylsulfonyl)phenyl]pyridine

To a solution of 3-amino-2-[4-(methylsulfonyl)phenyl]pyridine (1.0 eq.) in AcOH:CH$_2$Cl$_2$ (1:1, 0.13 M) at −20° C. was added I$_2$ (1.5 eq), KI (1.5 eq) then NaNO$_2$ (1.5 eq). The mixture was stirred at 20° C. for 2 h then diluted with EtOAc and water. The organic extracts were washed with aqueous NaHCO$_3$, brine, dried over MgSO$_4$, filtered and concentrated. Flash chromatography (Hex:EtOAc; 40:60) afforded the title compound as a white solid.

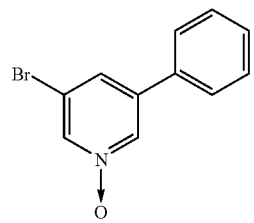

3-bromo-5-phenylpyridine 1-oxide

Prepared according to the procedure described for Pyr_2 using phenylboronic acid as starting material. Flash chromatography (Hex:EtOAc; 30:70), stirring vigorously in EtOAc-Et$_2$O-hexane then isolated by filtration.

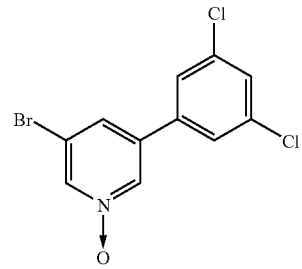

3-bromo-5-[3,5-(dichloro)phenyl]pyridine 1-oxide

Prepared according to the procedure described for Pyr_2 using 3,5-dichloro-phenylboronic acid as starting material. Flash chromatography (Hex:EtOAc; 30:70), stirring vigorously in EtOAc-Et$_2$O then isolated by filtration.

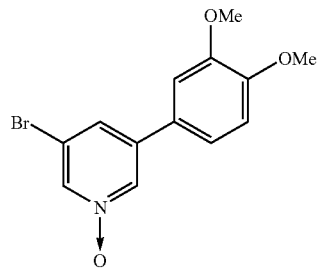

3-bromo-5-[3,5-(methoxy)phenyl]pyridine 1-oxide

Prepared according to the procedure described for Pyr_2 using 3,4-dimethoxy-phenylboronic acid as starting material.

Flash chromatography (Hex:EtOAc; 40:70 and then using toluene:acetone, 95:5) afforded the title compound.

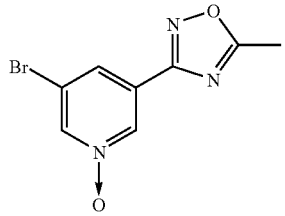

3-bromo-5-(5-methyl-1,2,4-oxadiazol-3-yl)pyridine 1-oxide

Pyr_8

Step 1: 5-bromo-N'-hydroxypyridine-3-carboximidamide

A mixture of 3-bromo-5-cyanopyridine (1.0 eq), hydroxylamine hydrochloride (1.5 eq.), $K_2CO_3$ (2.1 eq) in ethanol (0.1 M) was stirred at 80° C. for 3 days. The mixture was concentrated, diluted with EtOAc and aqueous $NaHCO_3$. The title compound was isolated by filtration as beige solid.

Step 2: 3-bromo-5-(5-methyl-1,2,4-oxadiazol-3-yl)pyridine

To a solution of 5-bromo-N'-hydroxypyridine-3-carboximidamide (1.0 eq.) in pyridine was added acetyl chloride (2 eq). The reaction stirred at 100° C. for 1 h and 2 eq of acetyl chloride was added. After 1 h, the mixture was cooled, diluted with EtOAc and aqueous $NaHCO_3$. The organic extracts were washed with aqueous $NaHCO_3$, brine, dried over $Na_2SO_4$, filtered and concentrated. Flash chromatography (Hex: EtOAc; 70:30) afforded the title compound as a white solid.

Step 3: 3-bromo-5-(5-methyl-1,2,4-oxadiazol-3-yl) pyridine 1-oxide

Prepared according to the procedure Oxid-2. Flash chromatography (EtOAc) afforded the title compound as a white solid.

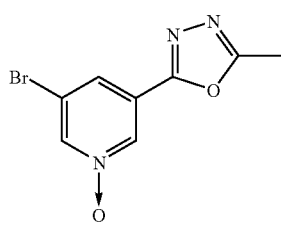

3-bromo-5-(5-methyl-1,3,4-oxadiazol-2-yl)pyridine 1-oxide

Pyr_9

Step 1: 3-bromo-5-(1H-tetraazol-5-yl)pyridine

To a mixture of 3-bromo-5-cyanopyridine (1.0 eq.) and triethylamine (1.3 eq in toluene (0.7 M) was added AcOH (1.3 eq). The reaction was stirred at 100° C. for 12 h, cooled, diluted with EtOAc and 1% AcOH solution. The organic extracts were washed with brine, dried over $Na_2SO_4$, filtered and concentrated to afford the title compound as a brown solid.

Step 2: 3-bromo-5-(5-methyl-1,3,4-oxadiazol-2-yl)pyridine

A solution of 3-bromo-5-(5-methyl-1,3,4-oxadiazol-2-yl) pyridine in acetic anhydride (0.8M) was at 140° C. for 2. The mixture was concentrated, diluted with EtOAc and aqueous $NaHCO_3$. The organic extracts were washed with aqueous $NaHCO_3$, brine, dried over $Na_2SO_4$, filtered and concentrated. Flash chromatography (Hex:EtOAc; 70:30) afforded the title compound as a white solid.

Step 3: 3-bromo-5-(5-methyl-1,3,4-oxadiazol-2-yl) pyridine 1-oxide

Prepared according to the procedure Oxid-2. Flash chromatography (EtOAc:MeOH, 100:0-95:5) afforded the title compound.

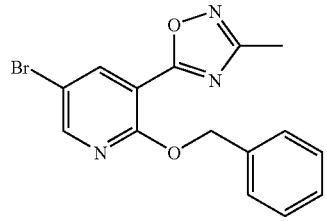

2-(benzyloxy)-5-bromo-3-(3-methyl-1,2,4-oxadiazol-5-yl)pyridine

Pyr_10

Step 1: 2-chloro-3-(3-methyl-1,2,4-oxadiazol-5-yl)pyridine

A mixture of 2-chloro nicotinoyl chloride (1.0 eq.) and N'-hydroxy ethanimidamide (1.1 eq) in pyridine (0.6 M) was stirred at 100° C. for 4 h and then concentrated. The residue was purified by flash chromatography (Hexane:EtOAc, 70:30) to afforded the title compound.

Step 2: 2-(benzyloxy)-3-(3-methyl-1,2,4-oxadiazol-5-yl)pyridine

To a solution of benzyl alcohol (1.5 eq) in DMF (0.4M) was added NaH (1.5 eq, 60%) followed by 2-chloro-3-(3-methyl-1,2,4-oxadiazol-5-yl)pyridine (1 eq) in DMF (0.5M) after 30 min.). The reaction was stirred at 20° C. for 1 h, diluted with $Et_2O$ and water. The organic extracts were washed with brine, dried over $MgSO_4$, filtered and concentrated. Flash chromatography (Hex:EtOAc; 80:20) afforded the title compound.

Step 3: 3-(3-methyl-1,2,4-oxadiazol-5-yl)pyridin-2-ol

A solution of 2-(benzyloxy)-3-(3-methyl-1,2,4-oxadiazol-5-yl)pyridine in $CH_2Cl_2$-TFA (0.25M) was stirred 15 min at 20° C. and then concentrated. The residue was diluted with EtOAc and aqueous $NaHCO_3$. The organic extracts were washed with brine, dried over $MgSO_4$, filtered and concentrated to afforded the title compound.

Step 4: 5-bromo-3-(3-methyl-1,2,4-oxadiazol-5-yl)pyridin-2-ol

A solution 3-(3-methyl-1,2,4-oxadiazol-5-yl)pyridin-2-ol in AcOH (0.2M) and bromine (1.2 eq) was stirred 18 h at 20° C. and then concentrated. The residue was co-evaporated with benzene (2×) and used as such in the next step.

Step 5: 2-(benzyloxy)-5-bromo-3-(3-methyl-1,2,4-oxadiazol-5-yl)pyridine

A solution 5-bromo-3-(3-methyl-1,2,4-oxadiazol-5-yl)pyridin-2-ol (1 eq) in benzene (0.05M) was added silver carbonate (1 eq) and benzyl bromide (1.2 eq). The reaction mixture was stirred 6 h at 20° C. and then concentrated. The residue was purified by flash chromatography (Hexane:EtOAc, 90:10) to afforded the title compound.

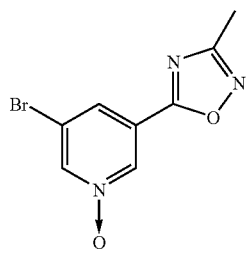

Pyr_11

3-bromo-5-(3-methyl-1,2,4-oxadiazol-5-yl)pyridine 1-oxide

Step 1: 3-bromo-5-(3-methyl-1,2,4-oxadiazol-5-yl)pyridine

A mixture of 5-bromo nicotinic acid (1.0 eq.) and CDI (1.1 eq) in DMF (0.25M) was stirred at 20° C. for 5 min and then N'-hydroxy ethanimidamide (1.1 eq) in pyridine (0.6 M) was added. The reaction mixture was stirred at 110° C. for 15 h, cooled to rt and poured into water. The title compound was isolated by filtration as a solid.

Step 2: 3-bromo-5-(3-methyl-1,2,4-oxadiazol-5-yl)pyridine 1-oxide

Prepared according to the procedure Ox-2. The residue was stirred vigorously in EtOAc then isolated by filtration.

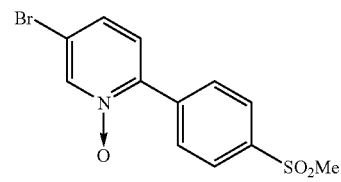

Pyr_12

5-bromo-2-[4-(methylsulfonyl)phenyl]pyridine 1-oxide

Step 1: 5-bromo-2-[4-(methylthio)phenyl]pyridine

Prepared according to the procedure Coupling-2 using [4-(methylthio)phenyl]boronic acid and 2,5-dibromo pyridine afforded the title compound in a mixture of isomer containing 2-bromo-5-[4-(methylthio)phenyl]pyridine.

Step 2: 5-bromo-2-[4-(methylsulfonyl)phenyl]pyridine

Prepared by submitting the mixture of isomer to the procedure Oxid-1. Flash chromatography (DCM:EtOAc 95:5-50:50) afforded the title compound (less polar isomer).

Step 3: 5-bromo-2-[4-(methylsulfonyl)phenyl]pyridine 1-oxide

Prepared according to the procedure Oxid-2. Flash chromatography (DCM:EtOAc 75:25-0:100) afforded the title compound.

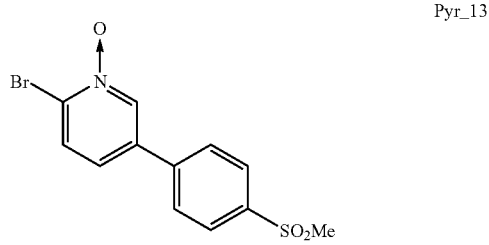

Pyr_13

2-bromo-5-[4-(methylsulfonyl)phenyl]pyridine 1-oxide

Prepared according to the procedure as described for Pyr_12 using the more polar isomer isolated from step 2.

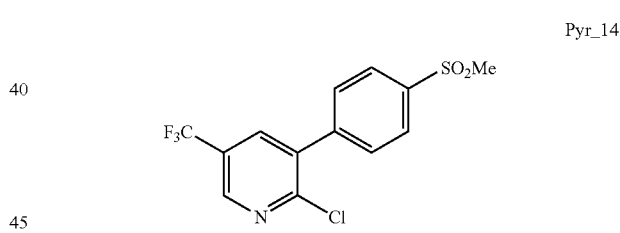

Pyr_14

3-chloro-3-[4-(methylsulfonyl)phenyl]-5-(trifluoromethyl)pyridine

Prepared according to the procedure as described in Bioorg. Med. Chem. Lett., 1999, 9, 1715, U.S. Pat. No. 5,861,419, 1999.

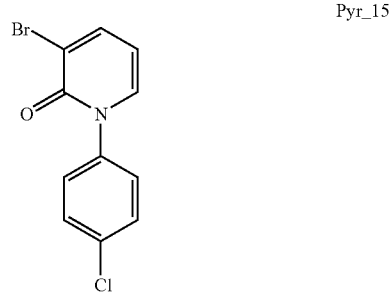

Pyr_15

3-bromo-1-(4-chlorophenyl)pyridin-2(1H)-one

Step 1: 1-(4-chlorophenyl)pyridin-2(1H)-one

Prepared according to the procedure as described in Chem.Pharm.Bull., 1997, 45, 719. Flash chromatography (Hex:EtOAc; 70:30) afforded the title compound.

Step 2: 3-bromo-1-(4-chlorophenyl)pyridin-2(1H)-one

A solution 1-(4-chlorophenyl)pyridin-2(1H)-one (1 eq) and tetrabutylammonium tribromide (1.2 eq) in chloroform (0.1M) was stirred 6 h at reflux. The reaction mixture was diluted with aqueous $NaHCO_3$ solution and aqueous $Na_2S_2O_3$ solution. The organic extracts were washed with brine, dried over $MgSO_4$, filtered and concentrated. The residue was purified by flash chromatography (Hexane:EtOAc, 80:20) to afforded the title compound.

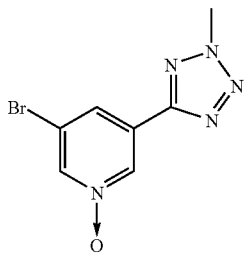

Pyr_16

3-bromo-5-(2-methyl-2H-tetraazol-5-yl)pyridine 1-oxide

Step 1: 3-bromo-5-(2H-tetraazol-5-yl)pyridine

A solution of 3-bromo-5-cyanopyridine (1 eq), sodium azide (1.2 eq), triethylamine (1.2 eq) and AcOH (1.2 eq) was stirred at 100C for 14 h. The reaction mixture was cooled to rt, diluted with aqueous acetic acid solution and extracted with EtOAc. The organic extracts were washed with brine, dried over $MgSO_4$, filtered and concentrated to afford the title compound.

Step 2: 3-bromo-5-(2-methyl-2H-tetraazol-5-yl)pyridine

To a solution of tetrazole from step 1 in $CH_2Cl_2$-MeOH (5:1, 0.1M) was added $CH_2N_2$ (in ether) until reaction completed by TLC. The reaction mixture was concentrated to afford the title compound.

Step 3: 3-bromo-5-(2-methyl-2H-tetraazol-5-yl)pyridine 1-oxide

Prepared according to the procedure Oxid-2. Flash chromatography ($CH_2Cl_2$-MeOH, 98:2) afforded the title compound.

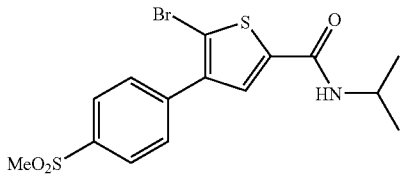

Het_1

5-bromo-N-isopropyl-4-[4-(methylsulfonyl)phenyl]thiophene-2-carboxamide

Step 1: 3-[4-(methylthio)phenyl]thiophene

Prepared according to the procedure Coupling-1 using [4-(methylthio)phenyl]boronic acid and 3-bromothiophene as starting material. Flash chromatography ($CH_2Cl_2$) afforded the title compound.

Step 2: 2-bromo-3-[4-(methylthio)phenyl]thiophene

To a solution of thiophene from step 1 (1.0 eq) in $CH_2Cl_2$/AcOH (1:1, 0.1M) was added NBS (1.05 eq). The mixture was stirred 1.5 h at r.t., diluted with EtOAc and aqueous $NaHCO_3$. The organic extracts were washed with water, brine, dried over $MgSO_4$, filtered and concentrated. Flash chromatography (Hexane:EtOAc, 80:20) afforded the title compound.

Step 3: 5-bromo-N-isopropyl-4-[4-(methylthio)phenyl]thiophene-2-carboxamide

To a solution of diisopropylamine (1.05 eq) in THF at −78° C. was added BuLi (1.6M, Hexane, 1.05 eq) dropwise. The mixture was stirred 10 min at 0° C., cooled to −78° C. and thiophene from step 2 added. After 30 min at −50° C., isopropyl isocyanate was added. The mixture was stirred 1 h at rt, diluted with EtOAc and aqueous $NaHCO_3$. The organic extracts were washed with water, brine, dried over $MgSO_4$, filtered and concentrated. Flash chromatography ($CH_2Cl_2$) afforded the title compound.

Step 4: 5-bromo-N-isopropyl-4-[4-(methylsulfonyl)phenyl]thiophene-2-carboxamide Prepared according to the procedure Oxid-1. Flash chromatography ($CH_2Cl_2$: EtOAc, 90:10) afforded the title compound.

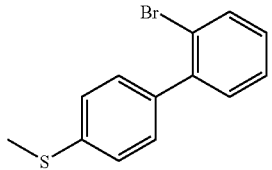

Phe_1

2-bromo-4'-(methylthio)-1,1'-biphenyl

Prepared according to the general procedure Coupling-1 using 4-methylthiobenzene boronic acid and 1-bromo-2-iodobenzene. Flash chromatography (Hexane:EtOAc, 100:0-95:5) afforded the title compound as an oil.

Phe_2

2-(2-bromophenyl)-5-methyl-1,3,4-oxadiazole

A mixture of 5-(2-bromophenyl)-2H-tetraazole (1.0 eq) in acetic anhydride (1M) was heated at 120° C. for 2 h and then concentrated. Flash chromatography (Hexane:EtOAc, 70:30) afforded the title compound as a white solid.

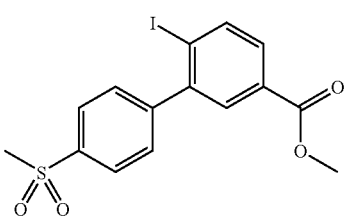

Phe_3 methyl 6-iodo-4'-(methylsulfonyl)-1,1'-biphenyl-3-carboxylate

Step 1: methyl 6-amino-4'-(methylthio)-1,1'-biphenyl-3-carboxylate

Prepared according to the general procedure Coupling-1 (CsF, DME, 20° C.) using [4-(methylthio)phenyl]boronic acid and methyl 4-amino-3-iodo-benzoate as starting material. Flash chromatography (Hexane:EtOAc, 70:30) afforded the title compound as a white solid.

Step 2: methyl 6-amino-4'-(methylsulfonyl)-1,1'-biphenyl-3-carboxylate

Prepared according to the general procedure Oxid-1. Flash chromatography (Hexane:EtOAc, 50:50) afforded the title compound.

Step 3: methyl 6-iodo-4'-(methylsulfonyl)-1,1'-biphenyl-3-carboxylate

To the amino from step 2 (1.0 eq) in $CH_2Cl_2$—AcOH (1:1) at −20° C. was added iodine (1.5 eq), KI (1.5 eq) followed by $NaNO_2$ (1.2 eq). The reaction mixture was stirred at r.t. for 1 h, diluted with EtOAc, a solution of $Na_2CO_3$ and a solution $Na_2S_2O_3$. The organic extracts were washed with water, brine, dried over $MgSO_4$, filtered and concentrated. Flash chromatography (Hexane:EtOAc, 30:20-20:30) afforded the title compound as a pale yellow solid.

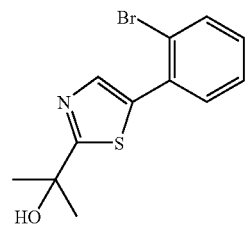

Phe_4

2-[5-(2-bromophenyl)-1,3-thiazol-2-yl]propan-2-ol

Step 1: 2-[5-(tributylstannyl)-1,3-thiazol-2-yl]propan-2-ol

To a solution of thiazole (1.0 eq) in THF (0.2M) at −78° C. was added nBuLi (1.6M, 1.1 eq). After 1 h at −78° C., acetone (1.0 eq) was added and the mixture stirred 30 min at −78° C., 5 min −50° C. then cooled back to −78° C. to add a second equivalent of nBuLi (1.6M, 1.1 eq). After 1.5 h at −78° C., tri-n-butyltin chloride (1.2 eq) was added and the mixture stirred 12 h at −78° C. The reaction mixture was diluted with $Et_2O$ and a solution of $NH_4Cl$. The organic extracts were washed with water, brine, dried over $MgSO_4$, filtered and concentrated. Flash chromatography (Hexane:EtOAc, 90:10) afforded the title compound.

Step 2: 2-[5-(2-bromophenyl)-1,3-thiazol-2-yl]propan-2-ol

A solution of stannane from step 1 (1.0 eq), 1-bromo-2-iodo-benzene (2.1 eq), CuI (0.2 eq), $PdCl_2(dppf)$ (0.1 eq) in DMF was heated 1 h at 80° C. The reaction mixture was diluted with EtOAc and a solution of $NH_4Cl$. The organic extracts were washed with water, brine, dried over $MgSO_4$, filtered and concentrated. Flash chromatography (Hexane:EtOAc, 80:20) afforded the title compound.

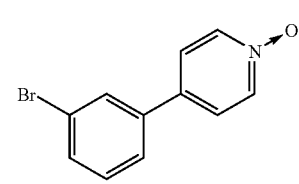

Phe_5

4-(3-bromophenyl)pyridine 1-oxide

Step 1: 4-(3-bromophenyl)pyridine

Prepared according to the general procedure Coupling-1 using 4-pyridinylboronic acid and 1,3-dibromobenzene. Flash chromatography (Hexane:EtOAc, 70:30) afforded the title compound.

Step 2: 4-(3-bromophenyl)pyridine 1-oxide

Prepared according to the general procedure Oxid-2. Flash chromatography (EtOAc:MeOH, 100:0 to 95:5) afforded the title compound.

EXAMPLE 1

8-(3-{2-(3-chlorophenyl)-4-[4-(methylsulfonyl)phenyl]-1,3-thiazol-5-yl}phenyl)-6-[1-methyl-1-(methylsulfonyl)ethyl]quinoline

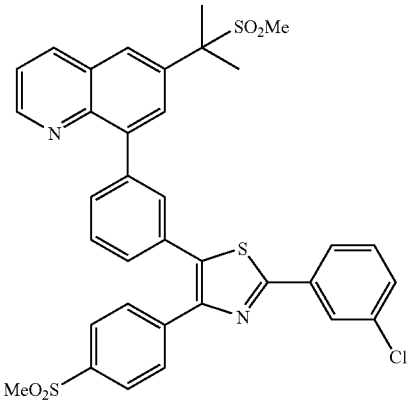

Step 1: diphenyl anilino[4-(methylthio)phenyl]methylphosphonate

To a solution of 4-methylthiobenzaldehyde (1.0 eq) dissolved in hot acetonitrile was added aniline (1.2 eq) and diphenyl phosphite (1.6 eq). The reaction mixture was stirred at 20° C. for 18 h and then concentrated. The residue can be purified by flash chromatography if necessary.

Step 2: 2-(3-{6-[1-methyl-1-(methylsulfonyl)ethyl]quinolin-8-yl}phenyl)-1-[4-(methylthio)phenyl]ethanone To a solution of phosphonate from step 1 (1.2 eq) dissolved in DMF (0.2M) was added cesium carbonate (1.5 eq), Quinoline_2 (1.0 eq) and isopropanol (20%, v/v). The reaction mixture was stirred at 70° C. for 30 min (or 20° C. for 18 h), cooled to rt diluted with HCl (6N), stirred for 2 h and extracted with EtOAc. The organic extracts were washed with brine, dried over MgSO$_4$, filtered and concentrated. The residue was purified by flash chromatography (Hexane:EtOAc, 50:50) to afforded the title compound.

Step 3: 2-(3-{6-[1-methyl-1-(methylsulfonyl)ethyl]quinolin-8-yl}phenyl)-1-[4-(methylsulfonyl)phenyl]ethanone Prepared according to the procedure Oxid-1. Flash chromatography (Hexane:EtOAc) afforded the title compound.

Step 4: 2-bromo-2-(3-{6-[1-methyl-1-(methylsulfonyl)ethyl]quinolin-8-yl}phenyl)-1-[4-(methylsulfonyl)phenyl]ethanone A solution of ketone from step 3 (1.0 eq) in chloroform (0.2M) with polymer-supported tribromide (1 mmol/g, 1.2 eq) was heated at reflux for 1-2 h, filtered and concentrated to afforded the title compound.

Step 5: 8-(3-{2-(3-chlorophenyl)-4-[4-(methylsulfonyl)phenyl]-1,3-thiazol-5-yl}phenyl)-6-[1-methyl-1-(methylsulfonyl)ethyl]quinoline To a solution of the alpha-bromoketone from step 4 (1.0 eq) in DMF (0.1M) was added 3-chlorobenzenecarbothioamide (1.0 eq). The mixture was heated at 40-120° C. for 1-3 h, cooled, diluted with water, saturated NaHCO$_3$ solution and ether. The organic extracts were washed with brine, dried over MgSO$_4$, filtered and concentrated. The residue was purified by flash chromatography (Hexane:EtOAc) to afforded the title compound.

$^1$H NMR (500 MHz, DMSO-d$_6$): δ 8.85 (dd, 1H), 8.46 (dd, 1H), 8.22 (d, 1H), 8.04 (s, 1H, 7.95-7.90 (m, 6H), 7.73 (m, 2H), 7.55 (m, 4H), 7.48 (d, 1H), 3.28 (s, 3H), 2.74 (s, 3H), 1.85 (s, 6H).

Following examples (Table 1) were prepared according to the procedure described for EXAMPLE 1. Non-commercial thioamide used in step 5 of example 1, were prepared according to general procedure Thio-1.

TABLE 1

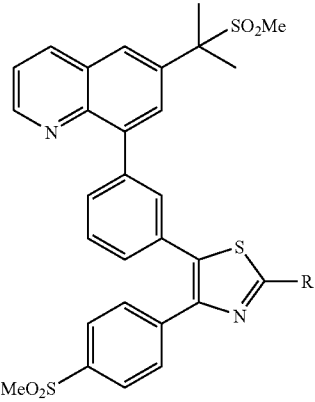

| Ex #: | R group name | ESI-LRMS (M + 1)$^+$ |
|---|---|---|
| 2 | Amino | 709.8 |
| 3 | 2-biphenyl | 636.5 |
| 4 | 3-biphenyl | 636.6 |
| 5 | N-(tert-butoxycarbonyl)-4-phenylpyrrolidin-3-yl | 729.7 |
| 6 | N-(tert-butoxycarbonyl)azetidin-3-yl | 639.6 |
| 7 | N-(tert-butoxycarbonyl)pyrrolidin-3-yl | 653.9 |
| 8 | 3-chloro-4-fluorophenyl | 611.3 |
| 9 | 4-chlorophenoxymethyl | 624.4 |
| 10 | 2-chlorophenyl | 594.5 |
| 11 | 4-chlorophenyl | 593.3 |
| 12 | Ethoxycarbonyl | 635.3 |
| 13 | furan-2-yl | 550.5 |
| 14 | furan-3-yl | 550.4 |
| 15 | imidazol-2-yl | 550.4 |
| 16 | indan-1-yl | 600.6 |
| 17 | indan-2-yl | 600.6 |
| 18 | 1H-indol-2-yl | 599.5 |
| 19 | 1H-indol-3-yl | 599.6 |
| 20 | 1H-indol-4-yl | 599.4 |
| 21 | 1H-indol-5-yl | 599.5 |
| 22 | 1H-indol-6-yl | 599.6 |
| 23 | 1H-indol-7-yl | 599.5 |
| 24 | isoquinolin-1-yl | 611.5 |
| 25 | isoquinolin-4-yl | 611.5 |
| 26 | isoquinolin-5-yl | 611.5 |
| 27 | isoquinolin-8-yl | 690.5 |
| 28 | isoxazol-3-yl | 551.5 |

TABLE 1-continued

[Structure shown: quinoline with SO₂Me group, connected through phenyl to thiazole ring bearing 4-(MeO₂S)phenyl and R substituent]

| Ex #: | R group name | ESI-LRMS (M + 1)⁺ |
|---|---|---|
| 29 | 3-methoxycarbonylphenyl | 697.2 |
| 30 | 4-methoxycarbonylphenyl | 697.2 |
| 31 | Methyl | 577.3 |
| 32 | 1-methyl-1H-pyrazol-3-yl | 564.5 |
| 33 | 1-methyl-1H-pyrazol-4-yl | 564.6 |
| 34 | 1-methyl-1H-pyrazol-5-yl | 564.5 |
| 35 | 2-methylphenyl | 653.3 |
| 36 | 3-methylphenyl | 653.3 |
| 37 | 4-methylphenyl | 574.6 |
| 38 | 2-methylpyridin-5-yl | 575.5 |
| 39 | Methylsulfonylmethyl | 576.5 |
| 40 | 2-methylsulfonylphenyl | 717.3 |
| 41 | 3-methylsulfonylphenyl | 717.3 |
| 42 | 4-methylsulfonylphenyl | 717.3 |
| 43 | morpholin-4-ylmethyl | 575.5 |
| 44 | Phenyl | 639.3 |
| 45 | Pyrazinyl | 562.4 |
| 46 | 1H-pyrazol-3-yl | 550.4 |
| 47 | pyridin-2-yl | 561.5 |
| 48 | pyridin-3-yl | 561.5 |
| 49 | pyridin-4-yl | 561.5 |
| 50 | 3-pyridinylmethyl | 575.6 |
| 51 | pyrimidin-2-yl | 562.4 |
| 52 | pyrimidin-4-yl | 562.4 |
| 53 | pyrimidin-5-yl | 562.4 |
| 54 | quinolin-4-yl | 611.5 |
| 55 | quinolin-5-yl | 611.5 |
| 56 | quinolin-8-yl | 611.5 |
| 57 | 5,6,7,8-tetrahydro-1,8-naphthyridin-2-yl | 695.6 |
| 58 | 6,7,8,9-tetrahydro-5H-benzo[a][7]annulen-5-yl | 628.6 |
| 59 | 6,7,8,9-tetrahydro-5H-benzo[a][7]annulen-6-yl | 628.6 |
| 60 | tetrahydrofuran-2-yl | 554.5 |
| 61 | 1,2,3,4-tetrahydronaphthalen-1-yl | 615.7 |
| 62 | 1,2,3,4-tetrahydronaphthalen-2-yl | 615.6 |
| 63 | 1,3-thiazol-2-yl | 567.3 |
| 64 | 1,3-thiazol-5-yl | 567.4 |
| 65 | thiophen-2-yl | 566.2 |
| 66 | thiophen-3-yl | 566.3 |

EXAMPLE 67

6-[1-methyl-1-(methylsulfonyl)ethyl]-8-{3-[4-[4-(methylsulfonyl)phenyl]-2-(1-oxidopridin-4-yl)-1,3-thiazol-5-yl]phenyl}quinoline

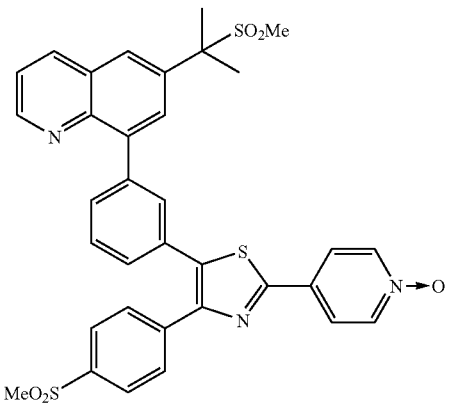

Prepared according to the general procedure Oxid-2 using EXAMPLE 49 as starting material.

¹H NMR (500 MHz, acetone-d₆): δ 8.88 (dd, 1H), 8.45 (dd, 1H), 8.28-8.26 (m, 3H), 8.10 (d, 1H), 8.04 (d, 2H), 8.01 (d, 2H), 7.96 (d, 2H), 7.86 (s, 1H), 7.83 (d, 1H), 7.61 (t, 1H), 7.58-7.55 (m, 2H), 3.14 (s, 3H), 2.69 (s, 3H), 1.96 (s, 6H).

ESI-LRMS (M+1) 656.4

EXAMPLE 68

6-[1-methyl-1-(methylsulfonyl)ethyl]-8-{3-[4-[4-(methylsulfonyl)phenyl]-2-(1-oxidopyridin-3-yl)-1,3-thiazol-5-yl]phenyl}quinoline

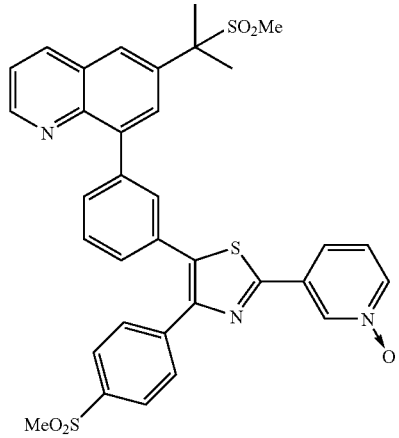

Prepared according to the general procedure Oxid-2 using EXAMPLE 48 as starting material.

¹H NMR (500 MHz, acetone-d₆): δ 8.88 (dd, 1H), 8.79 (s, 1H), 8.44 (dd, 1H), 8.28 (d, 1H), 8.25 (d, 1H), 8.10 (d, 1H), 8.03 (d, 2H), 7.97 (d, 2H), 7.89-7.84 (m, 3H), 7.63 (t, 1H), 7.58-7.47. (m, 3H), 3.15 (s, 3H), 2.70 (s, 3H), 1.96 (s, 6H).

ESI-LRMS (M+1) 656.3

EXAMPLE 69

2-(3-{5-(3-{6-[1-methyl-1-(methylsulfonyl)ethyl]quinolin-8-yl}phenyl)-4-[4-(methylsulfonyl)phenyl]-1,3-thiazol-2-yl}phenyl)propan-2-ol

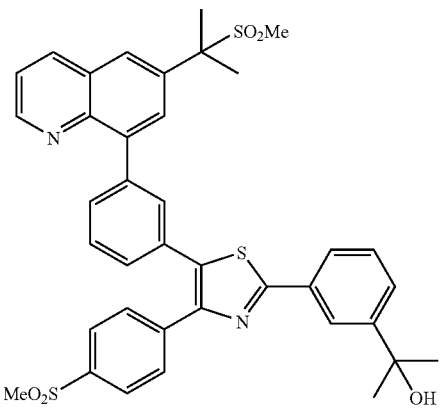

Prepared according to the general procedure Cer-1 using methyl magnesium bromide and EXAMPLE 29 as starting material.

¹H NMR (500 MHz, acetone-d₆): δ 8.89 (dd, 1H), 8.44 (dd, 1H), 8.28 (dd, 2H), 8.09 (d, 1H), 8.01 (d, 2H), 7.95 (d, 2H), 7.92 (d, 1H), 7.86 (s, 1H), 7.82 (d, 1H), 7.66 (d, 1H), 7.60 (t, 1H), 7.57-7.54 (m, 2H), 7.48 (t, 1H), 4.28 (s, 0.6H), 3.13 (s, 3H), 2.69 (s, 3H), 1.96 (s, 6H), 1.58 (s, 6H).

ESI-LRMS (M+1) 617.4

EXAMPLE 70

3-{5-(3-{6-[1-methyl-1-(methylsulfonyl)ethyl]quinolin-8-yl}phenyl)-4-[4-(methylsulfonyl)phenyl]-1,3-thiazol-2-yl}benzoic acid

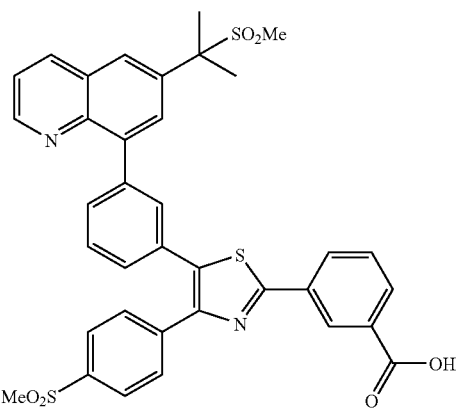

To a solution of EXAMPLE 29 in THF/MeOH/H₂O (0.05M) was added LiOH (2N, 5 eq). The reaction mixture was stirred at rt for 2 h, acidified with AcOH, diluted with water and extracted with CH₂Cl₂. The organic extracts were washed with brine, dried over Na₂SO₄, filtered and concentrated. The title compound was isolated by filtration from acetone/ether as a solid.

¹H NMR (500 MHz, acetone-d₆): δ 8.89 (dd, 1H), 8.72 (s, 1H), 8.44 (dd, 1H), 8.31 (d, 1H), 8.27 (d, 1H), 8.17 (d, 1H), 8.10 (d, 1H), 8.03 (d, 2H), 7.96 (d, 2H), 7.88 (s, 1H), 7.83 (d, 1H), 7.69 (t, 1H), 7.61 (t, 1H), 7.58-7.54 (m, 2H), 3.14 (s, 3H), 2.69 (s, 3H), 1.96 (s, 6H).

ESI-LRMS (M+1) 683.3

EXAMPLE 71

2-{5-(3-{6-[1-methyl-1-(methylsulfonyl)ethyl]quinolin-8-yl}phenyl)-4-[4-(methylsulfonyl)phenyl]-1,3-thiazol-2-yl}propan-2-ol

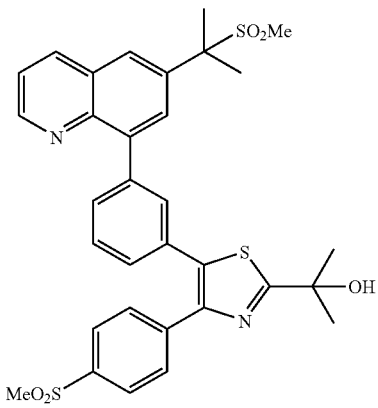

Prepared according to the general procedure Cer-1 using methyl magnesium bromide and EXAMPLE 12 as starting material.

¹H NMR (500 MHz, acetone-d₆): δ 8.88 (dd, 1H), 8.45 (dd, 1H), 8.27 (d, 1H), 8.09 (d, 1H), 7.90 (m, 4H), 7.77 (m, 2H), 7.56 (m, 2H), 7.47 (m, 1H), 5.26 (s, OH), 3.10 (s, 3H), 2.70 (s, 3H), 1.95 (s, 6H), 1.70 (s, 6H).

EXAMPLE 72

6-[1-methyl-1-(methylsulfonyl)ethyl]-8-(3-{2-(3-methyl-1,2,4-oxadiazol-5-yl)-4-[4-(methylsulfonyl)phenyl]-1,3-thiazol-5-yl}phenyl)quinoline

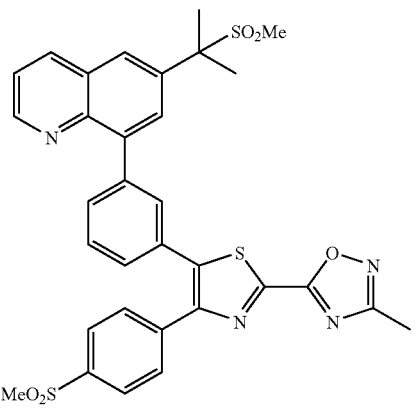

Step 1: 5-(3-{6-[1-methyl-1-(methylsulfonyl)ethyl]quinolin-8-yl}phenyl)-4-[4-(methylsulfonyl)phenyl]-1,3-thiazole-2-carboxylic acid To a solution of EXAMPLE 12 in THF/MeOH/H₂O (0.05M) was added LiOH (2N, 2 eq). The reaction mixture was stirred at rt for 2 h, acidified with HCO₂H, diluted with water and extracted with EtOAc. The organic extracts were washed with brine and concentrated to afford he title compound as a solid.

Step 2: 6-[1-methyl-1-(methylsulfonyl)ethyl]-8-(3-{2-(3-methyl-1,2,4-oxadiazol-5-yl)-4-[4-(methylsulfonyl)phenyl]-1,3-thiazol-5-yl}phenyl)quinoline To a solution of acid from step 1 in DMF (0.05M) was added CDI (1.1 eq) and, after 5 min, acetamidoxime (1.1 eq). The reaction mixture was stirred at rt for 1 h and 18 h at 110° C. The reaction mixture was cooled to rt and poured into water. The residue was purified by flash chromatography (toluene:EtOAc, 45:55) to afforded the title compound and decarboxylated analog EXAMPLE 73 (more polar product).
¹H NMR (500 MHz, acetone-d₆): δ 8.88 (dd, 1H), 8.47 (dd, 1H), 8.30 (d, 1H), 8.12 (d, 1H), 8.01 (s, 4H), 7.90 (m, 2H), 7.60 (m, 3H), 3.18 (s, 3H), 2.70 (s, 3H), 2.52 (s, 3H), 1.95 (s, 6H).

EXAMPLE 73

6-[1-methyl-1-(methylsulfonyl)ethyl]-8-(3-{4-[4-(methylsulfonyl)phenyl]-1,3-thiazol-5-yl}phenyl)quinoline

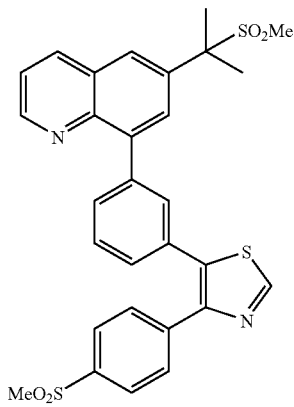

Prepared according to the procedure described for EXAMPLE 72.
¹H NMR (500 MHz, acetone-d₆): δ 9.15 (s, 1H), 8.88 (dd, 1H), 8.43 (dd, 1H), 8.25 (d, 1H), 8.08 (d, 1H), 7.92 (m, 4H), 7.80 (m, 2H), 7.59 (t, 1H), 7.55 (dd, 1H), 7.50 (m, 1H), 3.12 (s, 3H), 2.70 (s, 3H), 1.95 (s, 6H).

EXAMPLE 74

N-cyclopropyl-5-(3-{6-[1-methyl-1-(methylsulfonyl)ethyl]quinolin-8-yl}phenyl)-4-[4-(methylsulfonyl)phenyl]-1,3-thiazole-2-carboxamide

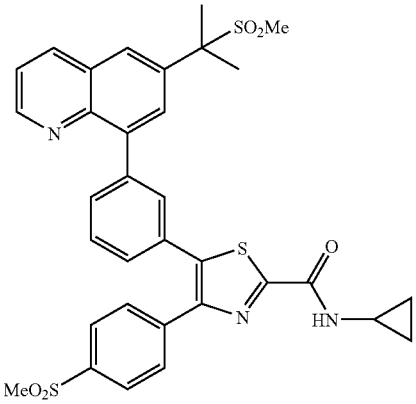

To a solution of EXAMPLE 12 in CH₂Cl₂ (0.05M) was added cyclopropylamine (4 eq) and trimethylaluminum (2M, Hexanes, 4 eq). The reaction mixture was stirred at rt for 18 h. The reaction mixture was diluted slowly with a saturated NH₄Cl solution, a 1 M sodium potassium tartrate solution and EtOAc. The mixture was extracted with EtOAc, the organic extracts were washed with brine, dried over MgSO₄, filtered and concentrated. The residue was purified by flash chromatography (EtOAc) to afford the title compound.
¹H NMR (500 MHz, acetone-d₆): δ 8.86 (dd, 1H), 8.43 (dd, 1H), 8.31 (d, 1H), 8.26 (d, 1H), 8.07 (d, 1H), 7.91 (s, 4H), 7.83 (m, 2H), 7.55 (m, 3H), 3.12 (s, 3H), 2.95 (m, 1H), 2.69 (s, 3H), 1.95 (s, 6H), 0.78 (m, 2H), 0.73 (m, 2H).

EXAMPLE 75

6-[1-methyl-1-(methylsulfonyl)ethyl]-8-(3-{2-(6-methyl-1-oxidopyridin-3-yl)-4-[4-(methylsulfonyl)phenyl]-1,3-thiazol-5-yl}phenyl)quinoline

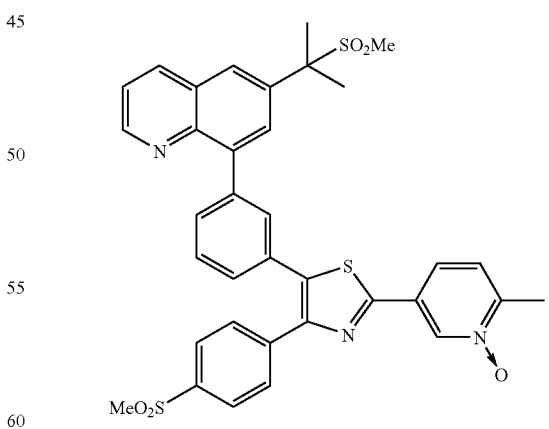

Prepared according to the general procedure Oxid-2 using EXAMPLE 38 as starting material.
¹H NMR (500 MHz, acetone-d₆): δ 8.87 (m, 2H), 8.44 (dd, 1H), 8.26 (d, 1H), 8.09 (d, 1H), 8.0-7.9 (m, 2H), 8.0-7.9 (m, 5H), 7.67-7.5 (m, 4H), 3.13 (s, 3H), 2.7 (s, 3H), 2.45 (s, 3H), 1.95 (s, 6H).

EXAMPLE 76

2-[4-(4-chlorophenyl)-5-(3-{6-[1-methyl-1-(methylsulfonyl)ethyl]quinolin-8-yl}phenyl)-1,3-thiazol-2-yl]propan-2-ol

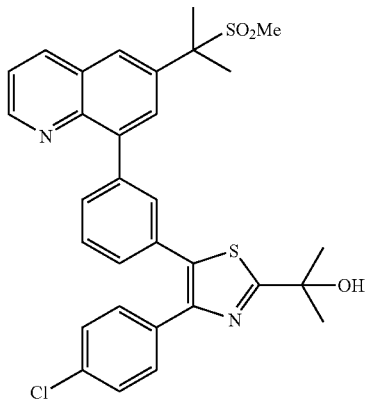

Step 1: ethyl 4-(4-chlorophenyl)-5-(3-{6-[1-methyl-1-(methylsulfonyl)ethyl]quinolin-8-yl}phenyl)-1,3-thiazole-2-carboxylate Prepared according to the procedure described for EXAMPLE 1 using 4-chloro benzaldehyde in step 1 and ethyl thiooxamate in step 5. Flash chromatography (Hexane:EtOAc, 50:50-20:80) afforded the title compound.

Step 2: 2-[4-(4-chlorophenyl)-5-(3-{6-[1-methyl-1-(methylsulfonyl)ethyl]quinolin-8-yl}phenyl)-1,3-thiazol-2-yl]propan-2-ol Prepared according to the general procedure Cer-1 using methyl magnesium bromide. Flash chromatography (Hexane:EtOAc, 35:65) afforded the title compound as a white foam.

$^1$H NMR (500 MHz, acetone-$d_6$): δ 8.85 (dd, 1H), 8.40 (dd, 1H), 8.25 (d, 1H), 8.05 (s, 1H), 7.75 (m, 2H), 7.65 (d, 3H), 7.35 (d, 2H), 7.0 (m, 2H), 5.10 (s, OH), 2.66 (s, 3H), 1.95 (s, 6H), 1.7 (s, 6H).

EXAMPLE 77

6-[1-methyl-1-(methylsulfonyl)ethyl]-8-(3-{2-methyl-4-[4-(methylsulfonyl)phenyl]-1,3-oxazol-5-yl}phenyl)quinoline

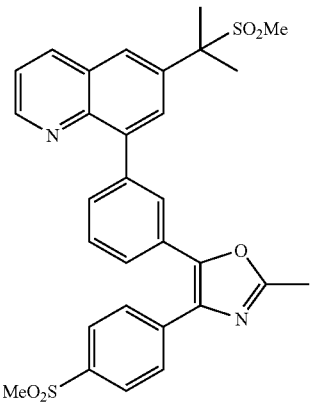

Prepared according to the procedure described for EXAMPLE 1 using acetamide at 120° C. in step 5. Flash chromatography (CH$_2$Cl$_2$: EtOAc, 80:20) afforded the title compound.

$^1$H NMR (500 MHz, acetone-$d_6$): δ 8.94 (dd, 1H), 8.45 (dd, 1H), 8.27 (d, 1H), 8.12 (d, 1H), 8.03 (d, 2H), 7.98 (m, 3H), 7.80 (d, 1H), 7.70 (m, 1H), 7.62 (m, 1H), 7.57 (m, 1H), 3.12 (s, 3H), 2.7 (s, 3H), 2.52 (s, 3H), 1.95 (s, 6H).

EXAMPLE 78

2-{4-(3-{6-[1-methyl-1-(methylsulfonyl)ethyl]quinolin-8-yl}phenyl)-5-[4-(methylsulfonyl)phenyl]-1,3-thiazol-2-yl}propan-2-ol

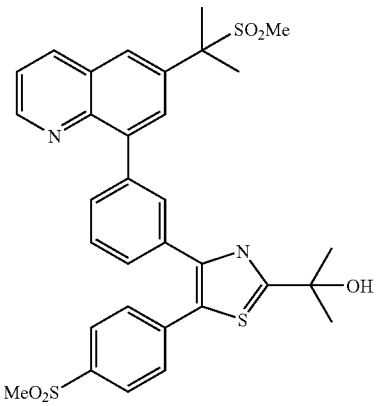

Step 1: ethyl 4-(3-{6-[1-methyl-1-(methylsulfonyl)ethyl]quinolin-8-yl}phenyl)-5-[4-(methylthio)phenyl]-1,3-thiazole-2-carboxylate Prepared according to the procedure described for EXAMPLE 1 using Quinoline_2 in step 1,4-methylthiobenzaldehyde in step 2 and ethyl thiooxamate in step 5.

Step 2: 2-{4-(3-{6-[1-methyl-1-(methylsulfonyl)ethyl]quinolin-8-yl}phenyl)-5-[4-(methylthio)phenyl]-1,3-thiazol-2-yl}propan-2-ol Prepared according to the general procedure Cer-1 using methyl magnesium bromide. Flash chromatography (CH$_2$Cl$_2$:MeOH, 98:2) afforded the title compound.

Step 3: 2-{4-(3-{6-[1-methyl-1-(methylsulfonyl)ethyl]quinolin-8-yl}phenyl)-5-[4-(methylsulfonyl)phenyl]-1,3-thiazol-2-yl}propan-2-ol.

Prepared according to the general procedure Oxid-1. Flash chromatography (toluene:acetone, 70:30) afforded the title compound.

$^1$H NMR (500 MHz, acetone-$d_6$): δ 8.89 (dd, 1H), 8.43 (dd, 1H), 8.26 (d, 1H), 8.05 (d, 1H), 7.96 (d, 2H), 7.87 (t, 1H), 7.73 (d, 2H), 7.72 (d, 1H), 7.63 (d, 1H), 7.55 (dd, 1H), 7.50 (t, 1H), 5.20 (s, OH), 3.13 (s, 3H), 2.71 (s, 3H), 1.97 (s, 6H), 1.71 (s, 6H).

EXAMPLE 79

1,1,1-trifluoro-N-{5-(3-{6-[1-methyl-1-(methylsulfonyl)ethyl]quinolin-8-yl}phenyl)-4-[4-(methylsulfonyl)phenyl]-1,3-thiazol-2-yl}methanesulfonamide

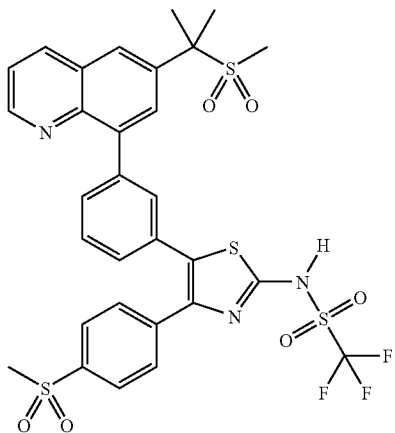

To a suspension of EXAMPLE 2 in CH$_2$Cl$_2$ at −78° C. was added triethylamine (4 eq) and Tf$_2$O (2.2 eq). The reaction was stirred at −78° C. 15 min then warmed to 20° C. for 1 h, diluted with NaHCO$_3$ solution and CH$_2$Cl$_2$ and stirred 15 min. The organic extracts were washed with brine, dried over Na$_2$SO$_4$, filtered and concentrated. Flash chromatography (EtOAc) afforded the title compound.

$^1$H NMR (500 MHz, acetone-d$_6$): δ 8.89 (dd, 1H), 8.43 (dd, 1H), 8.27 (d, 1H), 8.06 (d, 1H), 7.89 (d, 2H), 7.87 (d, 2H), 7.73-7.70 (m, 2H), 7.56 (dd, 1H), 7.52 (t, 1H), 7.43 (dd, 1H), 3.12 (s, 3H), 2.70 (s, 3H), 1.98 (s, 6H).

EXAMPLE 80

2-[5-(3-{6-[1-methyl-1-(methylsulfonyl)ethyl]quinolin-8-yl}phenyl)-4-pyridin-3-yl-1,3-thiazol-2-yl]propan-2-ol

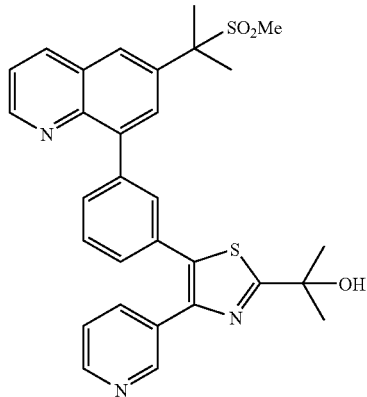

Step 1: ethyl 4-(3-{6-[1-methyl-1-(methylsulfonyl)ethyl]quinolin-8-yl}phenyl)-5-pyridin-3-yl-1,3-thiazole-2-carboxylate Prepared according to the procedure described for EXAMPLE 1 using 3-pyridinecarboxaldehyde in step 1 and ethyl thiooxamate in step 5. Flash chromatography (Hexane:EtOAc, 50:50-0:100) afforded the title compound.

Step 2: 2-[4-(3-{6-[1-methyl-1-(methylsulfonyl)ethyl]quinolin-8-yl}phenyl)-5-pyridin-3-yl-1,3-thiazol-2-yl]propan-2-ol Prepared according to the general procedure Cer-1 using methyl magnesium bromide. Flash chromatography (CH$_2$Cl$_2$:MeOH, 96:4) afforded the title compound.

$^1$H NMR (500 MHz, acetone-d$_6$): δ 8.86-8.85 (m, 2H), 8.49 (dd, 1H), 8.39 (dd, 1H), 8.24 (d, 1H), 8.05 (d, 1H), 7.97 (dt, 1H), 7.78-7.75 (m, 2H), 7.54-7.50 (m, 2H), 7.45 (dt, 1H), 7.33 (dd, 1H), 5.26 (br s, OH), 2.67 (s, 3H), 1.94 (s, 6H), 1.69 (s, 6H).

EXAMPLE 81

2-[5-(3-{6-[1-methyl-1-(methylsulfonyl)ethyl]quinolin-8-yl}phenyl)-4-(1-oxidopyridin-3-yl)-1,3-thiazol-2-yl]propan-2-ol

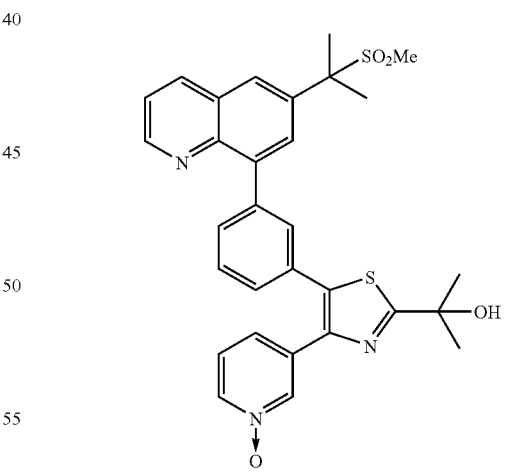

Prepared according to the general procedure Oxid-2 using EXAMPLE 80 as starting material. Flash chromatography (CH$_2$Cl$_2$:MeOH, 95:5) afforded the title compound.

$^1$H NMR (500 MHz, acetone-d$_6$): δ 8.89 (dd, 1H), 8.43 (d, 1H), 8.26 (s, 1H), 8.00 (s, 1H), 7.82 (s, 1H), 7.72 (d, 1H), 7.68 (d, 1H), 7.58 (dd, 1H), 7.50-7.43 (m, 5H), 5.12 (s, OH), 2.68 (s, 3H), 1.98 (s, 6H), 1.70 (s, 6H).

EXAMPLE 82

1-(4-chlorophenyl)-1-{4-(3-{6-[1-methyl-1-(methylsulfonyl)ethyl]quinolin-8-yl}phenyl)-5-[4-(methylsulfonyl)phenyl]-1,3-thiazol-2-yl}ethanol

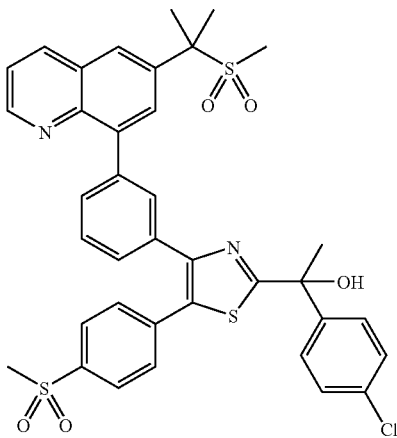

Step 1: ethyl 4-(3-{6-[1-methyl-1-(methylsulfonyl)ethyl]quinolin-8-yl}phenyl)-5-[4-(methylthio)phenyl]-1,3-thiazole-2-carboxylate Prepared according to the procedure described for EXAMPLE 1 using Quinoline_2 in step 1, 4-methylthiobenzaldehyde in step 2 and ethyl thiooxamate in step 5. (step 3 is omitted).

Step 2: N-methoxy-N-methyl-4-(3-{6-[1-methyl-1-(methylsulfonyl)ethyl]quinolin-8-yl}phenyl)-5-[4-(methylthio)phenyl]-1,3-thiazole-2-carboxamide To a solution of methoxymethylamine in THF (0.08M) at −78° C. was added methylmagnesium iodide (3M, ether, 1 eq) dropwise over 1 h. The reaction mixture was stirred at −78° C. for 10 min, a solution of ester from step 1 was added and the reaction mixture was stirred at −78° C. for 2 h. The mixture was quenched with AcOH, diluted with $NH_4Cl$ solution and EtOAc. The organic extracts were washed with brine, dried over $Na_2SO_4$, filtered and concentrated. The residue was purified by flash chromatography (toluene:acetone, 80:20) to afforded the title compound.

Step 3: 1-{4-(3-{6-[1-methyl-1-(methylsulfonyl)ethyl]quinolin-8-yl}phenyl)-5-[4-(methylthio)phenyl]-1,3-thiazol-2-yl}ethanone Prepared according to the general procedure Cer-1 using methylmagnesium iodide and amide from step 2.

Step 4: 1-(4-chlorophenyl)-1-{4-(3-{6-[1-methyl-1-(methylsulfonyl)ethyl]quinolin-8-yl}phenyl)-5-[4-(methylthio)phenyl]-1,3-thiazol-2-yl}ethanol Prepared according to the general procedure Cer-1 using 4-chlorophenylmagnesium bromide and methylketone from step 3. Flash chromatography ($CH_2Cl_2$:MeOH, 96:4) afforded the title compound.

Step 5: 1-(4-chlorophenyl)-1-{4-(3-{6-[1-methyl-1-(methylsulfonyl)ethyl]quinolin-8-yl}phenyl)-5-[4-(methylsulfonyl)phenyl]-1,3-thiazol-2-yl}ethanol Prepared according to the general procedure Oxid-1 using sulfide from step 4 as starting material. Flash chromatography ($CH_2Cl_2$:MeOH, 99:1) afforded the title compound.

$^1$H NMR (500 MHz, acetone-$d_6$): δ 8.90 (dd, 1H), 8.44 (dd, 1H), 8.26 (d, 1), 8.07 (d, 1H), 7.95 (dd, 2H), 7.90 (t, 1H), 7.83 (dd, 2H), 7.76 (dd, 1H), 7.71 (dd, 2H), 7.62 (dt, 1H), 7.56 (dd, 1H), 7.50 (t, 1H), 7.40 (dd, 2H), 6.05 (s, OH), 3.12 (s, 3H), 2.72 (s, (s, 3H), 1.98 (s, 6H).

The following compounds (Table 2) were prepared according to the procedure described previously (Ex. 1-80). Indicated is their respective (M+1)$^+$ value obtained from a low resolution mass spectrometer under electron-spray ionization conditions.

TABLE 2

| EX. | Chemical name | ESI-LRMS (M + 1)$^+$ |
|---|---|---|
| 83 | 6-[1-methyl-1-(methylsulfonyl)ethyl]-8-(3-{2-[3-(methylsulfonyl)phenyl]-4-phenyl-1,3-thiazol-5-yl}phenyl)quinoline | 639.3 |
| 84 | 2-[4-(3-chlorophenyl)-5-(3-{6-[1-methyl-1-(methylsulfonyl)ethyl]quinolin-8-yl}phenyl)-1,3-thiazol-2-yl]propan-2-ol | 577.2 |
| 85 | 2-[4-(4-fluorophenyl)-5-(3-{6-[1-methyl-1-(methylsulfonyl)ethyl]quinolin-8-yl}phenyl)-1,3-thiazol-2-yl]propan-2-ol | 561.2 |
| 86 | 8-{3-[4-(4-chlorophenyl)-2-quinolin-5-yl-1,3-thiazol-5-yl]phenyl}-6-[1-methyl-1-(methylsulfonyl)ethyl]quinoline | 646.2 |
| 87 | 2-{3-[4-(3-chlorophenyl)-5-(3-{6-[1-methyl-1-(methylsulfonyl)ethyl]quinolin-8-yl}phenyl)-1,3-thiazol-2-yl]phenyl}propan-2-ol | 653.5 |
| 88 | 2-{3-[4-(3-chloro-4-fluorophenyl)-5-(3-{6-[1-methyl-1-(methylsulfonyl)ethyl]quinolin-8-yl}phenyl)-1,3-thiazol-2-yl]phenyl}propan-2-ol | 670.9 |
| 89 | 2-{3-[4-[3,4-bis(difluoromethoxy)phenyl]-5-(3-{6-[1-methyl-1-(methylsulfonyl)ethyl]quinolin-8-yl}phenyl)-1,3-thiazol-2-yl]phenyl}propan-2-ol | 751.3 |
| 90 | N-{5-(3-{6-[1-methyl-1-(methylsulfonyl)ethyl]quinolin-8-yl}phenyl)-4-[4-(methylsulfonyl)phenyl]-1,3-thiazol-2-yl}acetamide | 619.7 |
| 91 | N-{5-(3-{6-[1-methyl-1-(methylsulfonyl)ethyl]quinolin-8-yl}phenyl)-4-[4-(methylsulfonyl)phenyl]-1,3-thiazol-2-yl}pyridin-4-amine | 655.4 |
| 92 | 2-[5-(3-{6-[1-methyl-1-(methylsulfonyl)ethyl]quinolin-8-yl}phenyl)-4-pyridin-4-yl-1,3-thiazol-2-yl]propan-2-ol | 543.9 |
| 93 | 2-[5-(3-{6-[1-methyl-1-(methylsulfonyl)ethyl]quinolin-8-yl}phenyl)-4-(1-oxidopyridin-4-yl)-1,3-thiazol-2-yl]propan-2-ol | 560.7 |
| 94 | 2-[5-(4-chlorophenyl)-4-(3-{6-[1-methyl-1-(methylsulfonyl)ethyl]quinolin-8-yl}phenyl)-1,3-thiazol-2-yl]propan-2-ol | 577.2 |
| 95 | 2-{3-[4-(4-chlorophenyl)-5-(3-{6-[1-methyl-1-(methylsulfonyl)ethyl]quinolin-8-yl}phenyl)-1,3-thiazol-2-yl]phenyl}propan-2-ol | 653.6 |
| 96 | 6-[1-methyl-1-(methylsulfonyl)ethyl]-8-{3-[5-(1H-tetrazol-5-yl)pyridin-3-yl]phenyl}quinoline | 471.1 |

EXAMPLE 97

6-[1-methyl-1-(methylsulfonyl)ethyl]-8-(3-{3-[4-(methylsulfonyl)phenyl]thien-2-yl}phenyl)quinoline

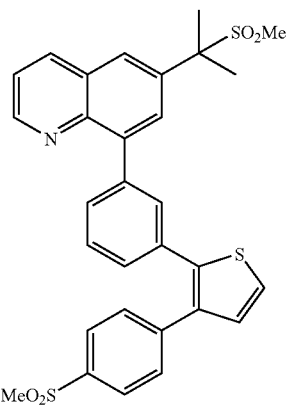

Step 1: 2-bromo-3-[4-(methylthio)phenyl]thiophene

Prepared according to the general procedure Coupling-1 using 4-methylthiobenzeneboronic acid and 3-bromothiophene. Flash chromatography (CH$_2$Cl$_2$) afforded the title compound.

Step 2: 4-(2-bromothien-3-yl)phenyl methyl sulfone

Prepared according to the general procedure Oxid-1 using sulfide from step 1 as starting material.

Step 3: 6-[1-methyl-1-(methylsulfonyl)ethyl]-8-(3-{3-[4-(methylsulfonyl)phenyl]thien-2-yl}phenyl)quinoline Prepared according to the general procedure Coupling-1 using Quinoline_4 and 3-bromothiophene from step 2 as starting material. Flash chromatography (toluene:EtOAc; 70:30) afforded the title compound.

$^1$H NMR (500 MHz, acetone-d$_6$): δ 8.88 (dd, 1H), 8.45 (dd, 1H), 8.25 (d, 1H), 8.03 (d, 1H), 7.89 (d, 2H), 7.70 (m, 2H), 7.62 (m, 3H), 7.55 (dd, 1H), 7.47 (t, 1H), 7.37 (m, 1H), 7.32 (d, 1H), 3.08 (s, 3H), 2.70 (s, 3H), 1.95 (s, 6H).

EXAMPLE 98

1-(3"-{6-[1-methyl-1-(methylsulfonyl)ethyl]quinolin-8-yl}-1,1':2',1"-terphenyl-4-yl)ethanone

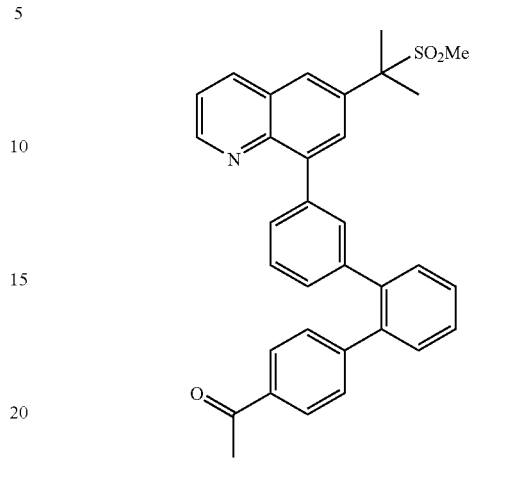

Step 1: 8-(2'-bromo-1,1'-biphenyl-3-yl)-6-[1-methyl-1-(methylsulfonyl)ethyl]quinoline Prepared according to the general procedure Coupling-1 using Quinoline_4 and 1,2-dibromobenzene as starting material. Flash chromatography (Hex:EtOAc; 50:50) afforded the title compound.

Step 2: 1-(3"-{6-[1-methyl-1-(methylsulfonyl)ethyl]quinolin-8-yl}-1,1':2',1"-terphenyl-4-yl)ethanone Prepared according to the general procedure Coupling-1 using bromide from step 1 and 4-acetylbenzeneboronic acid as starting material. Flash chromatography (Hex:EtOAc; 50:50) afforded the title compound.

$^1$H NMR (500 MHz, Benzene-d$_6$): δ 8.81 (d, 1H), 7.93 (d, 1H), 7.85 (s, 1H), 7.80 (m, 3H), 7.75 (s, 1H), 7.61 (m, 2H), 7.38 (m, 7H), 6.87 (dd, 1H), 2.35 (s, 3H), 2.05 (s, 3H), 1.65 (s, 6H).
+ESI (M+1) 520.2

EXAMPLE 99

2-(3"-{6-[1-methyl-1-(methylsulfonyl)ethyl]quinolin-8-yl}-1,1':2',1"-terphenyl-4-yl)propan-2-ol

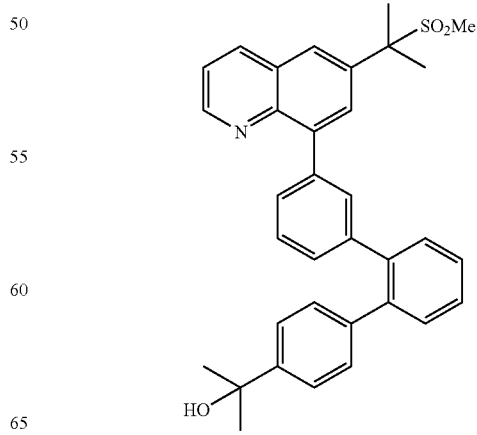

Step 1: 1-(2'-bromo-1,1'-biphenyl-4-yl)ethanone

Prepared according to the general procedure Coupling-1 using 4-acetylbenzeneboronic acid and 1,2-dibromobenzene as starting material. Flash chromatography (Hex:EtOAc; 95:5) afforded the title compound.

Step 2: 2-(2'-bromo-1,1'-biphenyl-4-yl)propan-2-ol

Prepared according to the general procedure Cer-1 using methyl magnesium bromide and ketone from step 1 as starting material. Flash chromatography (Hex:EtOAc; 90:10) afforded the title compound.

Step 3: 2-(3''-{6-[1-methyl-1-(methylsulfonyl)ethyl]quinolin-8-yl}-1,1':2',1''-terphenyl-4-yl)propan-2-ol Prepared according to the general procedure Coupling-1 using Quinoline_4 and bromide from step 2 as starting material. Flash chromatography (Hex:EtOAc; 50:50) afforded the title compound.

$^1$H NMR (500 MHz, acetone-d$_6$): δ 8.94 (dd, 1H), 8.45 (dd, 1H), 8.27 (d, 1H), 8.01 (d, 1H), 7.68 (d, 1H), 7.62 (br s, 1H), 7.55 (m, 2H), 7.48 (m, 3H), 7.42 (d, 2H), 7.38 (t, 1H), 7.21 (m, 3H).

+ESI (M+1) 536.8

EXAMPLE 100

6-[1-methyl-1-(methylsulfonyl)ethyl]-8-{3-[5-(3-methyl-1,2,4-oxadiazol-5-yl)-1-oxidopyridin-3-yl]phenyl}quinoline

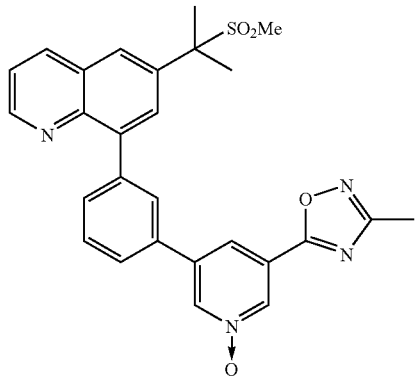

Prepared according to the general procedure Coupling-1 using Quinoline_4 and Pyr_11 as starting material. Flash chromatography (EtOAc:EtOH; 90:10) and crystallisation from EtOAc/ether afforded the title compound.

The following compounds (Table 3) were prepared according to the general procedure Coupling_1 using Quinoline 4 and intermediates described previously or commercial products (Commercial). Indicated is their respective (M+1)$^+$ value obtained from a low resolution mass spectrometer under electron-spray ionization conditions.

TABLE 3

| EX. | intermediate | Chemical name | ESI-LRMS (M + 1)$^+$ |
|---|---|---|---|
| 101 | Pyr_1 | 6-[1-methyl-1-(methylsulfonyl)ethyl]-8-(3-{5-[4-(methylsulfonyl)phenyl]-1-oxidopyridin-3-yl}phenyl)quinoline | 573.1 |
| 102 | Pyr_2 | 6-[1-methyl-1-(methylsulfonyl)ethyl]-8-(3-{5-[3-(methylsulfonyl)phenyl]-1-oxidopyridin-3-yl}phenyl)quinoline | 573.6 |
| 103 | Pyr_3 | 6-[1-methyl-1-(methylsulfonyl)ethyl]-8-(3-{5-[2-(methylsulfonyl)phenyl]-1-oxidopyridin-3-yl}phenyl)quinoline | 573.2 |
| 104 | Pyr_4 | 6-[1-methyl-1-(methylsulfonyl)ethyl]-8-(3-{2-[4-(methylsulfonyl)phenyl]pyridin-3-yl}phenyl)quinoline | 557.1 |
| 105 | Pyr_5 | 6-[1-methyl-1-(methylsulfonyl)ethyl]-8-[3-(1-oxido-5-phenylpyridin-3-yl)phenyl]quinoline | 495.1 |
| 106 | Pyr_6 | 8-{3-[5-(3,5-dichlorophenyl)-1-oxidopyridin-3-yl]phenyl}-6-[1-methyl-1-(methylsulfonyl)ethyl]quinoline | 563.1/565.1 |
| 107 | Pyr_7 | 8-{3-[5-(3,4-dimethoxyphenyl)-1-oxidopyridin-3-yl]phenyl}-6-[1-methyl-1-(methylsulfonyl)ethyl]quinoline | 555.1 |
| 108 | Pyr_8 | 6-[1-methyl-1-(methylsulfonyl)ethyl]-8-{3-[5-(5-methyl-1,2,4-oxadiazol-3-yl)-1-oxidopyridin-3-yl]phenyl}quinoline | 501.1 |
| 109 | Pyr_9 | 6-[1-methyl-1-(methylsulfonyl)ethyl]-8-{3-[5-(5-methyl-1,3,4-oxadiazol-2-yl)-1-oxidopyridin-3-yl]phenyl}quinoline | 501.1 |
| 110 | Pyr_10 | 8-{3-[6-(benzyloxy)-5-(3-methyl-1,2,4-oxadiazol-5-yl)pyridin-3-yl]phenyl}-6-[1-methyl-1-(methylsulfonyl)ethyl]quinoline | 591.2 |
| 111 | Pyr_12 | 6-[1-methyl-1-(methylsulfonyl)ethyl]-8-(3-{6-[4-(methylsulfonyl)phenyl]-1-oxidopyridin-3-yl}phenyl)quinoline | 573.3 |
| 112 | Pyr_13 | 6-[1-methyl-1-(methylsulfonyl)ethyl]-8-(3-{5-[4-(methylsulfonyl)phenyl]-1-oxidopyridin-2-yl}phenyl)quinoline | 573.3 |

TABLE 3-continued

| EX. | intermediate | Chemical name | ESI-LRMS (M + 1)+ |
|---|---|---|---|
| 113 | Pyr_14 | 6-[1-methyl-1-(methylsulfonyl)ethyl]-8-{3-[3-[4-(methylsulfonyl)phenyl]-5-(trifluoromethyl)pyridin-2-yl]phenyl}quinoline | 625.3 |
| 114 | Pyr_15 | 1-(4-chlorophenyl)-3-(3-{6-[1-methyl-1-(methylsulfonyl)ethyl]quinolin-8-yl}phenyl)pyridin-2(1H)-one | 529.1 |
| 115 | Pyr_16 | 6-[1-methyl-1-(methylsulfonyl)ethyl]-8-{3-[5-(2-methyl-2H-tetraazol-5-yl)-1-oxidopyridin-3-yl]phenyl}quinoline | 501.1 |
| 116 | Het_1 | N-isopropyl-5-(3-{6-[1-methyl-1-(methylsulfonyl)ethyl]quinolin-8-yl}phenyl)-4-[4-(methylsulfonyl)phenyl]thiophene-2-carboxamide | 647.4 |
| 117 | Commercial | 6-[1-methyl-1-(methylsulfonyl)ethyl]-8-(1,1':2',1''-terphenyl-3-yl)quinoline | 478.1 |
| 118 | Phe_1 | 6-[1-methyl-1-(methylsulfonyl)ethyl]-8-[4''-(methylsulfonyl)-1,1':2',1''-terphenyl-3-yl]quinoline | 556.2 |
| 119 | Phe_2 | 6-[1-methyl-1-(methylsulfonyl)ethyl]-8-[2'-(5-methyl-1,3,4-oxadiazol-2-yl)-1,1'-biphenyl-3-yl]quinoline | 484.2 |
| 120 | Phe_3 | methyl 3-{6-[1-methyl-1-(methylsulfonyl)ethyl]quinolin-8-yl}-4''-(methylsulfonyl)-1,1':2',1''-terphenyl-4'-carboxylate | |
| 121 | Commercial | 6-[1-methyl-1-(methylsulfonyl)ethyl]-8-(1,1':4',1''-terphenyl-3-yl)quinoline | 478.2 |
| 122 | Commercial | 6-[1-methyl-1-(methylsulfonyl)ethyl]-8-(1,1':3',1''-terphenyl-3-yl)quinoline | 478.2 |
| 123 | Phe_4 | 2-[5-(3'-{6-[1-methyl-1-(methylsulfonyl)ethyl]quinolin-8-yl}-1,1'-biphenyl-2-yl)-1,3-thiazol-2-yl]propan-2-ol | 542.0 |
| 124 | Phe_5 | 6-[1-methyl-1-(methylsulfonyl)ethyl]-8-[3'-(1-oxidopyridin-4-yl)-1,1'-biphenyl-3-yl]quinoline | 495.1 |

EXAMPLE 125

5-(3-{6-[1-methyl-1-(methylsulfonyl)ethyl]quinolin-8-yl}phenyl)-3-(3-methyl-1,2,4-oxadiazol-5-yl)pyridin-2(1H)-one

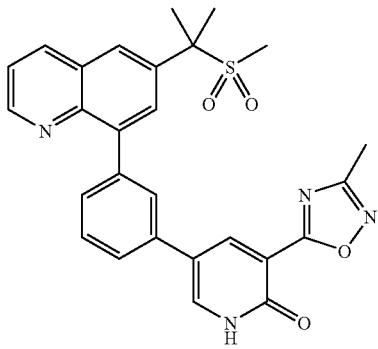

A solution of EXAMPLE 110 (1.0 eq) in CH$_2$Cl$_2$/TFA (2:1, 0.06M) was stirred at r.t. for 2 h, volatiles evaporated, diluted with EtOAc, washed with a solution of Na$_2$CO$_3$ and brine. The organic extracts were dried over MgSO$_4$, filtered and concentrated. Stirring in EtOAc and isolation by filtration provided the title compound.

$^1$H NMR (500 MHz, DMSO-d$_6$): δ 8.92 (dd, 1H), 8.62 (d, 1H), 8.51 (dd, 1H), 8.27 (d, 1H), 8.17 (s, 1H), 8.03 (d, 1H), 7.86 (s, 1H), 7.68 (d, 1H), 7.62-7.55 (m, 3H), 2.80 (s, 3H), 2.37 (s, 3H), 1.92 (s, 6H).

EXAMPLE 126

6-[1-methyl-1-(methylsulfonyl)ethyl]-8-(3-{6-[4-(methylsulfonyl)phenyl]imidazo[2,1-b][1,3]thiazol-5-yl}phenyl)quinoline

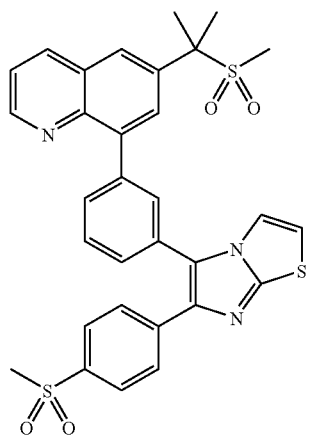

To a solution of the alphabromoketone from EXAMPLE 1, step 4 (1.0 eq) in DMF (0.1M) was added 2-aminothiazole (1.6 eq). The mixture was heated at 120° C. for 1 h, cooled, diluted with water, saturated NaHCO$_3$ solution and EtOAc. The organic extracts were washed with brine, dried over Na$_2$SO$_4$, filtered and concentrated. The residue was purified by flash chromatography (Toluene:EtOAc, 1:3) to afforded the title compound.

$^1$H NMR (500 MHz, acetone-$d_6$): δ 9.02 (dd, 1H), 8.50 (dd, 1H), 8.32 (d, 1H), 8.26 (d, 1H), 8.08-8.05 (m, 4H), 7.92 (d, 2H), 7.85 (d, 1H), 7.69 (t, 1H), 7.62-7.59 (m, 2H), 7.36 (d, 1H), 3.15 (s, 3H), 2.74 (s, 3H), 2.01 (s, 6H).

EXAMPLE 127

6-[1-methyl-1-(methylsulfonyl)ethyl]-8-(3-{2-[4-(methylsulfonyl)phenyl]imidazo[1,2-a]pyridin-3-yl}phenyl)quinoline

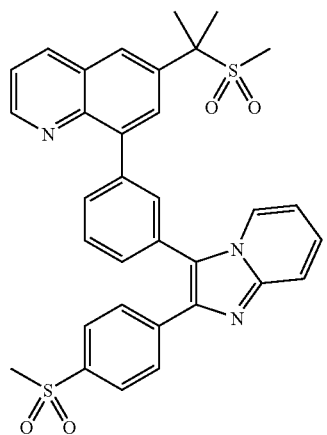

Prepared according to the procedure described for EXAMPLE 126 and using 2-aminopyridine as starting material. Flash chromatography (Toluene:EtOAc, 1:3) afforded the title compound.

$^1$H NMR (500 MHz, acetone-$d_6$): δ 9.00 (dd, 1H), 8.50. (d, 1H), 8.48 (dd, 1H), 8.32 (d, 1H), 8.27 (d, 1H), 8.14 (d, 2H), 8.07 (t, 1H), 7.94-7.92 (m, 3H), 7.76 (t, 1H), 7.67 (d, 1H), 7.62-7.59 (m, 2H), 7.39 (dd, 1H), 7.03 (dt, 1H), 3.16 (s, 3H), 2.74 (s, 3H), 2.01 (s, 6H).

EXAMPLE 128

[3-{6-[1-methyl-1-(methylsulfonyl)ethyl]quinolin-8-yl}-4''-(methylthio)-1,1':2',1''-terphenyl-4'-yl]methanol

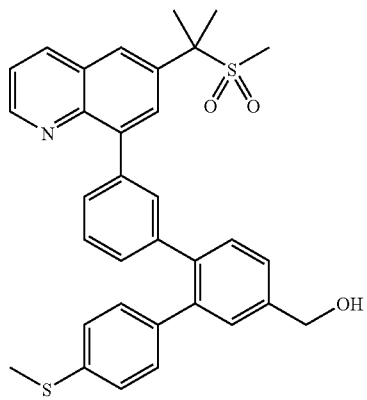

Step 1: 2-bromo-3'-{6-[1-methyl-1-(methylsulfonyl)ethyl]quinolin-8-yl}-1,1'-biphenyl-4-carbaldehyde Prepared according to the general procedure Coupling_1 using Quinoline_4 and 3,4-dibromobenzaldehyde as starting materials. Flash chromatography (hexane:EtOAc, 9:1 to 1:1) afforded the title compound as foam.

Step 2: 3-{6-[1-methyl-1-(methylsulfonyl)ethyl]quinolin-8-yl}-4''-(methylthio)-1,1':2',1''-terphenyl-4'-carbaldehyde Prepared according to the general procedure Coupling_1 using aldehyde from step 1 and 4-methylthiobenzeneboronic acid as starting materials. Flash chromatography (hexane:EtOAc, 3:2 to 1:1) afforded the title compound.

Step 3: [3-{6-[1-methyl-1-(methylsulfonyl)ethyl]quinolin-8-yl}-4''-(methylthio)-1,1':2',1''-terphenyl-4'-yl]methanol To a solution of aldehyde from step 2 in EtOH: THF (4:1, 0.05M) at 0° C. was added NaBH$_4$ (1 eq). The reaction mixture was stirred 1 h at 0° C., quenched with a solution of NH$_4$Cl and diluted with ether. The organic extracts were washed with brine, dried over Na$_2$SO$_4$, filtered and concentrated. The residue was purified by flash chromatography (hexane:EtOAc, 1:1 to 1:9) to afforded the title compound.

$^1$H NMR (500 MHz, acetone-$d_6$): δ 8.91 (dd, 1H), 8.43 (d, 1H), 8.25 (d, 1H), 7.88 (d, 1H), 7.67 (d, 1H), 7.56 (dd, 1H), 7.55-7.46 (m, 4H), 7.42 (t, 1H), 7.29-7.18 (m, 5H), 4.76 (d, 2H), 4.33 (t, 1H), 2.70 (s, 3H), 2.474 (s, 3H), 1.97 (s, 6H).

EXAMPLE 129

[3-{6-[1-methyl-1-(methylsulfonyl)ethyl]quinolin-8-yl}-4''-(methylsulfonyl)-1,1':2',1''-terphenyl-4'-yl]methanol

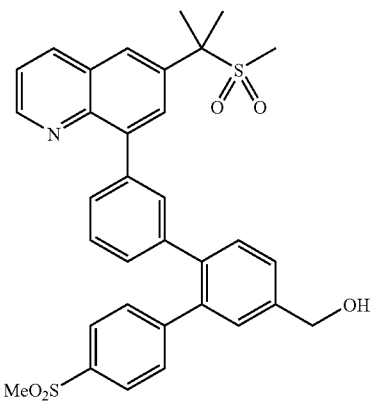

Prepared according to the general procedure Oxid-1 using Example 128 as starting material. The title compound was isolated as white foam.

$^1$H NMR (500 MHz, acetone-$d_6$): δ 8.91 (dd, 1H), 8.44 (d, 1H), 8.26 (d, 1H), 7.98 (d, 1H), 7.85 (d, 2H), 7.68 (d, 1H), 7.58-7.52 (m, 7H), 7.41 (t, 1H), 7.25 (d, 1H), 4.79 (d, 2H), 4.4 (t, 1H), 3.03 (s, 3H), 2.71 (s, 3H), 1.97 (s, 6H).

EXAMPLE 130

2-[3-{6-[1-methyl-1-(methylsulfonyl)ethyl]quinolin-8-yl}-4''-(methylsulfonyl)-1,1':2',1''-terphenyl-4'-yl]propan-2-ol

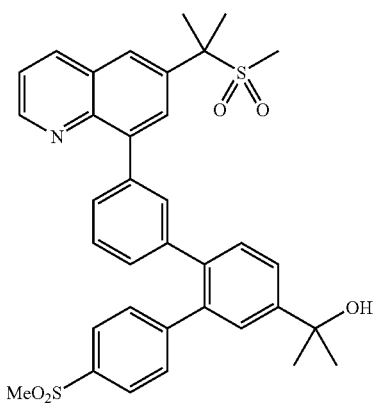

Prepared according to the general procedure Cer-1 using Example 120 as starting material. The residue was purified by flash chromatography (hexane:EtOAc, 1:1 to 3:7) to afforded the title compound.

¹H NMR (500 MHz, acetone-d₆): δ 8.91 (dd, 1H), 8.42 (dd, 1H), 8.25 (d, 1H), 7.98 (d, 1H), 7.85 (d, 2H), 7.71-7.67 (m, 3H), 7.57-7.53 (m, 4H), 7.40 (t, 1H), 7.23 (d, 1H), 4.24 (s, OH), 3.03 (s, 3H), 2.71 (s, 3H), 1.97 (s, 6H), 1.63 (s, 6H).

EXAMPLE 131

3-{6-[1-methyl-1-(methylsulfonyl)ethyl]quinolin-8-yl}4''-(methylsulfonyl)-1,1':2',1''-terphenyl-4'-carboxylic acid

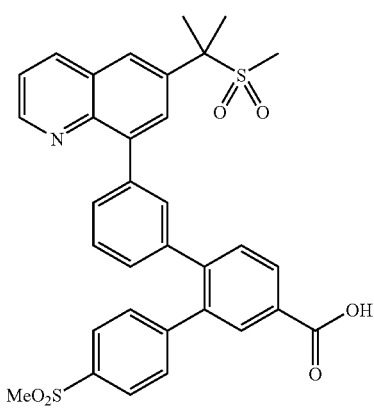

To a solution of Example 120 in THF:MeOH (1:1, 0.05M) was added LiOH (2N, 5 eq). The reaction mixture was stirred at rt for 24 h, acidified to pH 2 with 1N HCl and diluted with EtOAc. The organic extracts were washed with brine, dried over Na₂SO₄, filtered and concentrated. The residue was sonicated in hexane/EtOAc and title product isolated by filtration as a white powder.

¹H NMR (500 MHz, CD₃OD): δ 8.86 (dd, 1H), 8.44 (d, 1H), 8.22 (d, 1H), 8.16 (dd, 1H), 8.12 (d, 1H), 7.87 (d, 2H), 7.84 (d, 1H), 7.69 (d, 1H), 7.61-7.54 (m, 4H), 7.46 (t, 1H), 7.43 (s, 1H), 7.32 (d, 1H), 4.79 (d, 2H), 4.4 (t, 1H), 3.04 (s, 3H), 2.74 (s, 3H), 1.98 (s, 6H).

EXAMPLE 132

6-[1-methyl-1-(methylsulfonyl)ethyl]-8-(3-{2-[4-(methylsulfonyl)phenyl]-1-oxidopedin-3-yl}phenyl)quinoline

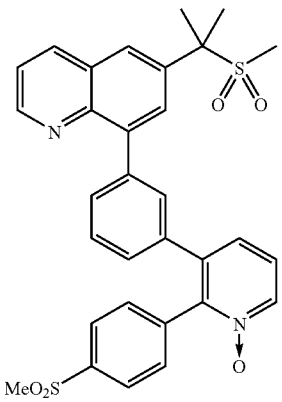

Prepared according to the general procedure Oxid-2 using Example 104 as starting material. The residue was sonicated in hexane/EtOAc and title product isolated by filtration as a white powder.

¹H NMR (500 MHz, acetone-d₆): δ 8.92 (dd, 1H), 8.42 (dd, 1H), 8.35 (d, 1H), 8.25 (d, 1H), 7.95 (d, 1H), 7.85 (d, 2H), 7.65 (d, 2H), 7.57-7.48 (m, 5H), 7.36 (t, 1H), 7.21 (d, 1H), 3.02 (s, 3H), 2.70 (s, 3H), 1.96 (s, 6H).

EXAMPLE 133

8-{3-[3-(4-fluorophenyl)-1,2,4-oxadiazol-5-yl]phenyl}-6-[1-methyl-1-(methylsulfonyl)ethyl]quinoline

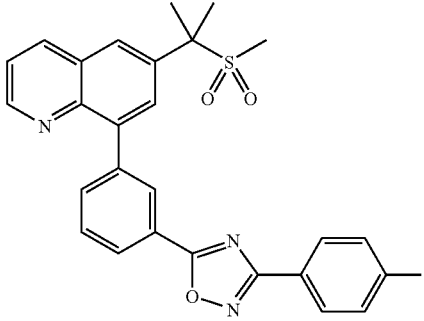

Step 1: methyl 3-{6-[1-methyl-1-(methylsulfonyl)ethyl]quinolin-8-yl}benzoate

To a solution of Quinoline_2 in CH₂Cl₂:MeOH (1:2, 0.03M) was added NaCN (1.8 eq), AcOH (1 eq) followed by MnO₂ (8 eq). The reaction mixture was stirred at rt for 24 h, filtered on Celite and diluted with water. The mixture was extracted with CH₂Cl₂ (3×). The organic extracts were washed with brine, dried over MgSO₄, filtered and concentrated. The residue was purified by flash chromatography (hexane:EtOAc, 1:1) to afforded the title compound.

Step 2: 3-{6-[1-methyl-1-(methylsulfonyl)ethyl]quinolin-8-yl}benzoic acid

To a solution of ester from step 1 in THF (0.08M) was added LiOH (2N, 5 eq). The reaction mixture was stirred at rt for 5 h, acidified with AcOH, diluted with water and extracted with CH₂Cl₂. The organic extracts were washed with brine, dried over Na2SO4, filtered and concentrated. The title compound was isolated by filtration from Hexane/ether as a solid.

Step 3: 8-{3-[3-(4-fluorophenyl)-1,2,4-oxadiazol-5-yl]phenyl}-6-[1-methyl-1-(methylsulfonyl)ethyl]quinoline To a solution of acid from step 2 in DMF (0.05M) was added CDI (2 eq) and 4-fluoro-N'-hydroxybenzenecarboximidamide (2 eq). The reaction mixture was stirred at rt for 15 min and 18 h at 120° C. The reaction mixture cooled to rt, diluted with water and extracted with EtOAc. The organic extracts were washed with brine, dried over MgSO₄, filtered and concentrated. The residue was purified by flash chromatography (hexane:EtOAc, 20:80) to afforded the title compound.
¹H NMR (500 MHz, acetone-d₆): d 8.98 (dd, 1H), 8.64 (s, 1H), 8.55 (dd, 1H), 8.39 (d, 1H), 8.31 (d, 1H), 8.28 (d, 1H), 8.25 (dd, 2H), 8.08 (d, 1H), 7.82 (t, 1H), 7.63 (dd, 1H), 7.39 (t, 2H), 2.79 (s, 3H), 2.05 (s, 6H).
+ESI (M+1) 488.2.

EXAMPLE 134

6-[1-methyl-1-(methylsulfonyl)ethyl]-8-(3-{4-[4-(methylthio)phenyl]pyridin-3-yl}phenyl)quinoline

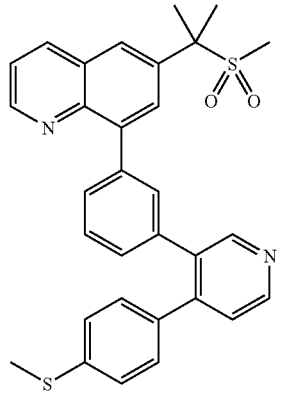

Step 1: 4-chloro-3-(tributylstannyl)pyridine

To a solution of LDA (1.1 eq) in THF (0.05M) at −78° C. was added 4-chloropyridine (1 eq). After 1.5 h tributyltin chloride (1.5 eq) was added and the reaction mixture was warmed to rt over 3 h. The reaction mixture was diluted with water and extracted with EtOAc. The organic extracts were washed with brine, dried over MgSO4, filtered and concentrated. The residue was purified by flash chromatography (hexane:EtOAc, 95:5) to afforded the title compound.
+ESI (M+1) 525.3

Step 2: 8-[3-(4-chloropyridin-3-yl)phenyl]-6-[1-methyl-1-(methylsulfonyl)ethyl]quinoline Prepared according to the general procedure Coupling_3 using Quinoline_3 and the Aryltin from step 1 as starting materials. Flash chromatography (CH₂Cl₂:MeOH, 99:1) afforded the title compound.

Step 3: 6-[1-methyl-1-(methylsulfonyl)ethyl]-8-(3-{4-[4-(methylthio)phenyl]pyridin-3-yl}phenyl)quinoline Prepared according to the general procedure Coupling_1 using 4-methylthiobenzeneboronic acid and the chloropyridine from step 2 as starting materials. Flash chromatography afforded the title compound.
¹H NMR (500 MHz, acetone-d₆): δ 8.91 (dd, 1H), 8.70 (s, 1H), 8.63 (d, 1H), 8.44 (dd, 1H), 8.27 (d, 1H), 7.92 (d, 1H), 7.76 (d, 1H), 7.58 (d, 1H), 7.56 (dd, 1H), 7.49 (t, 1H), 7.45 (d, 1H), 7.34 (d, 1H), 7.28 (d, 2H), 7.23 (d, 2H), 2.71 (s, 3H), 2.50 (s, 3H), 1.98 (s, 6H).
+ESI (M+1) 525.3

EXAMPLE 135

3''-{6-[1-methyl-1-(methylsulfonyl)ethyl]quinolin-8-yl}-1,1':2',1''-terphenyl-4-carboxylic acid

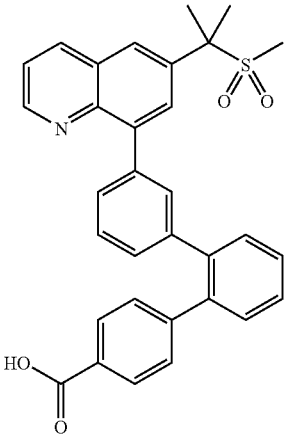

Step 1: 8-(2'-bromo-1,1'-biphenyl-3-yl)-6-[1-methyl-1-(methylsulfonyl)ethyl]quinoline Prepared according to the general procedure Coupling_1 using Quinoline_4 and 1,2-dibromobenzene as starting materials. Flash chromatography (hexane:EtOAc, 1:1) afforded the title compound.

Step 2: 3''-{6-[1-methyl-1-(methylsulfonyl)ethyl]quinolin-8-yl}-1,1':2',1''-terphenyl-4-carboxylic acid Prepared according to the general procedure Coupling_1 using Arylbromide from step 1 and 4-carboxybenzeneboronic acid as starting materials. Flash chromatography (CH₂Cl₂:MeOH, 9:1) afforded the title compound.
¹H NMR (500 MHz, acetone-d₆): δ 8.90 (dd, 1H), 8.43 (dd, 1H), 8.24 (d, 2H), 8.07 (d, 2H), 7.96 (d, 1H), 7.83 (d, 1H), 7.68 (d, 1H), 7.62 (d, 1H), 7.52 (m, 4H), 7.41 (d, 2H), 7.28 (d, 1H), 2.68 (s, 3H), 1.95 (s, 6H). −ESI (M−1) 520.4

EXAMPLE 136

2-(3-{6-[1-methyl-1-(methylsulfonyl)ethyl]quinolin-8-yl}phenyl)-3-[4-(methylsulfonyl)phenyl]quinoxaline

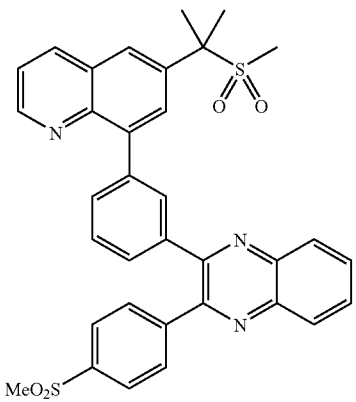

A solution of 2-bromo-2-(3-{6-[1-methyl-1-(methylsulfonyl)ethyl]quinolin-8-yl}phenyl)-1-[4-(methylsulfonyl)phenyl]ethanone from EXAMPLE 1, step 4 in DMF (0.05M) and 1,2-diaminobenzene (2 eq) was stirred at 130° C. for 18 h. The reaction mixture was cooled to rt, diluted with water and extracted with EtOAc. The organic extracts were washed with brine, dried over MgSO$_4$, filtered and concentrated. The residue was purified by flash chromatography (hexane:EtOAc, 1:1) to afforded the title compound.

$^1$H NMR (500 MHz, acetone-d$_6$): δ 8.89 (dd, 1H), 8.43 (dd, 1H), 8.29 (d, 1H), 8.21 (m, 2H), 8.05 (d, 1H), 8.00 (d, 2H), 7.96 (d, 2H), 7.95 (m, 3H), 7.85 (d, 1H), 7.70 (d, 1H), 7.58 (m, 2H), 3.10 (s, 3H), 2.72 (s, 3H), 1.99 (s, 6H).

EXAMPLE 137

6-[1-methyl-1-(methylsulfonyl)ethyl]-8-(3-{3-[4-(methylsulfonyl)phenyl]pyrazin-2-yl}phenyl)quinoline

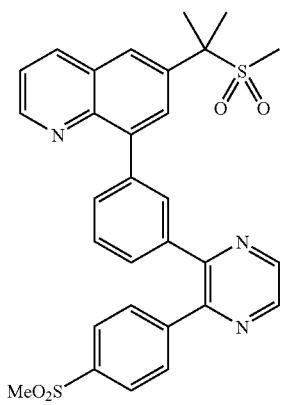

Step 1: 8-[3-(3-chloropyrazin-2-yl)phenyl]-6-[1-methyl-1-(methylsulfonyl)ethyl]quinoline Prepared according to the general procedure Coupling_1 using Quinoline_4 and 1,2-dichloropyrazine as starting materials. Flash chromatography (hexane:EtOAc, 3:7) afforded the title compound.

Step 2: 6-[1-methyl-1-(methylsulfonyl)ethyl]-8-(3-{3-[4-(methylthio)phenyl]pyrazin-2-yl}phenyl)quinoline Prepared according to the general procedure Coupling_1 using 4-methylthiobenzeneboronic acid and the chloropyrazine from step 1 as starting materials. Flash chromatography (hexane:EtOAc, 2:8) afforded the title compound.

Step 3: 6-[1-methyl-1-(methylsulfonyl)ethyl]-8-(3-{3-[4-(methylsulfonyl)phenyl]pyrazin-2-yl}phenyl)quinoline Prepared according to the general procedure Oxid-1 using thioether from step 2 as starting material. Flash chromatography (hexane:EtOAc, 2:8) afforded the title compound.

$^1$H NMR (500 MHz, DMSO-d$_6$): δ 8.86 (dd, 1H), 8.78 (d, 1H), 8.75 (d, 1H), 8.45 (dd, 1H), 8.27 (d, 1H), 8.02 (d, 1H), 7.94 (d, 2H), 7.85 (d, 2H), 7.83 (m, 2H), 7.60 (m, 1H), 7.39 (m, 1H), 7.25 (t, 1H), 3.09 (s, 3H), 2.71 (s, 3H), 1.98 (s, 6H). +ESI (M+1) 558.1

The following compounds (Table 4) were prepared according to the procedure described previously. Indicated is their respective (M+1)$^+$ value obtained from a low resolution mass spectrometer under electron-spray ionization conditions.

TABLE 4

| EX. | Chemical name | ESI-LRMS (M + 1)$^+$ |
|---|---|---|
| 138 | 6-[1-methyl-1-(methylsulfonyl)ethyl]-8-(3-{4-[4-(methylsulfonyl)phenyl]pyridin-3-yl}phenyl)quinoline | 557.1 |
| 139 | 6-[1-methyl-1-(methylsulfonyl)ethyl]-8-(3-{4-[4-(methylsulfonyl)phenyl]-1-oxidopyridin-3-yl}phenyl)quinoline | 573.3 |
| 140 | 6-[1-methyl-1-(methylsulfonyl)ethyl]-8-(3-{4-[3-(methylthio)phenyl]pyridin-3-yl}phenyl)quinoline | 525.0 |
| 141 | 8-[4',5'-difluoro-4''-(methylthio)-1,1':2',1''-terphenyl-3-yl]-6-[1-methyl-1-(methylsulfonyl)ethyl]quinoline | 560.1 |
| 142 | 8-[4',5'-difluoro-4''-(methylsulfonyl)-1,1':2',1''-terphenyl-3-yl]-6-[1-methyl-1-(methylsulfonyl)ethyl]quinoline | 591.8 |
| 143 | 8-(4''-fluoro-1,1':2',1''-terphenyl-3-yl)-6-[1-methyl-1-(methylsulfonyl)ethyl]quinoline | 496.1 |
| 144 | 6,7-dichloro-2-(3-{6-[1-methyl-1-(methylsulfonyl)ethyl]quinolin-8-yl}phenyl)-3-[4-(methylsulfonyl)phenyl]quinoxaline | 676.1 |
| 145 | 2-(4-chlorophenyl)-3-(3-{6-[1-methyl-1-(methylsulfonyl)ethyl]quinolin-8-yl}phenyl)quinoxaline | 564.1 |
| 146 | 2-{4-[3-(3-{6-[1-methyl-1-(methylsulfonyl)ethyl]quinolin-8-yl}phenyl)quinoxalin-2-yl]phenyl}propan-2-ol | 588.0 |
| 147 | 2-[3,4-bis(difluoromethoxy)phenyl]-3-(3-{6-[1-methyl-1-(methylsulfonyl)ethyl]quinolin-8-yl}phenyl)quinoxaline | 662.0 |
| 148 | 4-[3-(3-{6-[1-methyl-1-(methylsulfonyl)ethyl]quinolin-8-yl}phenyl)quinoxalin-2-yl]benzoic acid | 574.3 |
| 149 | N-cyclopropyl-4-[3-(3-{6-[1-methyl-1-(methylsulfonyl)ethyl]quinolin-8-yl}phenyl)quinoxalin-2-yl]benzamide | 613.4 |
| 150 | 2-(3-{6-[1-methyl-1-(methylsulfonyl)ethyl]quinolin-8-yl}phenyl)-3-(4-methylphenyl)quinoxaline | 544.2 |

TABLE 4-continued

| EX. | Chemical name | ESI-LRMS (M + 1)+ |
|---|---|---|
| 151 | 2-(3-{6-[1-methyl-1-(methylsulfonyl)ethyl]quinolin-8-yl}phenyl)-3-phenylquinoxaline | 530.2 |
| 152 | 2-(4-fluorophenyl)-3-(3-{6-[1-methyl-1-(methylsulfonyl)ethyl]quinolin-8-yl}phenyl)quinoxaline | 548.8 |
| 153 | 2-{4-[3-(3-{6-[1-methyl-1-(methylsulfonyl)ethyl]quinolin-8-yl}phenyl)pyrazin-2-yl]phenyl}propan-2-ol | 536.8 |
| 154 | 6-[1-methyl-1-(methylsulfonyl)ethyl]-8-(3-{3-[4-(methylthio)phenyl]pyrazin-2-yl}phenyl)quinoline | 526.3 |
| 155 | 8-{3-[3-(4-fluorophenyl)pyrazin-2-yl]phenyl}-6-[1-methyl-1-(methylsulfonyl)ethyl]quinoline | 498.2 |
| 156 | 8-(3-{2-(2-ethylpyridin-4-yl)-4-[4-(methylsulfonyl)phenyl]-1,3-thiazol-5-yl}phenyl)-6-[1-methyl-1-(methylsulfonyl)ethyl]quinoline | 668.3 |
| 157 | 2-(4-{5-(3-{6-[1-methyl-1-(methylsulfonyl)ethyl]quinolin-8-yl}phenyl)-4-[4-(methylsulfonyl)phenyl]-1,3-thiazol-2-yl}phenyl)propan-2-ol | 697.5 |

EXAMPLE 158

5-(3-{6-[1-methyl-1-(methylsulfonyl)ethyl]quinolin-8-yl}phenyl)-6-[4-(methylsulfonyl)phenyl]pyridin-2(1H)-one

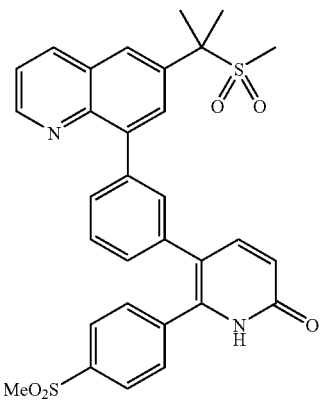

To a suspension of ketone from EXAMPLE 1, step 3 in MeOH (0.15M) at 0° C. was condensed NH₃ (30% volume) and added methyl propiolate (6 eq). The reaction mixture was heated in a pressure tube at 150° C. for 5 h, cooled to rt and concentrated to dryness. The residue was purified by flash chromatography (EtOH:EtOAc, 12:88) to afforded the title compound.

$^1$H NMR (500 MHz, acetone-$d_6$): δ 11.15 (br s, 1H), 8.87 (dd, 1H), 8.41 (dd, 1H), 8.23 (d, 1H), 7.95 (d, 1H), 7.88 (dd, 2H), 7.72 (d, 1H), 7.69 (dd, 2H), 7.63 (dt, 2H), 7.53 (m, 2H), 7.38 (t, 1H), 7.18 (dt, 1H), 6.59 (d, 1H), 3.04 (s, 3H), 2.69 (s, 3H), 1.94 (s, 6H).

EXAMPLE 159

1-methyl-5-(3-{6-[1-methyl-1-(methylsulfonyl)ethyl]quinolin-8-yl}phenyl)-6-[4-(methylsulfonyl)phenyl]pyridin-2(1H)-one

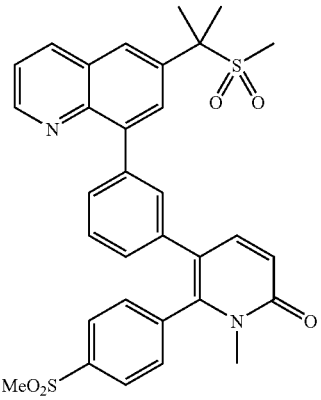

To a solution of EXAMPLE 158 in DMF (0.05M) at 0° C. was added NaH (1.1 eq) followed by MeI (6 eq). The reaction mixture was stirred at rt for 1 h, diluted with NH₄Cl solution and extracted with EtOAc. The organic extracts were washed with brine, dried over MgSO₄, filtered and concentrated. The residue was purified by flash chromatography (hexane:EtOAc, 70:30, then EtOH:EtOAc, 12:88) to afforded the title compound and EXAMPLE 160.

$^1$H NMR (500 MHz, acetone-$d_6$): δ 8.94 (dd, 1H), 8.45 (dd, 1H), 8.26 (d, 1H), 7.97 (m, 3H), 7.74 (d, 2H), 7.59 (m, 3H), 7.46 (t, 1H), 7.30 (t, 1H), 7.12 (d, 1H), 6.60 (d, 1H), 3.26 (s, 3H), 3.00 (s, 3H), 2.74 (s, 3H), 2.00 (s, 6H).

EXAMPLE 160

8-(3-{6-methoxy-2-[4-(methylsulfonyl)phenyl]pyridin-3-yl}phenyl)-6-[1-methyl-1-(methylsulfonyl)ethyl]quinoline

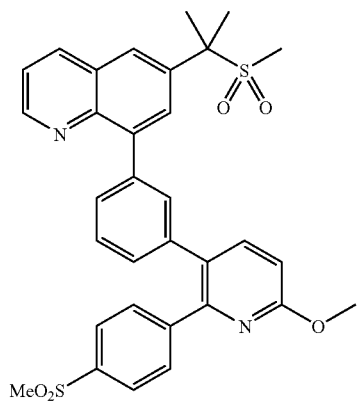

Prepared according to the procedure described for EXAMPLE 159.

$^1$H NMR (500 MHz, acetone-$d_6$): δ 8.89 (dd, 1H), 8.44 (dd, 1H), 8.26 (d, 1H), 8.00 (d, 1H), 7.90 (d, 1H), 7.87 (d, 2H), 7.79 (d, 2H), 7.71 (dt, 1H), 7.61 (t, 1H), 7.56 (dd, 1H), 7.48 (t, 1H), 7.29 (dt, 1H), 6.96 (d, 1H), 4.03 (s, 3H), 3.10 (s, 3H), 2.71 (s, 3H), 1.97 (s, 6H).

EXAMPLE 161

8-(3-{6-(difluoromethoxy)-2-[4-(methylsulfonyl)phenyl]pyridin-3-yl}phenyl)-6-[1-methyl-1-(methylsulfonyl)ethyl]quinoline

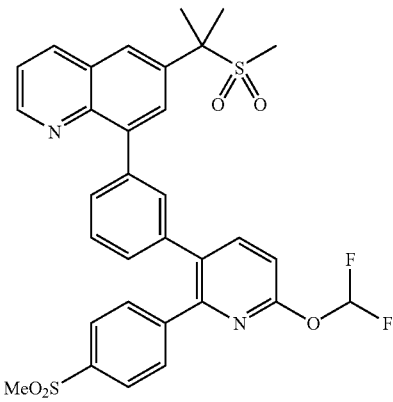

Prepared according to procedure described for EXAMPLE 159 but using ethyl bromodifluoroacetate as electrophile. Flash chromatography (hexane:EtOAc, 70:30, then EtOH:EtOAc, 12:88) afforded the title compound.

$^1$H NMR (500 MHz, acetone-$d_6$): δ 8.89 (dd, 1H), 8.45 (dd, 1H), 8.27 (d, 1H), 8.13 (d, 1H), 8.01 (d, 1H), 7.89 (d, 2H), 7.87 (t, 1H), 7.80 (d, 2H), 7.76 (dt, 1H), 7.65 (t, 1H), 7.57 (dd, 1H), 7.51 (t, 1H), 7.34 (dt, 1H), 7.22 (d, 2H), 3.11 (s, 3H), 2.71 (s, 3H), 1.97 (s, 6H).

EXAMPLE 162

8-(3-{6-[(4-fluorobenzyl)oxy]-2-[4-(methylsulfonyl)phenyl]pyridin-3-yl}phenyl)-6-[1-methyl-1-(methylsulfonyl)ethyl]quinoline

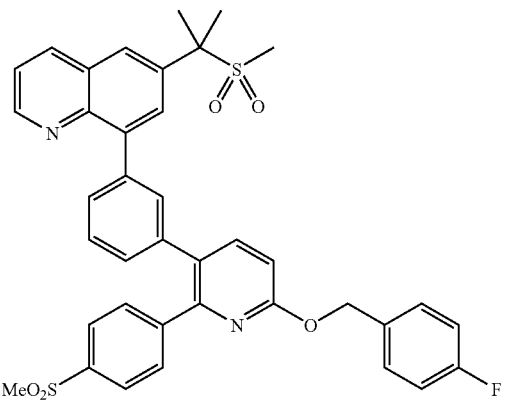

Prepared according to procedure described for EXAMPLE 159 but using 4-fluorobenzyl bromide as electrophile. Flash chromatography (hexane:EtOAc, 70:30, EtOH:EtOAc, 12:88, EtOH:EtOAc, 5:95) afforded the title compound and EXAMPLE 162.

$^1$H NMR (500 MHz, acetone-$d_6$): δ 8.89 (dd, 1H), 8.44 (dd, 1H), 8.26 (d, 1H), 8.01 (d, 1H), 7.92 (d, 1H), 7.88 (d, 2H), 7.78 (d, 2H), 7.72 (dt, 1H), 7.61 (m, 3H), 7.56 (dd, 1H), 7.47 (t, 1H), 7.30 (dt, 1H), 7.19 (t, 2H), 7.02 (d, 1H), 5.53 (s, 2H), 3.10 (s, 3H), 2.71 (s, 3H), 1.97 (s, 6H).

EXAMPLE 163

1-(4-fluorobenzyl)-5-(3-{6-[1-methyl-1-(methylsulfonyl)ethyl]quinolin-8-yl}phenyl)-6-[4-(methylsulfonyl)phenyl]pyridin-2(1H)-one

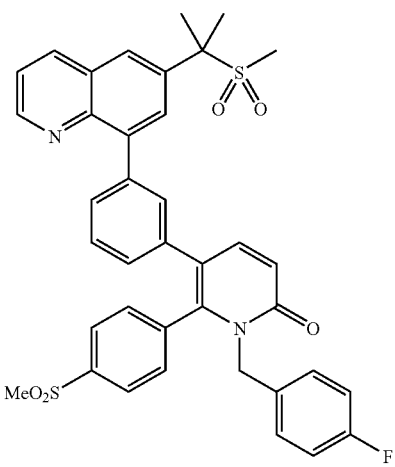

Prepared according to the procedure described for EXAMPLE 162.

$^1$H NMR (500 MHz, acetone-$d_6$): δ 8.93 (dd, 1H), 8.44 (dd, 1H), 8.25 (d, 1H), 7.92 (d, 1H), 7.82 (d, 2H), 7.68 (d, 1H), 7.57 (m, 2H), 7.47 (d, 2H), 7.43 (s, 1H), 7.29 (t, 1H), 7.14 (d, 2H), 6.98 (t, 2H), 6.92 (m, 2H), 6.73 (d, 1H), 5.18 (br s, 2H), 2.99 (s, 3H), 2.73 (s, 3H), 1.98 (s, 6H).

EXAMPLE 164

5-(4-fluorophenyl)-6-(3-{6-[1-methyl-1-(methylsulfonyl)ethyl]quinolin-8-yl}phenyl)pyridin-2(1H)-one

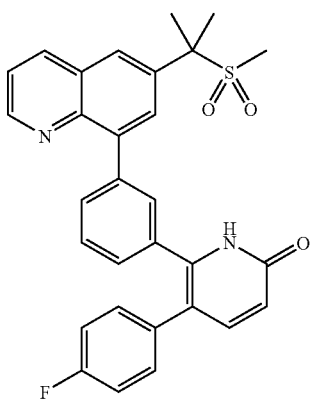

Step 1: 2-(4-fluorophenyl)-1-(3-{6-[1-methyl-1-(methylsulfonyl)ethyl]quinolin-8-yl}phenyl)ethanone Prepared according to the procedure described for EXAMPLE 1, step 1-2, using Quinoline_2 in step 1 and 4-fluorobenzaldehyde in step 2. Flash chromatography (Hexane:EtOAc, 40:60) afforded the title compound.

Step 2: 5-(4-fluorophenyl)-6-(3-{6-[1-methyl-1-(methylsulfonyl)ethyl]quinolin-8-yl}phenyl)pyridin-2(1H)-one Prepared according to the procedure described for EXAMPLE 158. Flash chromatography (EtOH:EtOAc, 12:88) afforded the title compound.

$^1$H NMR (500 MHz, Acetone/Chlooroform=2:1): δ 8.89 (dd, 1H), 8.39 (dd, 1H), 8.22 (d, 1H), 7.88 (s, 1H), 7.79 (d, 2H), 7.62 (s, 1H), 7.57 (d, 1H), 7.54 (dd, 1H), 7.46 (t, 1H), 7.38 (d, 1H), 7.22 (m, 2H), 7.02 (t, 2H), 6.52 (d, 2H), 2.67 (s, 3H), 1.96 (s, 6H).

EXAMPLE 165

5-(4-fluorophenyl)-1-methyl-6-(3-{6-[1-methyl-1-(methylsulfonyl)ethyl]quinolin-8-yl}phenyl)pyridin-2(1H)-one

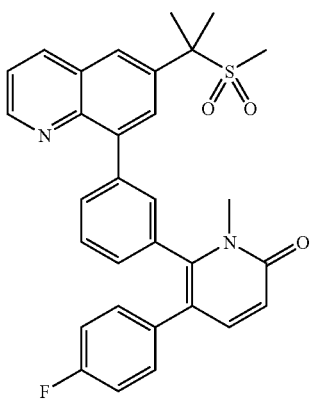

Prepared according to the procedure described for EXAMPLE 159 using EXAMPLE 164 as starting material. The residue was purified by flash chromatography (hexane:EtOAc, 60:40, then EtOH:EtOAc, 8:92) to afforded the title compound and EXAMPLE 166.

$^1$H NMR (500 MHz, acetone-d$_6$): δ 8.97 (dd, 1H), 8.47 (dd, 1H), 8.31 (d, 1H), 8.05 (d, 1H), 7.98 (s, 1H), 7.80 (s, 1H), 7.77 (d, 1H), 7.60 (dd, 1H), 7.50 (m, 2H), 7.31 (d, 1H), 7.26 (m, 2H), 6.98 (t, 2H), 6.54 (d, 2H), 3.38 (s, 3H), 2.73 (s, 3H), 2.01 (s, 3H), 1.99 (s, 3H).

EXAMPLE 166

8-{3-[3-(4-fluorophenyl)-6-methoxypyridin-2-yl]phenyl}-6-[1-methyl-1-(methylsulfonyl)ethyl]quinoline

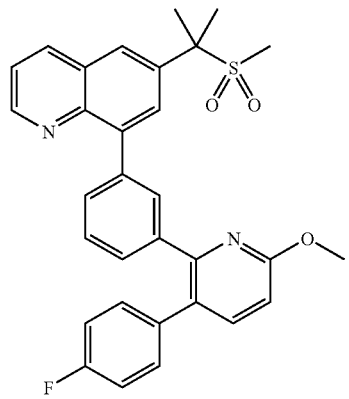

Prepared according to the procedure described for EXAMPLE 165.

$^1$H NMR (500 MHz, acetone-d$_6$): δ 8.90 (dd, 1H), 8.44 (dd, 1H), 8.27 (dd, 1H), 7.96 (dd, 1H), 7.80 (t, 1H), 7.75 (d, 1H), 7.72 (dt, 1H), 7.57 (dd, 1H), 7.48 (dt, 1H), 7.41 (t, 1H), 7.32 (m, 2H), 7.11 (t, 2H), 6.87 (d, 1H), 4.01 (s, 3H), 2.70 (s, 3H), 1.98 (s, 6H).

EXAMPLE 167

N-cyclopropyl-8-(3-{2-(1-hydroxy-1-methylethyl)-4-[4-(methylsulfonyl)phenyl]-1,3-thiazol-5-yl}phenyl)quinoline-6-carboxamide

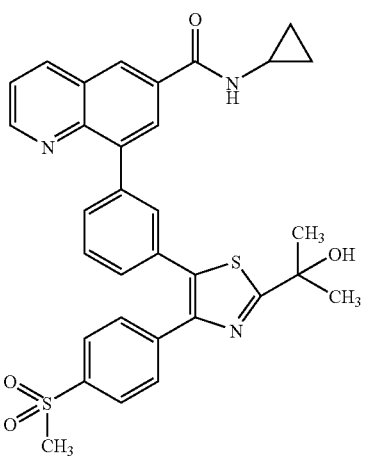

Step 1: 2-{5-(3-bromophenyl)-4-[4-(methylsulfonyl)phenyl]-1,3-thiazol-2-yl}propan-2-ol Prepared according to the procedure described for EXAMPLE 71 using 3-bromo benzaldehyde as precursor. Flash chromatography (Hexane:EtOAc, 50:50-20:80) afforded the title compound.

Step 2: 2-{5-[3-(4,4,5,5-tetramethyl-[1,3,2]diox-aborolan-2-yl)-phenyl-4-[4-(methylsulfonyl)phenyl]-1,3-thiazol-2-yl}propan-2-ol Prepared according to the procedure described for Quinoline_4 using bromide from step 1. Flash chromatography (Hexane:EtOAc, 50:50) afforded the title compound.

Step 3: N-cyclopropyl-8-(3-{2-(1-hydroxy-1-methyl-ethyl)-4-[4-(methylsulfonyl)phenyl]-1,3-thiazol-5-yl}phenyl)quinoline-6-carboxamide Prepared according to the procedure Coupling-1 using boronic ester from step 2 and Quinoline_5 as starting material. Flash chromatography (Hex:EtOAc; 10:90) afforded the title compound.

$^1$H NMR (500 MHz, acetone-d$_6$): δ 8.94 (dd, 1H), 8.48 (br s, 1H), 8.45 (d, 1H), 8.22 (d, 1H), 8.16 (s, NH), 7.94 (m, 4H), 7.81 (m, 2H), 7.62 (t, 1H), 7.59 (d, 1H), 7.50 (d, 1H), 5.21 (s, OH), 3.19 (s, 3H), 3.00 (s, 1H), 1.71 (s, 6H), 0.80 (m, 2H), 0.68 (m, 2H).

EXAMPLE 168

8-(3-{2-(1-hydroxy-1-methylethyl)-4-[4-(methylsulfonyl)phenyl]-1,3-thiazol-5-yl}phenyl)quinoline-6-carboxylic acid

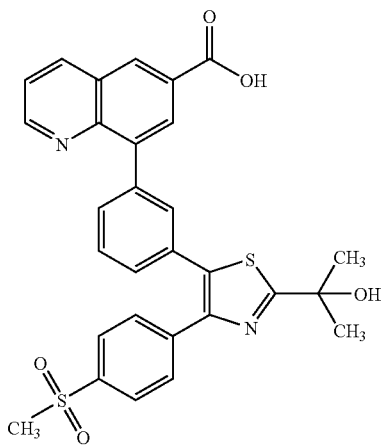

Prepared according to the procedure Coupling-1 using boronic ester from EXAMPLE 167, step 2 and 8-bromo-quinoline-6-carboxylic acid from Quinoline_5, step 1 as starting material. Flash chromatography (CH$_2$Cl$_2$:MeOH; 90:10) afforded the title compound.

$^1$H NMR (500 MHz, CD$_3$OD): δ 9.35 (d, 1H), 9.17 (dd, 1H), 9.03 (br s, 1H), 8.43 (br s, 1H), 8.18 (m, 1H), 7.93 (d, 2H), 7.87 (d, 2H), 7.69 (m, 4H), 3.40 (s, OH), 3.17 (s, 3H), 1.71 (s, 6H). +ESI, Q1 (M+1) 545.2

EXAMPLE 169

2-[4-[4-(methylsulfonyl)phenyl]-5-(3-{6-[1-methyl-1-(1H-tetraazol-5-yl)ethyl]quinolin-8-yl}phenyl)-1,3-thiazol-2-yl]propan-2-ol

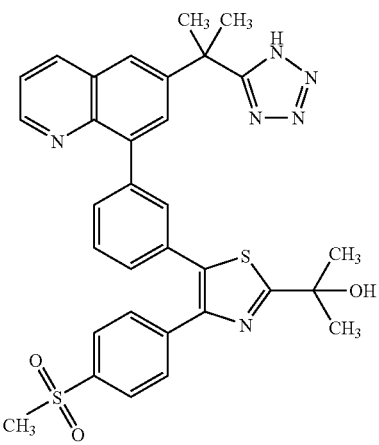

Step 1: 8-bromo-6-[1-methyl-1-(1H-tetraazol-5-yl)ethyl]quinoline

To a solution of Quinoline_6 in Xylenes (0.2M) was added tributyltin chloride (5 eq) and sodium azide (5 eq). The reaction mixture was stirred at 135° C. for 2 days. The reaction mixture was diluted with NaOH 5N and the solid isolated by filtration washing with benzene/hexane. The material was suspended and stirred in MeOH/Et$_2$O and the title product isolated by filtration.

Step 2: 2-[4-[4-(methylsulfonyl)phenyl]-5-(3-{6-[1-methyl-1-(1H-tetraazol-5-yl)ethyl]quinolin-8-yl}phenyl)-1,3-thiazol-2-yl]propan-2-ol Prepared according to the procedure Coupling-1 using boronic ester from EXAMPLE 167, step 2 and tetrazole from step 1 as starting material. Flash chromatography (CH$_2$Cl$_2$:MeOH:NH$_4$OH; 90:10:5) afforded the title compound.

$^1$H NMR (500 MHz, acetone-d$_6$): δ 8.82 (dd, 1H), 8.33 (dd, 1H), 7.93 (m, 4H), 7.87 (d, 1H), 7.76 (br s, 1H), 7.72 (d, 1H), 7.69 (d, 1H), 7.50 (m, 2H), 7.42 (d, 1H), 5.51 (br s, NH), 3.32 (s, OH), 3.15 (s, 3H), 1.98 (s, 6H), 1.71 (s, 6H). +ESI, Q1 (M+1) 611.3

EXAMPLE 170

1,1,1,3,3,3-hexafluoro-2-[8-(3-{2-(1-hydroxy-1-methylethyl)-4-[4-(methylsulfonyl)phenyl]-1,3-thiazol-5-yl}phenyl)quinolin-6-yl]propan-2-ol

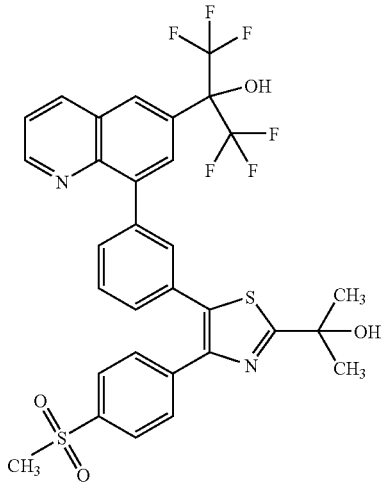

Step 1:
3-bromo-4-(hexafluoro-2-hydroxyisopropyl)aniline

To a solution of 4-(hexafluoro-2-hydroxyisopropyl)aniline in DMF (0.08M) was added NBS (1.1 eq). The reaction mixture was stirred at rt for 1 h, diluted with water and extracted with EtOAc. The organic extracts were washed with brine, dried over MgSO$_4$, filtered and concentrated to afford the title compound.

Step 2: 2-(8-bromoquinolin-6-yl)-1,1,1,3,3,3-hexafluoropropan-2-ol

Prepared according to the procedure described for Quinoline-5, step 1 using aniline from step 1 as starting material. Flash chromatography (Hex:EtOAc; 80:20 to 50:50) afforded the title compound.

Step 3: 1,1,1,3,3,3-hexafluoro-2-[8-(3-{2-(1-hydroxy-1-methylethyl)-4-[4-(methylsulfonyl)phenyl]-1,3-thiazol-5-yl}phenyl)quinolin-6-yl]propan-2-ol Prepared according to the procedure Coupling-1 using boronic ester from EXAMPLE 167, step 2 and quinoline from step 1 as starting material. Flash chromatography (Hex: EtOAc; 80:20 to 50:50) afforded the title compound.

$^1$H NMR (500 MHz, acetone-d$_6$): δ 8.98 (d, 1H), 8.60 (d, 1H), 8.46 (s, 1H), 8.13 (s, 1H), 7.94 (m, 4H), 7.82 (m, 2H), 7.66 (dd, 1H), 7.61 (t, 1H), 7.51 (d, 1H), 5.21 (s, OH), 3.12 (s, 3H), 2.87 (s, OH), 2.05 (s, 3H), 1.72 (s, 6H). +ESI, Q1 (M+1) 667.4

What is claimed is:
1. A compound represented by Formula (I):

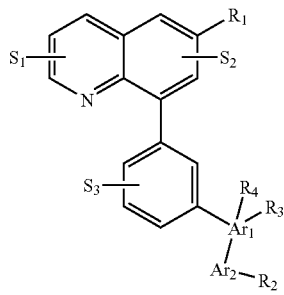

or a pharmaceutically acceptable salt, wherein
S$_1$, S$_2$, and S$_3$ are independently
1. H,
2. —OH,
3. halogen,
4. —C$_1$-C$_6$alkyl,
5. —O—C$_1$-C$_6$alkyl optionally substituted with 1, 2 or 3 halogens, or —CN;

R$_1$ is
1. —(C$_1$-C$_6$alkyl)-SO$_n$—(C$_1$-C$_6$alkyl) group, optionally substituted with 1, 2 or 3 substituents; wherein each substituent is independently a halogen, —OH and —CN,
2. —C(O)—O-aryl,
3. —C(O)—NH-aryl,
4. —C(O)—NH-heterocycle or N-oxide thereof,
5. —C(O)—NH—C$_1$-C$_6$alkyl,
6. —C(O)—NH-cycloC$_3$-C$_6$alkyl,
7. —C$_1$-C$_6$alkyl, optionally substituted with 1 to 6 halogens and 1 hydroxy,
8. —COOH,
9. —C$_1$-C$_6$alkyl-COOH,
10. —O—C$_1$-C$_6$alkyl,
11. -cycloC$_3$-C$_6$alkyl,
12. —C$_3$-C$_6$alkyl-heterocycle,
13. aryl,
14. heterocycle,
15. carbonyl,
16. carbamoyl, or
17. —SO$_n$—(C$_1$-C$_6$alkyl);
each n is independently 0, 1, or 2;
Ar$_1$ and Ar$_2$ are each independently an aryl or heterocycle or an N-oxide thereof;
R$_2$ is
1. Hydrogen,
2. aryl optionally substituted with 1, 2 or 3 substituents selected from halogen,
3. heterocycle optionally substituted with 1, 2 or 3 halogens,
4. —C$_1$-C$_6$alkyl optionally substituted with 1, 2 or 3 substituents selected from hydroxy and halogen,
5. —COOH,
6. 1, 2 or 3 halogens,
7. —SO$_n$—(C$_1$-C$_6$alkyl),
8. —N(H)—S(O)$_n$—C$_1$-C$_6$alkyl,
9. —O—C$_1$-C$_6$alkyl substituents each optionally substituted with 1, 2 or 3 halogens,
10. —C(O)—N(H)—C$_3$-C$_6$cycloalkyl, or
11. —C(O)—C$_1$-C$_6$alkyl;

R₃ is
1. Hydrogen,
2. —$C_1$-$C_6$alkyl optionally substituted with hydroxy, —S(O)$_n$$C_1$-$C_6$alkyl, heterocycle, or 1, 2, 3, 4, 5 or 6 halogens,
3. aryl or $C_6$-$C_{12cyclo}$alkyl optionally substituted with phenyl, —$C_1$-$C_6$alkyl, —S(O)$_n$$C_1$-$C_6$alkyl, —C(O)—O—$C_1$-$C_6$alkyl, —COOH, hydroxy-$C_1$-$C_6$alkyl- or 1, 2 or 3 halogens,
4. heterocycle or optionally substituted with 1, 2 or 3 substituents independently selected from phenyl, halogen, $C_1$-$C_6$alkyl, hydroxy$C_1$-$C_6$alkyl, —COOH, —C(O)—O—$C_1$-$C_6$alkyl,
5. amino,
6. —C(O)—O—$C_1$-$C_6$alkyl,
7. —$C_1$-$C_6$alkyl-O-phenyl optionally substituted with 1, 2 or 3 halogens,
8. —$C_1$-$C_6$alkyl-phenyl optionally substituted with 1 or 2 substituents selected from hydroxy and halo,
9. —COOH,
10. Halogen,
11. —SO$_n$—($C_1$-$C_6$alkyl),
12. —N(H)—S(O)$_n$—$C_1$-$C_6$alkyl optionally substituted with 1, 2 or 3 halogen,
13. —N(H)—C(O)—$C_1$-$C_6$alkyl,
14. —N(H)-heterocycle optionally substituted with 1, 2 or 3 halogens,
15. —N(H)-aryl optionally substituted with 1, 2 or 3 halogens,
16. —N(H)—$C_1$-$C_6$alkyl optionally substituted with 1, 2 or 3 halogens,
17. —C(O)—N(H)—$C_1$-$C_6$alkyl optionally substituted with 1, 2 or 3 halogens,
18. —C(O)—NH—$C_3$-$C_6$cycloalkyl,
19. —O—$C_1$-$C_6$alkyl optionally substituted with 1, 2 or 3 halogens or phenyl optionally substituted with 1, 2, or 3 halogen;
R₄ is
1. H,
2. Halogen,
3. —CN
4. —$C_1$-$C_6$alkyl,
5. —O—$C_1$-$C_6$alkyl optionally substituted with 1, 2 or 3 halogens,
6. —$C_1$-$C_6$alkyl-phenyl with phenyl optionally substituted with halogen, or
7. Oxo.

2. A compound according to claim 1, or a pharmaceutically acceptable salt thereof, wherein
Ar₁ is pyridine or pyridinone or an N-oxide thereof.

3. A compound according to claim 2, or a pharmaceutically acceptable salt thereof, wherein
Ar₂ is phenyl, oxadiazole or thiadiazole.

4. A compound according to claim 3, or a pharmaceutically acceptable salt thereof, wherein
R₁ is —($C_1$-$C_6$alkyl)-SO$_n$—($C_1$-$C_6$alkyl); and
R2 is —SO$_n$—$C_1$-$C_6$alkyl.

5. A compound according to claim 1, or a pharmaceutically acceptable salt thereof, wherein
Ar₁ is phenyl.

6. A compound according to claim 5, or a pharmaceutically acceptable salt thereof, wherein
Ar₂ is phenyl, oxadiazole, thiadiazole, pyridine or pyridinone or an N-oxide thereof.

7. A compound according to claim 6, or a pharmaceutically acceptable salt thereof, wherein
R₁ is —($C_1$-$C_6$alkyl)-SO$_n$—($C_1$-$C_6$alkyl); and
R2 is —SO$_n$—$C_1$-$C_6$alkyl.

8. A compound according to claim 1, or a pharmaceutically acceptable salt thereof, wherein
Ar₁ is thiazole or oxazole.

9. The compound according to claim 8, or a pharmaceutically acceptable salt thereof, wherein
Ar₂ is phenyl, pyridine or pyridinone or an N-oxide thereof.

10. The compound according to claim 9, or a pharmaceutically acceptable salt thereof, wherein
R₁ is —($C_1$-$C_6$alkyl)-SO$_n$—($C_1$-$C_6$alkyl); and
R2 is —SO$_n$—$C_1$-$C_6$alkyl.

11. The compound according to claim 1 of Formula Ia

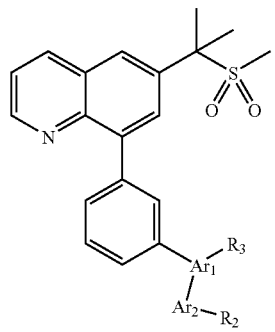

Ia or a pharmaceutically acceptable salt thereof, wherein:
Ar₁ is phenyl, pyridine, pyridinone, pyrimidyl, thiophene, thiazole, triazole, tetrazole, oxazole, thiaphendiazole, pyridindiazole, imidazothiazole or quinoxaline or an N-oxide thereof; and
Ar₂ is phenyl, pyridine, pyridinone, oxadiazole or thiadiazole or an N-oxide thereof.

12. A compound according to claim 11, or a pharmaceutically acceptable salt thereof, wherein:
R₂ is phenyl, —COOH, —$C_1$-$C_6$alkyl, —$C_1$-$C_6$alkoxy, mono or di-halo-$C_1$-$C_6$alkoxy, hydroxy$C_1$-$C_6$alkyl, or —SO$_n$—($C_1$-$C_6$alkyl) or 1, 2 or 3 halogens.

13. A compound according to claim 12, or a pharmaceutically acceptable salt thereof, wherein:
R₃ is Hydrogen, amino, biphenyl, N-(tert-butoxycarbonyl)-4-phenylpyrrolidin-3-yl, N-(tert-butoxycarbonyl)azetidin-3-yl, N-(tert-butoxycarbonyl)pyrrolidin-3-yl, 3-chloro-4-fluorophenyl, 4-chlorophenoxymethyl, 2-chlorophenyl, 4-chlorophenyl, ethoxycarbonyl, furan-2-yl, furan-3-yl, imidazol-2-yl, indan-1-yl, indan-2-yl, 1H-indol-2-yl, 1H-indol-3-yl, 1H-indol-4-yl, 1H-indol-5-yl, 1H-indol-6-yl, 1H-indol-7-yl, isoquinolin-1-yl, isoquinolin-4-yl, isoquinolin-5-yl, isoquinolin-8-yl, isoxazol-3-yl, 3-methoxycarbonylphenyl, 4-methoxycarbonylphenyl, methyl, 1-methyl-1Hpyrazol-3-yl, 1-methyl-1Hpyrazol-4-yl, 1-methyl-1Hpyrazol-5-yl, 2-methylphenyl, 3-methylphenyl, 4-methylphenyl, 2-methylpyridin-5-yl, methylsulfonylmethyl, 2-methylsulfonylphenyl, 3-methylsulfonylphenyl, 4-methylsulfonylphenyl, morpholin-4-ylmethyl, phenyl, pyrazinyl, 1Hpyrazol-3-yl, pyridin-2-yl, pyridin-3-yl, pyridin-4-yl, 3-pyridinylmethyl, pyrimidin-2-yl, pyrimidin-4-yl, pyrimidin-5-yl, quinolin-4-yl, quinolin-5-yl, quinolin-8-yl, 5,6,7,8-tetrahydro-1,8-naphthyridin-2-yl, 5,6,7,8-tetrahydro-5Hbenzo[a][7]annulen-5-yl, 5,6,7,8-tetrahydro-5Hbenzo[a][7]annulen-6-yl, tetrahydrofuran-2-yl, 1,2,3,4-tetrahydronaphthalen-1-yl, 1,2,3,4-tetrahydronaphthalen-2-yl, 1,3-thiazol-2-yl, 1,3-thiazol-5-yl, thiophen-2-yl and thiophen-2-yl.

14. A compound according to claim 11, or a pharmaceutically acceptable salt thereof, wherein:
$Ar_1$ is thiazole;
$Ar_2$ is phenyl; and
$R_2$ is —$SO_2$—$C_1$-$C_6$alkyl or halogen or $C_1$-$C_6$alkyl optionally substituted with hydroxy or 1-3 halogens.

15. A compound according to claim 14 or a pharmaceutically acceptable salt thereof, wherein:
$R_3$ is Hydrogen or —$C_1$-$C_6$alkyl optionally substituted with hydroxy, —$S(O)_n C_1$-$C_6$alkyl, or 1-6 halogens.

16. A compound according to claim 11, or a pharmaceutically acceptable salt thereof, wherein
$Ar_1$ is pyridine or an N-oxide thereof;
$Ar_2$ is oxadiazole; and
$R_2$ is
1. —$C_1$-$C_6$alkyl optionally substituted with hydroxy, —$S(O)_n C_1$-$C_6$alkyl, or 1-3 substituents halogens,
2. —N(H)—C(O)—$C_1$-$C_6$alkyl,
3. —COOH, or
4. —C(O)—NH—$C_3$-$C_6$cycloalkyl.

17. A compound according to claim 16, or a pharmaceutrically acceptable salt thereof wherein:
$R_3$ is hydrogen.

18. The compound according to claim 1, selected from the group consisting of:
8-(3-{2-(3-chlorophenyl)-4-[4-(methylsulfonyl)phenyl]-1,3-thiazol-5-yl}phenyl)-6-[1-methyl-1-(methylsulfonyl)ethyl]quinoline,
6-[1-methyl-1-(methylsulfonyl)ethyl]-8-{3-[4-[4-(methylsulfonyl)phenyl]-2-(1-oxidopyridin-4-yl)-1,3-thiazol-5-yl]phenyl}quinoline,
6-[1-methyl-1-(methylsulfonyl)ethyl]-8-{3-[4-[4-(methylsulfonyl)phenyl]-2-(1-oxidopyridin-3-yl)-1,3-thiazol-5-yl]phenyl}quinoline,
2-(3-{5-(3-{6-[1-methyl-1-(methylsulfonyl)ethyl]quinolin-8-yl}phenyl)-4-[4-(methylsulfonyl)phenyl]-1,3-thiazol-2-yl}phenyl)propan-2-ol,
3-{5-(3-{6-[1-methyl-1-(methylsulfonyl)ethyl]quinolin-8-yl}phenyl)-4-[4-(methylsulfonyl)phenyl]-1,3-thiazol-2-yl}benzoic acid,
2-{5-(3-{6-[1-methyl-1-(methylsulfonyl)ethyl]quinolin-8-yl}phenyl)-4-[4-(methylsulfonyl)phenyl]-1,3-thiazol-2-yl}propan-2-ol,
6-[1-methyl-1-(methylsulfonyl)ethyl]-8-(3-{2-(3-methyl-1,2,4-oxadiazol-5-yl)-4-[4-(methylsulfonyl)phenyl]-1,3-thiazol-5-yl}phenyl)quinoline,
6-[1-methyl-1-(methylsulfonyl)ethyl]-8-(3-{4-[4-(methylsulfonyl)phenyl]-1,3-thiazol-5-yl}phenyl)quinoline,
N-cyclopropyl-5-(3-{6-[1-methyl-1-(methylsulfonyl)ethyl]quinolin-8-yl}phenyl)-4-[4-(methylsulfonyl)phenyl]-1,3-thiazole-2-carboxamide,
6-[1-methyl-1-(methylsulfonyl)ethyl]-8-(3-{2-(6-methyl-1-oxidopyridin-3-yl)-4-[4-(methylsulfonyl)phenyl]-1,3-thiazol-5-yl}phenyl)quinoline,
2-[4-(4-chlorophenyl)-5-(3-{6-[1-methyl-1-(methylsulfonyl)ethyl]quinolin-8-yl}phenyl)-1,3-thiazol-2-yl]propan-2-ol,
6-[1-methyl-1-(methylsulfonyl)ethyl]-8-(3-{2-methyl-4-[4-(methylsulfonyl)phenyl]-1,3-oxazol-5-yl}phenyl)quinoline,
2-{4-(3-{6-[1-methyl-1-(methylsulfonyl)ethyl]quinolin-8-yl}phenyl)-5-[4-(methylsulfonyl)phenyl]-1,3-thiazol-2-yl}propan-2-ol,
1,1,1-trifluoro-N-{5-(3-{6-[1-methyl-1-(methylsulfonyl)ethyl]quinolin-8-yl}phenyl)-4-[4-(methylsulfonyl)phenyl]-1,3-thiazol-2-yl}methanesulfonamide,
2-[5-(3-{6-[1-methyl-1-(methylsulfonyl)ethyl]quinolin-8-yl}phenyl)-4-pyridin-3-yl-1,3-thiazol-2-yl]propan-2-ol,
2-[5-(3-{6-[1-methyl-1-(methylsulfonyl)ethyl]quinolin-8-yl}phenyl)-4-(1-oxidopyridin-3-yl)-1,3-thiazol-2-yl]propan-2-ol,
1-(4-chlorophenyl)-1-{4-(3-{6-[1-methyl-1-(methylsulfonyl)ethyl]quinolin-8-yl}phenyl)-5-[4-(methylsulfonyl)phenyl]-1,3-thiazol-2-yl}ethanol,
6-[1-methyl-1-(methylsulfonyl)ethyl]-8-(3-{3-[4-(methylsulfonyl)phenyl]thien-2-yl}phenyl)quinoline,
1-(3"-{6-[1-methyl-1-(methylsulfonyl)ethyl]quinolin-8-yl}-1,1':2',1"-terphenyl-4-yl)ethanone,
2-(3"-{6-[1-methyl-1-(methylsulfonyl)ethyl]quinolin-8-yl}-1,1':2',1"-terphenyl-4-yl)propan-2-ol,
6-[1-methyl-1-(methylsulfonyl)ethyl]-8-{3-[5-(3-methyl-1,2,4-oxadiazol-5-yl)-1-oxidopyridin-3-yl]phenyl}quinoline,
5-(3-{6-[1-methyl-1-(methylsulfonyl)ethyl]quinolin-8-yl}phenyl)-3-(3-methyl-1,2,4-oxadiazol-5-yl)pyridin-2(1H)-one,
6-[1-methyl-1-(methylsulfonyl)ethyl]-8-(3-{6-[4-(methylsulfonyl)phenyl]imidazo[2,1-b][1,3]thiazol-5-yl}phenyl)quinoline,
6-[1-methyl-1-(methylsulfonyl)ethyl]-8-(3-{2-[4-(methylsulfonyl)phenyl]imidazo[1,2-α]pyridin-3-yl}phenyl)quinoline
[3-{6-[1-methyl-1-(methylsulfonyl)ethyl]quinolin-8-yl}-4"-(methylthio)-1,1':2',1"-terphenyl-4'-yl]methanol,
[3-{6-[1-methyl-1-(methylsulfonyl)ethyl]quinolin-8-yl}-4"-(methylsulfonyl)-1,1':2',1"-terphenyl-4'-yl]methanol,
2-[3-{6-[1-methyl-1-(methylsulfonyl)ethyl]quinolin-8-yl}-4"-(methylsulfonyl)-1,1':2',1"-terphenyl-4'-yl]propan-2-ol,
3-{6-[1-methyl-1-(methylsulfonyl)ethyl]quinolin-8-yl}-4"-(methylsulfonyl)-1,1':2',1"-terphenyl-4'-carboxylic acid,
6-[1-methyl-1-(methylsulfonyl)ethyl]-8-(3-{2-[4-(methylsulfonyl)phenyl]-1-oxidopyridin-3-yl}phenyl)quinoline,
8-{3-[3-(4-fluorophenyl)-1,2,4-oxadiazol-5-yl]phenyl}-6-[1-methyl-1-(methylsulfonyl)ethyl]quinoline,
6-[1-methyl-1-(methylsulfonyl)ethyl]-8-(3-{4-[4-(methylthio)phenyl]pyridin-3-yl}phenyl)quinoline,
3"-{6-[1-methyl-1-(methylsulfonyl)ethyl]quinolin-8-yl}-1,1':2',1"-terphenyl-4-carboxylic acid,
2-(3-{6-[1-methyl-1-(methylsulfonyl)ethyl]quinolin-8-yl}phenyl)-3-[4-(methylsulfonyl)phenyl]quinoxaline,
6-[1-methyl-1-(methylsulfonyl)ethyl]-8-(3-{3-[4-(methylsulfonyl)phenyl]pyrazin-2-yl}phenyl)quinoline,
5-(3-{6-[1-methyl-1-(methylsulfonyl)ethyl]quinolin-8-yl}phenyl)-6-[4-(methylsulfonyl)phenyl]pyridin-2(1H)-one,
1-methyl-5-(3-{6-[1-methyl-1-(methylsulfonyl)ethyl]quinolin-8-yl}phenyl)-6-[4-(methylsulfonyl)phenyl]pyridin-2(1H)-one,
8-(3-{6-methoxy-2-[4-(methylsulfonyl)phenyl]pyridin-3-yl}phenyl)-6-[1-methyl-1-(methylsulfonyl)ethyl]quinoline,
8-(3-{6-(difluoromethoxy)-2-[4-(methylsulfonyl)phenyl]pyridin-3-yl}phenyl)-6-[1-methyl-1-(methylsulfonyl)ethyl]quinoline, 8-(3-{6-[(4-fluorobenzyl)oxy]-2-[4-(methylsulfonyl)phenyl]pyridin-3-yl}phenyl)-6-[1-methyl-1-(methylsulfonyl)ethyl]quinoline, 1-(4-fluorobenzyl)-5-(3-{6-[1-methyl-1-(methylsulfonyl)ethyl]quinolin-8-yl}phenyl) -6-[4-(methylsulfonyl)phenyl]pyridin-2(1H)-one, 5-(4-fluorophenyl)-6-(3-{6-[1-methyl-1-(methylsulfonyl)ethyl]quinolin-8-yl}phenyl)pyridin-2(1H)-one, 5-(4-fluorophenyl)-1-methyl-6-(3-{6-[1-methyl-1-(methylsulfonyl)ethyl]quinolin-8-yl}phenyl)pyridin-2(1H)-one, 8-{3-[3-(4-fluorophenyl)-6-methoxypyridin-2-yl]phenyl}-6-[1-methyl-1-(methylsulfonyl)ethyl]quinoline, or a pharmaceutically acceptable salt thereof.

19. The compound according to claim 1, of formula Ia:

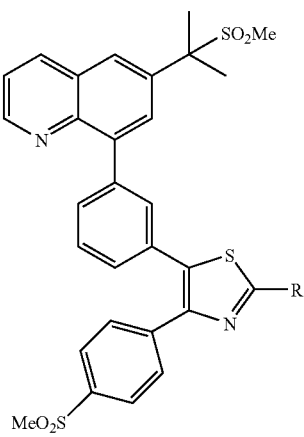

wherein

| R is selected from the group consisting of |
| --- |
| Amino |
| 2-biphenyl |
| 3-biphenyl |
| N-(tert-butoxycarbonyl)-4-phenylpyrrolidin-3-yl |
| N-(tert-butoxycarbonyl)azetidin-3-yl |
| N-(tert-butoxycarbonyl)pyrrolidin-3-yl |
| 3-chloro-4-fluorophenyl |
| 4-chlorophenoxymethyl |
| 2-chlorophenyl |
| 4-chlorophenyl |
| Ethoxycarbonyl |
| furan-2-yl |
| furan-3-yl |
| imidazol-2-yl |
| indan-1-yl |
| indan-2-yl |
| 1H-indol-2-yl |
| 1H-indol-3-yl |
| 1H-indol-4-yl |
| 1H-indol-5-yl |
| 1H-indol-6-yl |
| 1H-indol-7-yl |
| Isoquinolin-1-yl |
| Isoquinolin-4-yl |
| Isoquinolin-5-yl |
| Isoquinolin-8-yl |
| isoxazol-3-yl |
| 3-methoxycarbonylphenyl |
| 4-methoxycarbonylphenyl |
| Methyl |
| 1-methyl-1H-pyrazol-3-yl |
| 1-methyl-1H-pyrazol-4-yl |

-continued

| R is selected from the group consisting of |
| --- |
| 1-methyl-1H-pyrazol-5-yl |
| 2-methylphenyl |
| 3-methylphenyl |
| 4-methylphenyl |
| 2-methylpyridin-5-yl |
| Methylsulfonylmethyl |
| 2-methylsulfonylphenyl |
| 3-methylsulfonylphenyl |
| 4-methylsulfonylphenyl |
| morpholin-4-ylmethyl |
| Phenyl |
| Pyrazinyl |
| 1H-pyrazol-3-yl |
| pyridin-2-yl |
| pyridin-3-yl |
| pyridin-4-yl |
| 3-pyridinylmethyl |
| pyrimidin-2-yl |
| pyrimidin-4-yl |
| pyrimidin-5-yl |
| quinolin-4-yl |
| quinolin-5-yl |
| quinolin-8-yl |
| 5,6,7,8-tetrahydro-1,8-naphthyridin-2-yl |
| 6,7,8,9-tetrahydro-5H-benzo[a][7]annulen-5-yl |
| 6,7,8,9-tetrahydro-5H-benzo[a][7]annulen-6-yl |
| Tetrahydrofuran-2-yl |
| 1,2,3,4-tetrahydronaphthalen-1-yl |
| 1,2,3,4-tetrahydronaphthalen-2-yl |
| 1,3-thiazol-2-yl |
| 1,3-thiazol-5-yl |
| thiophen-2-yl |
| thiophen-3-yl. |

20. The compound according to claim 1, selected from the group consisting of:

6-[1-methyl-1-(methylsulfonyl)ethyl]-8-(3-{2-[3-(methylsulfonyl)phenyl]-4-phenyl -1,3-thiazol-5-yl}phenyl)quinoline, 2-[4-(3-chlorophenyl)-5-(3-{6-[1-methyl-1-(methylsulfonyl)ethyl]quinolin-8-yl}phenyl)-1,3-thiazol-2-yl]propan-2-ol, 2-[4-(4-fluorophenyl)-5-(3-{6-[1-methyl-1-(methylsulfonyl)ethyl]quinolin-8-yl}phenyl)-1,3-thiazol-2-yl]propan-2-ol, 8-{3-[4-(4-chlorophenyl)-2-quinolin-5-yl-1,3-thiazol-5-yl]phenyl}-6-[1-methyl-1-(methylsulfonyl)ethyl]quinoline, 2-{3-[4-(3-chlorophenyl)-5-(3-{6-[1-methyl-1-(methylsulfonyl)ethyl]quinolin-8-yl}phenyl)-1,3-thiazol-2-yl]phenyl}propan-2-ol, 2-{3-[4-(3-chloro-4-fluorophenyl)-5-(3-{6-[1-methyl-1-(methylsulfonyl)ethyl]quinolin-8-yl}phenyl)-1,3-thiazol-2-yl]phenyl}propan-2-ol, 2-{3-[4-[3,4-bis(difluoromethoxy)phenyl]-5-(3-{6-[1-methyl-1-(methylsulfonyl)ethyl]quinolin-8-yl}phenyl)-1,3-thiazol-2-yl]phenyl}propan-2-ol, N-{5-(3-{6-[1-methyl-1-(methylsulfonyl)ethyl]quinolin-8-yl}phenyl)-4-[4-(methylsulfonyl)phenyl]-1,3-thiazol-2-yl}acetamide, N-{5-(3-{6-[1-methyl-1-(methylsulfonyl)ethyl]quinolin-8-yl}phenyl)-4-[4-(methylsulfonyl)phenyl]-1,3-thiazol-2-yl}pyridin-4-amine, 2-[5-(3-{6-[1-methyl-1-(methylsulfonyl)ethyl]quinolin-8-yl}phenyl)-4-pyridin-4-yl-1,3-thiazol-2-yl]propan-2-ol, 2-[5-(3-{6-[1-methyl-1-(methylsulfonyl)ethyl]quinolin-8-yl}phenyl)-4-(1-oxidopyridin-4-yl)-1,3-thiazol-2-yl]propan-2-ol, 2-[5-(4-chlorophenyl)-4-(3-{6-[1-methyl-1-(methylsulfonyl)ethyl]quinolin-8-yl}phenyl)-1,3-thiazol-2-yl]propan-2-ol, 2-{3-[4-(4-chlorophenyl)-5-(3-{6-[1-methyl-1-(methylsulfonyl)ethyl]quinolin-8-yl}phenyl)-1,3-thiazol-2-yl]phenyl}propan-2-ol, and 6-[1-methyl-1-(methylsulfonyl)ethyl]-8-{3-[5-(1H-tetraazol-5-yl)pyridin-3-yl]phenyl}quinoline, or a pharmaceuticaly acceptable salt thereof.

21. The compound according to claim 1, selected from the group consisting of:

6-[1-methyl-1-(methylsulfonyl)ethyl]-8-(3-{5-[4-(methylsulfonyl)phenyl]-1-oxidopyridin-3-yl}phenyl)quinoline, 6-[1-methyl-1-(methylsulfonyl)ethyl]-8-(3-{5-[3-(methylsulfonyl)phenyl]-1-oxidopyridin-3-yl}phenyl)quinoline, 6-[1-methyl-1-(methylsulfonyl)ethyl]-8-(3-{5-[2-(methylsulfonyl)phenyl]-1-oxidopyridin-3-yl}phenyl)quinoline, 6-[1-methyl-1-(methylsulfonyl)ethyl]-8-(3-{2-[4-(methylsulfonyl)phenyl]pyridin-3-yl}phenyl)quinoline, 6-[1-methyl-1-(methylsulfonyl)ethyl]-8-[3-(1-oxido-5-phenylpyridin-3-yl)phenyl]quinoline, 8-{3-[5-(3,5-dichlorophenyl)-1-oxidopyridin-3-yl]phenyl}-6-[1-methyl-1-(methylsulfonyl)ethyl]quinoline, 8-{3-[5-(3,4-dimethoxyphenyl)-1-oxidopyridin-3-yl]phenyl}-6-[1-methyl-1-(methylsulfonyl)ethyl]quinoline, 6-[1-methyl-1-(methylsulfonyl)ethyl]-8-{3-[5-(5-methyl-1,2,4-oxadiazol-3-yl)-1-oxidopyridin-3-yl]phenyl}quinoline, 6-[1-methyl-1-(methylsulfonyl)ethyl]-8-{3-[5-(5-methyl-1,3,4-oxadiazol-2yl)-1-oxidopyridin-3-yl]phenyl}quinoline, 8-{3-[6-(benzyloxy)-5-(3-methyl-1,2,4-oxadiazol-5-yl)pyridin-3-yl]phenyl}-6-[1-methyl-1-(methylsulfonyl)ethyl]quinoline, 6-[1-methyl-1-(methylsulfonyl)ethyl]-8-(3-{6-[4-(methylsulfonyl)phenyl]-1-oxidopyridin-3-yl}phenyl)quinoline, 6-[1-methyl-1-(methylsulfonyl)ethyl]-8-(3-{5-[4-(methylsulfonyl)phenyl]-1-oxidopyridin-2-yl}phenyl)quinoline, 6-[1-methyl-1-(methylsulfonyl)ethyl]-8-{3-[3-[4-(methylsulfonyl)phenyl]-5-(trifluoromethyl)pyridin-2-yl]phenyl}quinoline, 1-(4-chlorophenyl)-3-(3-{6-[1-methyl-1-(methylsulfonyl)ethyl]quinolin-8-yl}phenyl)pyridin-2(1H)-one, N-isopropyl-5-(3-{6-[1-methyl-1-(methylsulfonyl)ethyl]quinolin-8-yl}phenyl)-4-[4-(methylsulfonyl)phenyl]thiophene-2-carboxamide, 6-[1-methyl-1-(methylsulfonyl)ethyl]-8-(1,1':2',1''-terphenyl-3-yl)quinoline, 6-[1-methyl-1-(methylsulfonyl)ethyl]-8-[4''-(methylthio)-1,1':2',1''-terphenyl-3-yl]quinoline, 6-[1-methyl-1-(methylsulfonyl)ethyl]-8-[2'-(5-methyl-1,3,4-oxadiazol-2-yl)-1,1'-biphenyl-3-yl]quinoline, methyl 3-{6-[1-methyl-1-(methylsulfonyl)ethyl]quinolin-8-yl}-4''-(methylsulfonyl)-1,1':2',1''-terphenyl-4'-carboxylate, 6-[1-methyl-1-(methylsulfonyl)ethyl]-8-(1,1':4',1''-terphenyl-3-yl)quinoline, 6-[1-methyl-1-(methylsulfonyl)ethyl]-8-(1,1':3',1''-terphenyl-3-yl)quinoline, 2-[5-(3'-{6-[1-methyl-1-(methylsulfonyl)ethyl]quinolin-8-yl}-1,1'-biphenyl-2-yl)-1,3-thiazol-2-yl]propan-2-ol, 6-[1-methyl-1-(methylsulfonyl)ethyl]-8-[3'-(1-oxidopyridin-4-yl)-1,1'-biphenyl-3-yl]quinoline, or a pharmaceutically acceptable salt thereof.

22. The compound according to claim 1, selected from the group consisting of:

6-[1-methyl-1-(methyl sulfonyl)ethyl]-8-(3-{4-[4-(methylsulfonyl)phenyl]pyridin-3-yl}phenyl)quinoline, 6-[1-methyl-1-(methylsulfonyl)ethyl]-8-(3-{4-[4-(methylsulfonyl)phenyl]-1-oxidopyridin-3-yl}phenyl)quinoline, 6-[1-methyl-1-(methylsulfonyl)ethyl]-8-(3-{4-[3-(methylthio)phenyl]pyridin-3-yl}phenyl)quinoline, 8-[4',5'-difluoro-4''-(methylthio)-1,1':2',1''-terphenyl-3-yl]-6-[1-methyl-1-(methylsulfonyl)ethyl]quinoline, 8-[4',5'-difluoro-4''-(methylsulfonyl)-1,1':2',1''-terphenyl-3-yl]-6-[1-methyl-1-(methylsulfonyl)ethyl]quinoline, 8-(4''-fluoro-1,1':2',1''-terphenyl-3-yl)-6-[1-methyl-1-(methylsulfonyl)ethyl]quinoline, 6,7-dichloro-2-(3-{6-[1-methyl-1-(methylsulfonyl)ethyl]quinolin-8-yl}phenyl)-3-[4-(methylsulfonyl)phenyl]quinoxaline, 2-(4-chlorophenyl)-3-(3-{6-[1-methyl-1-(methylsulfonyl)ethyl]quinolin-8-yl}phenyl)quinoxaline, 2-{4-[3-(3-{6-[1-methyl-1-(methylsulfonyl)ethyl]quinolin-8-yl}phenyl)quinoxalin-2-yl]phenyl}propan-2-ol, 2-[3,4-bis(difluoromethoxy)phenyl]-3-(3-{6-[1-methyl-1-(methylsulfonyl)ethyl]quinolin-8-yl}phenyl)quinoxaline, 4-[3-(3-{6-[1-methyl-1-(methylsulfonyl)ethyl]quinolin-8-yl}phenyl)quinoxalin-2-yl]benzoic acid, N-cyclopropyl-4-[3-(3-{6-[1-methyl-1-(methylsulfonyl)ethyl]quinolin-8-yl}phenyl)quinoxalin-2-yl]benzamide, 2-(3-{6-[1-methyl-1-(methylsulfonyl)ethyl]quinolin-8-yl}phenyl)-3-(4-methylphenyl)quinoxaline, 2-(3-{6-[1-methyl-1-(methylsulfonyl)ethyl]quinolin-8-yl}phenyl)-3-phenylquinoxaline, 2-(4-fluorophenyl)-3-(3-{6-[1-methyl-1-(methylsulfonyl)ethyl]quinolin-8-yl}phenyl)quinoxaline, 2-{4-[3-(3-{6-[1-methyl-1-(methylsulfonyl)ethyl]quinolin-8-yl}phenyl)pyrazin-2-yl]phenyl}propan-2-ol, 6-[1-methyl-1-(methylsulfonyl)ethyl]-8-(3-{3-[4-(methylthio)phenyl]pyrazin-2-yl}phenyl)quinoline, 8-{3-[3-(4-fluorophenyl)pyrazin-2-yl]phenyl}-6-[1-methyl-1-(methylsulfonyl)ethyl]quinoline, 8-(3-{2-(2-ethylpyridin-4-yl)-4-[4-(methylsulfonyl)phenyl]-1,3-thiazol-5-yl}phenyl)-6-[1-methyl-1-(methylsulfonyl)ethyl]quinoline, 2-(4-{5-(3-{6-[1-methyl-1-(methylsulfonyl)ethyl]quinolin-8-yl}phenyl)-4-[4-(methylsulfonyl)phenyl]-1,3-thiazol-2-yl}phenyl)propan-2-ol, or a pharmaceutically acceptable salt thereof.

23. A pharmaceutical composition comprising a therapeutically effective amount of the compound according to claim 1 or a pharmaceutically acceptable salt thereof; and a pharmaceutically acceptable carrier.

24. The pharmaceutical composition according to claim 18, further comprising a Leukotriene receptor antagonist, a Leukotriene biosynthesis inhibitor, an M2/M3 antagonist, a corticosteroid, an H1 receptor antagonist or a beta 2 adrenoceptor agonist.

25. The pharmaceutical composition according to claim 18, further comprising a COX-2 selective inhibitor, a statin, or an NSAID.

* * * * *